(12) United States Patent
Quinn et al.

(10) Patent No.: US 8,440,828 B2
(45) Date of Patent: May 14, 2013

(54) ORGANIC SEMICONDUCTORS AND DEVICES INCORPORATING SAME

(75) Inventors: Jordan Quinn, Skokie, IL (US); Yan Zheng, Skokie, IL (US); Zhihua Chen, Skokie, IL (US); Hakan Usta, Evanstan, IL (US); Christopher Newman, Evanston, IL (US); He Yan, Skokie, IL (US); Antonio Facchetti, Chicago, IL (US)

(73) Assignee: Polyera Corporation, Skokie, IL (US)

( * ) Notice: Subject to any disclaimer, the term of this patent is extended or adjusted under 35 U.S.C. 154(b) by 260 days.

(21) Appl. No.: 12/980,936

(22) Filed: Dec. 29, 2010

(65) Prior Publication Data

US 2011/0155247 A1    Jun. 30, 2011

Related U.S. Application Data

(60) Provisional application No. 61/290,676, filed on Dec. 29, 2009.

(51) Int. Cl.
*C07D 471/08*    (2006.01)
*H01L 29/00*    (2006.01)
*H01L 51/50*    (2006.01)

(52) U.S. Cl.
USPC ................. 546/37; 257/40; 313/504

(58) Field of Classification Search ............ 546/37; 257/40; 313/504
See application file for complete search history.

(56) References Cited

U.S. PATENT DOCUMENTS

2010/0207072 A1    8/2010 Pschirer et al.

FOREIGN PATENT DOCUMENTS

| EP | 1736476 | 12/2006 |
|---|---|---|
| JP | 4-45167 | 2/1992 |
| JP | 10-302961 | 11/1998 |
| JP | 2938149 | 6/1999 |
| JP | 2007-123716 | 5/2007 |
| JP | 2008-98454 | 4/2008 |
| WO | 2006/093965 | 9/2006 |
| WO | 2007/116001 | 10/2007 |
| WO | 2009/098252 | 8/2009 |

OTHER PUBLICATIONS

Nolde et al., "Synthesis and Self-Organization of Core-Extended Perylene Tetracarboxdiimides with Branched Alkyl Substituents," *Chem. Mater.*, 18:3715-3725 (2006).
Orzeszko et al., "Investigation of the Thionation Reaction of Cyclic Imides," *Z. Naturforsch*, 56b:1035-1040 (2001).
Huang et al., "The Improved Synthesis, Diels-Alder Reactions, and Desulfuration of Trithio-1,8-naphthalic Anhydride," *Heteroatom Chemistry* 10:141-146 (1999).
Huang et al., "General Synthesis of Thioxo-1,8-naphthalimides via Thioxo-1,8-naphthalic Anhydrides," *Synthesis*, 7:1109-1111 (1999).
Lakshmikantham et al., "Thione Analogues of 1,8-Naphthalic Anhydride. The First Cyclic Trithioanhydride," *J. Am. Chem. Soc.*, 106:6084-6085 (1984).

*Primary Examiner* — Charanjit Aulakh
(74) *Attorney, Agent, or Firm* — Karen K. Chan

(57) ABSTRACT

Disclosed are thionated fused-ring (aromatic) imides and diimides that can exhibit desirable electronic properties and can possess processing advantages including solution-processability and/or good stability at ambient conditions.

20 Claims, 10 Drawing Sheets

ORGANIC SEMICONDUCTORS AND DEVICES INCORPORATING SAME

CROSS REFERENCE TO RELATED APPLICATIONS

This application claims priority to and the benefit of U.S. Provisional Patent Application No. 61/290,676, filed on Dec. 29, 2009, the disclosure of which is incorporated by reference herein in its entirety.

BACKGROUND

Organic semiconductor materials are used widely in a variety of electronic applications including field-effect transistors, light-emitting diodes, and photovoltaic cells. A challenge remains, however, to produce electron-transporting (n-type) organic semiconductors that are stable under standard operating conditions in air.

Accordingly, there remains a need in the art for new air-stable and solution-processable n-type organic semiconducting compounds, compositions, and materials that can be integrated in various device designs including, but not limited to, complementary circuits, organic light emitting diodes, organic photovoltaics, capacitors, and sensors.

SUMMARY

In light of the foregoing, the present teachings provide organic semiconductors and associated devices that can address various deficiencies and shortcomings of the prior art, including those outlined above. More specifically, the present teachings provide organic semiconducting compounds and materials that are based on thionated N-functionalized fused-ring (aromatic) imides. It has been found that these compounds can afford useful electrical properties while offering a range of other properties that can be suitable for solution-phase processing.

In one aspect, the present teachings provide compounds having the formula:

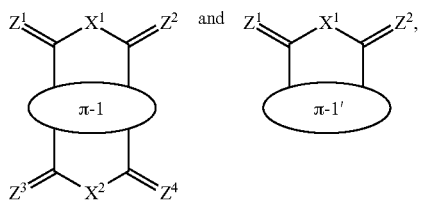

where $X^1$, $X^2$, $Z^1$, $Z^2$, $Z^3$, $Z^4$, π-1, and π-1' are as defined herein. Also provided are associated compositions, articles of manufacture, structures, and devices including the compounds disclosed herein and related methods for the preparation and use of these compounds.

The foregoing as well as other features and advantages of the present teachings will be more fully understood from the following figures, description, examples, and claims.

BRIEF DESCRIPTION OF DRAWINGS

It should be understood that the drawings described below are for illustration purposes only. The drawings are not necessarily to scale, with emphasis generally being placed upon illustrating the principles of the present teachings. The drawings are not intended to limit the scope of the present teachings in any way.

DETAILED DESCRIPTION

Figure 1:
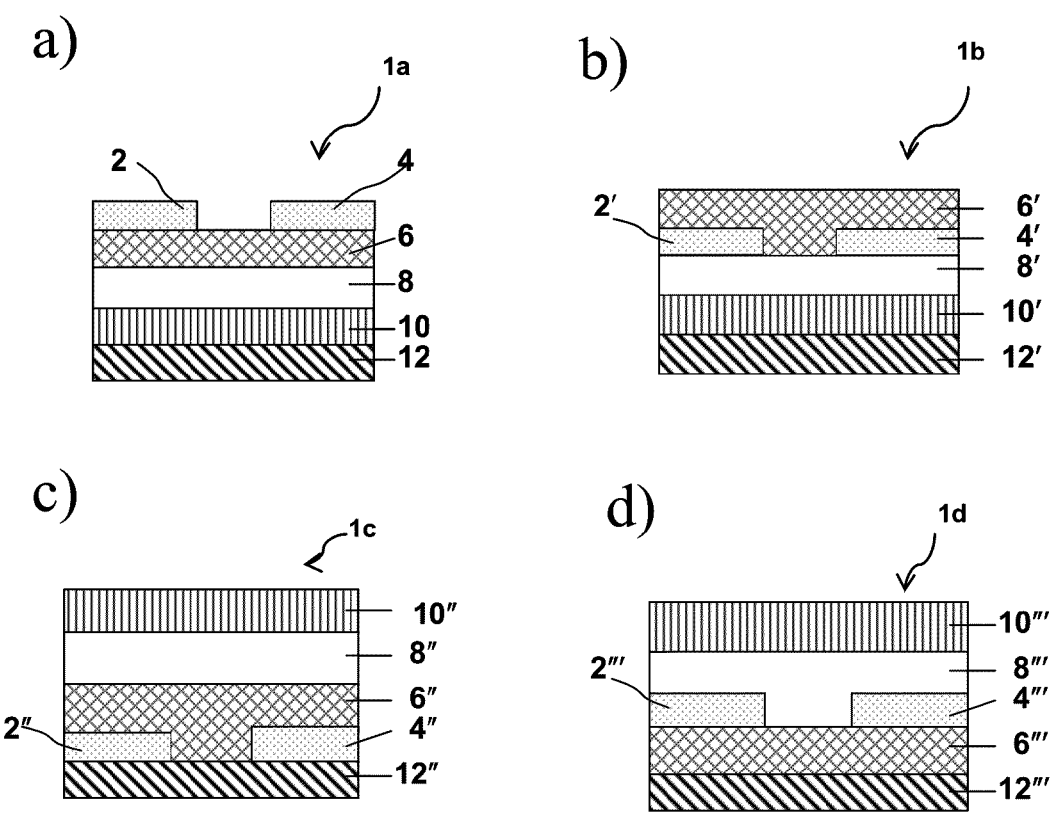
FIG. 1 illustrates four different configurations of thin film transistors: bottom-gate top contact (a), bottom-gate bottom-contact (b), top-gate bottom-contact (c), and top-gate top-contact (d); each of which can be used to incorporate compounds of the present teachings.

The present teachings provide various thionated fused-ring (aromatic) imides and diimides, as well as compositions, composites, and/or devices associated with these compounds. Compounds of the present teachings can exhibit semiconductor behavior such as high carrier mobility and/or good current modulation characteristics in a field-effect device, light absorption/charge separation in a photovoltaic device, and/or charge transport/recombination/light emission in a light-emitting device. For example, the present compounds can exhibit properties such as excellent charge transport characteristics in ambient conditions, chemical stability, low-temperature processability, large solubility in common solvents, and processing versatility (e.g., via various solution processes). As a result, field effect devices such as thin film transistors (TFTs) that incorporate one or more of the present compounds as the semiconductor layer can exhibit high performance in ambient conditions, for example, demonstrating one or more of the following properties including large electron carrier mobilities, low threshold voltages, and high current on-off ratios. Similarly, other organic semiconductor-based devices such as organic photovoltaic devices (OPVs), organic light-emitting transistors (OLETs), and organic light-emitting diodes (OLEDs) can be fabricated efficiently using the organic semiconductor materials described herein.

The present teachings also provide methods of preparing such compounds and semiconductor materials, as well as various compositions, composites, and devices that incorporate the compounds and semiconductor materials disclosed herein.

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly π-conjugated and can include polycyclic aromatic hydrocarbons such as rylenes (or analogs thereof containing one or more heteroatoms) having the formula:

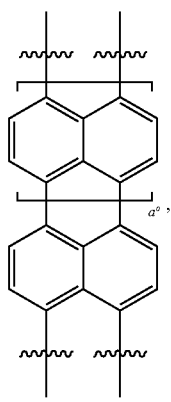

where $a^o$ can be an integer in the range of 0-3; coronenes (or analogs thereof containing one or more heteroatoms) having the formula:

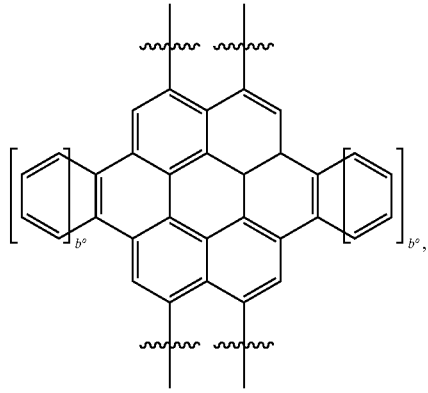

where $b^o$ can be an integer in the range of 0-3; and linear acenes (or analogs thereof containing one or more heteroatoms) having the formula:

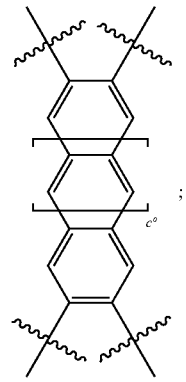

where $c^o$ can be an integer in the range of 0-4. The fused ring moiety can be optionally substituted as described herein.

As used herein, a "cyclic moiety" can include one or more (e.g., 1-6) carbocyclic or heterocyclic rings. The cyclic moiety can be a cycloalkyl group, a heterocycloalkyl group, an aryl group, or a heteroaryl group (i.e., can include only saturated bonds, or can include one or more unsaturated bonds regardless of aromaticity), each including, for example, 3-24 ring atoms and can be optionally substituted as described herein. In embodiments where the cyclic moiety is a "monocyclic moiety," the "monocyclic moiety" can include a 3-14 membered aromatic or non-aromatic, carbocyclic or heterocyclic ring. A monocyclic moiety can include, for example, a phenyl group or a 5- or 6-membered heteroaryl group, each of which can be optionally substituted as described herein. In embodiments where the cyclic moiety is a "polycyclic moiety," the "polycyclic moiety" can include two or more rings fused to each other (i.e., sharing a common bond) and/or connected to each other via a spiro atom, or one or more bridged atoms. A polycyclic moiety can include an 8-24 membered aromatic or non-aromatic, carbocyclic or heterocyclic ring, such as a $C_{8-24}$ aryl group or an 8-24 membered heteroaryl group, each of which can be optionally substituted as described herein.

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), butyl (e.g., n-butyl, iso-butyl, sec-butyl, tert-butyl), pentyl (e.g., n-pentyl, iso-pentyl, neopentyl), and hexyl groups. In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula $-C_zH_{2z+1-t}X^0{}_t$, where $X^0$, at each occurrence, is F, Cl, Br or I, z is an integer in the range of 1 to 40, and t is an integer in the range of 1 to 81, provided that t is less than or equal to $2z+1$. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxyl, hexoxyl groups, and the like. The alkyl group in the —O-alkyl group can be substituted as described herein.

As used herein, "alkylthio" refers to an —S-alkyl group (which, in some cases, can be expressed as —S(O)$_w$-alkyl, wherein w is 0). Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "arylalkyl" refers to an -alkyl-aryl group, where the arylalkyl group is covalently linked to the defined chemical structure via the alkyl group. An arylalkyl group is within the definition of a —Y—$C_{6-14}$ aryl group, where Y is as defined herein. An example of an arylalkyl group is a benzyl group (—$CH_2$—$C_6H_5$). An arylalkyl group can be optionally substituted, i.e., the aryl group and/or the alkyl group, can be substituted as disclosed herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., $C_{2-40}$ alkynyl group), for example, 2 to 20 carbon atoms (i.e., $C_{2-20}$ alkynyl group). In some embodiments, alkynyl groups can be substituted as described herein. An alkynyl group is generally not substituted with another alkynyl group, an alkyl group, or an alkenyl group.

As used herein, "cycloalkyl" refers to a non-aromatic carbocyclic group including cyclized alkyl, alkenyl, and alkynyl groups. In various embodiments, a cycloalkyl group can have 3 to 24 carbon atoms, for example, 3 to 20 carbon atoms (e.g., $C_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as described herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 24 ring atoms, for example, 3 to 20 ring atoms (e.g., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_{6-20}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

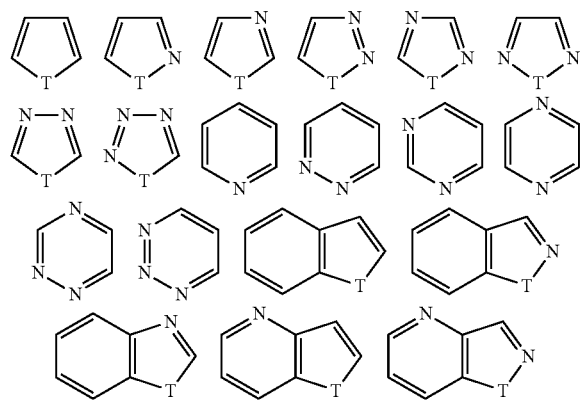

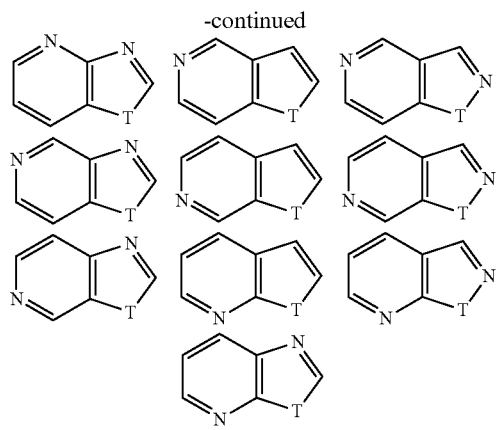

where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

Compounds of the present teachings can include a "divalent group" defined herein as a linking group capable of forming a covalent bond with two other moieties. For example, compounds of the present teachings can include a divalent $C_{1-40}$ alkyl group (e.g., a methylene group), a divalent $C_{2-40}$ alkenyl group (e.g., a vinylyl group), a divalent $C_{2-40}$ alkynyl group (e.g., an ethynylyl group), a divalent $C_{6-14}$ aryl group (e.g., a phenylyl group); a divalent 3-14 membered cycloheteroalkyl group (e.g., a pyrrolidylyl), and/or a divalent 5-14 membered heteroaryl group (e.g., a thienylyl group). Generally, a chemical group (e.g., —Ar—) is understood to be divalent by the inclusion of the two bonds before and after the group.

The electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein.

It should be understood that the term "electron-accepting group" can be used synonymously herein with "electron acceptor" and "electron-withdrawing group." In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halo (e.g., F, Cl, Br, I), —$NO_2$, —CN, —NC, —$S(R^0)_2{}^+$, —$N(R^0)_3{}^+$, —$SO_3H$, —$SO_2R^0$, —$SO_3R^0$, —$SO_2NHR^0$, —$SO_2N(R^0)_2$, —COOH, —$COR^0$, —$COOR^0$, —$CONHR^0$, —$CON(R^0)_2$, $C_{1-40}$ haloalkyl groups, $C_{6-14}$ aryl groups, and 5-14 membered electron-poor heteroaryl groups; where $R^0$ is a $C_{1-40}$ alkyl group, a $C_{2-40}$ alkenyl group, a $C_{2-40}$ alkynyl group, a $C_{1-40}$ haloalkyl group, a $C_{1-40}$ alkoxy group, a $C_{6-14}$ aryl group, a $C_{3-14}$ cycloalkyl group, a 3-14 membered cycloheteroalkyl group, and a 5-14 membered heteroaryl group, each of which can be optionally substituted as described herein.

It should be understood that the term "electron-donating group" can be used synonymously herein with "electron donor." In particular, an "electron-donating group" or an "electron-donor" refers to a functional group that donates electrons to a neighboring atom more than a hydrogen atom would if it occupied the same position in a molecule. Examples of electron-donating groups include —OH, —$OR^0$, —$NH_2$, —$NHR^0$, —$N(R^0)_2$, 5-14 membered electron-rich heteroaryl groups, $C_{1-40}$ alkyl groups, $C_{2-40}$ alkenyl groups, $C_{2-40}$ alkynyl groups, $C_{1-40}$ alkoxy groups, where $R^0$ is a $C_{1-40}$ alkyl group, a $C_{2-40}$ alkenyl group, a $C_{2-40}$ alkynyl group, a $C_{6-14}$ aryl group, or a $C_{3-14}$ cycloalkyl group.

Various unsubstituted heteroaryl groups can be described as electron-rich (or πexcessive) or electron-poor (or π-deficient). Such classification is based on the average electron density on each ring atom as compared to that of a carbon atom in benzene. Examples of electron-rich systems include 5-membered heteroaryl groups having one heteroatom such as furan, pyrrole, and thiophene; and their benzofused counterparts such as benzofuran, benzopyrrole, and benzothiophene. Examples of electron-poor systems include 6-membered heteroaryl groups having one or more heteroatoms such as pyridine, pyrazine, pyridazine, and pyrimidine; as well as their benzofused counterparts such as quinoline, isoquinoline, quinoxaline, cinnoline, phthalazine, naphthyridine, quinazoline, phenanthridine, acridine, and purine. Mixed heteroaromatic rings can belong to either class depending on the type, number, and position of the one or more heteroatom(s) in the ring. See Katritzky, A. R and Lagowski, J. M., *Heterocyclic Chemistry* (John Wiley & Sons, New York, 1960).

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan.

It is specifically contemplated that the depiction of one stereoisomer includes any other stereoisomer and any stereoisomeric mixtures unless specifically stated otherwise.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide ($N_3$), thiocyanate (SCN), nitro ($NO_2$), cyanate (CN), water ($H_2O$), ammonia ($NH_3$), and sulfonate groups (e.g., $OSO_2$—R, wherein R can be a $C_{1-10}$ alkyl group or a $C_{6-14}$ aryl group each optionally substituted with 1-4 groups independently selected from a $C_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

As used herein, a "p-type semiconductor material" or a "p-type semiconductor" refers to a semiconductor material having holes as the majority current carriers. In some embodiments, when a p-type semiconductor material is deposited on a substrate, it can provide a hole mobility in excess of about $10^{-5}$ $cm^2/Vs$. In the case of field-effect devices, a p-type semiconductor can also exhibit a current on/off ratio of greater than about 10.

As used herein, an "n-type semiconductor material" or an "n-type semiconductor" refers to a semiconductor material having electrons as the majority current carriers. In some embodiments, when an n-type semiconductor material is deposited on a substrate, it can provide an electron mobility in excess of about $10^{-5}$ $cm^2/Vs$. In the case of field-effect devices, an n-type semiconductor can also exhibit a current on/off ratio of greater than about 10.

As used herein, "field effect mobility" refers to a measure of the velocity with which charge carriers, for example, holes (or units of positive charge) in the case of a p-type semiconductor material and electrons in the case of an n-type semiconductor material, move through the material under the influence of an electric field.

As used herein, "solution-processable" refers to compounds, materials, or compositions that can be used in various solution-phase processes including spin-coating, printing (e.g., inkjet printing, screen printing, pad printing, offset printing, gravure printing, flexographic printing, lithographic printing, mass-printing and the like), spray coating, electrospray coating, drop casting, dip coating, and blade coating.

Throughout the specification, structures may or may not be presented with chemical names. Where any question arises as to nomenclature, the structure prevails.

In one aspect, the present teachings relate to compounds of formula I:

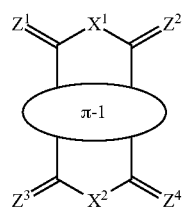

I wherein:

$X^1$ and $X^2$ independently are selected from O, S, and an amine group;

$Z^1$, $Z^2$, $Z^3$, and $Z^4$ independently are selected from O, S, and Se, provided that at least one of $Z^1$, $Z^2$, $Z^3$, and $Z^4$ is S or Se; and π-1 is a fused ring moiety optionally substituted with 1-4 electron-withdrawing groups.

For example, the present compounds can have a formula selected from:

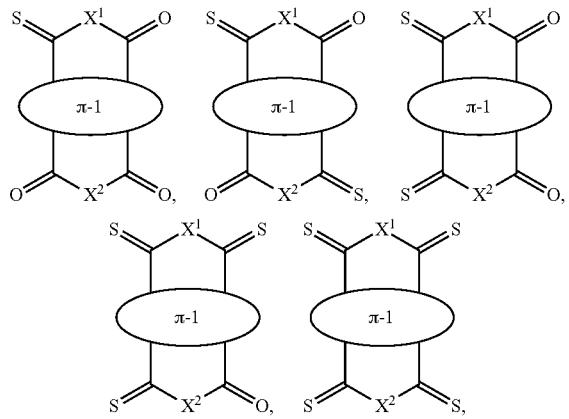

and their Se analogs (i.e., where S atoms are replaced by Se atoms), where $X^1$, $X^2$, and π-1 are as defined herein.

To further illustrate, $X^1$ and $X^2$ independently can be selected from O, S, and an amine group ($-NR^1$ or $-NR^2$), and thus, certain embodiments of the present compounds can have a formula selected from:

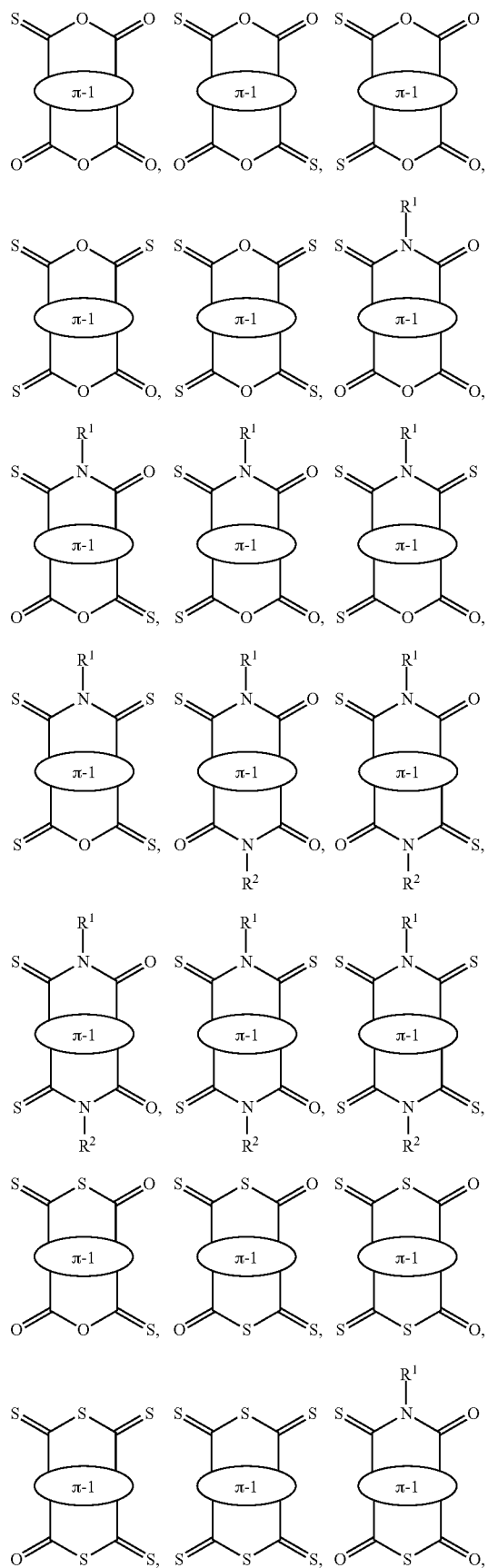

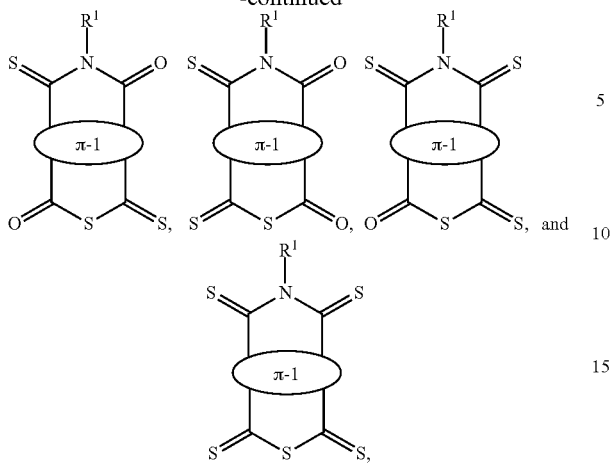

where $R^1$ and $R^2$ independently are selected from H, a $C_{1-40}$ alkyl group, a $C_{2-40}$ alkenyl group, a $C_{2-40}$ alkynyl group, a $C_{1-40}$ haloalkyl group, and a $C_{3-40}$ cycloalkyl group, wherein each of the $C_{1-40}$ alkyl group, the $C_{2-40}$ alkenyl group, the $C_{2-40}$ alkynyl group, the $C_{1-40}$ haloalkyl group, and the $C_{3-40}$ cycloalkyl group optionally can be substituted as described herein. For example, each of the $C_{1-40}$ alkyl group, the $C_{2-40}$ alkenyl group, the $C_{2-40}$ alkynyl group, and the $C_{1-40}$ haloalkyl group optionally can be substituted with 1-5 electron-withdrawing groups. Examples of electron-withdrawing groups include halogen, —CN, $NO_2$, —$SO_3H$, —$N(R^o)_3^+$, —$COR^o$, —$COOR^o$, and haloalkyl groups, where $R^o$, at each occurrence, independently can be H or an alkyl group. In addition, each of the $C_{1-40}$ alkyl group, the $C_{2-40}$ alkenyl group, the $C_{2-40}$ alkynyl group, the $C_{1-40}$ haloalkyl group, and the $C_{3-40}$ cycloalkyl group optionally can be bonded covalently to the imide nitrogen atom via an optional linker (L). For example, the optional linker (L) can be a linker selected from —Y—O—Y—, —Y—[S(O)$_w$]—Y—, —Y—C(O)—Y—, —Y—[NR$^c$C(O)]—Y—, —Y—[C(O)NR$^c$]—, —Y—NR$^c$—Y—, —Y—[SiR$^c_2$]—Y—, where Y, at each occurrence, independently is selected from a divalent $C_{1-40}$ alkyl group, a divalent $C_{2-40}$ alkenyl group, a divalent $C_{1-40}$ haloalkyl group, and a covalent bond; $R^c$ is selected from H, a $C_{1-6}$ alkyl group, a $C_{6-14}$ aryl group, and a —$C_{1-6}$ alkyl-$C_{6-14}$ aryl group; and w is 0, 1, or 2.

The optionally substituted fused ring moiety comprising π-1 can be, for example, a rylene, a coronene, or an acene as respectively represented by the formula:

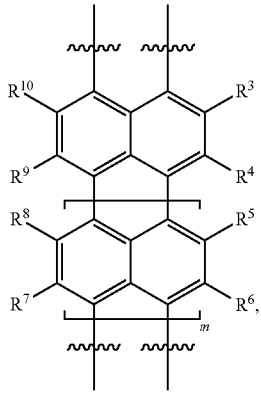

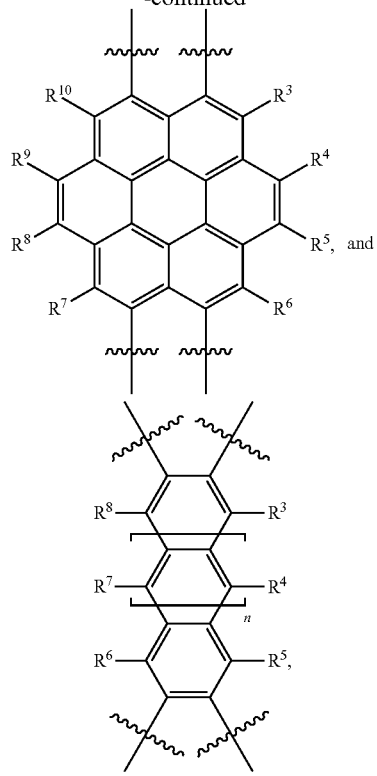

where m is 0, 1, or 2; n is 0, 1, 2, or 3; and $R^3$, $R^4$, $R^5$, $R^6$, $R^7$, $R^8$, $R^9$, and $R^{10}$, at each occurrence, independently are H or an electron-withdrawing group. For example, $R^3$, $R^4$, $R^5$, $R^6$, $R^7$, $R^8$, $R^9$, and $R^{10}$, at each occurrence, independently can be selected from H, a halogen (e.g., F, Cl, Br, or I), —CN, $NO_2$, —$SO_3H$, —$N(R^o)_3^+$, —$COR^o$, —$COOR^o$, and a $C_{1-6}$ haloalkyl group (e.g., $CF_3$, $CF_2CF_3$, or $CH_2CF_3$), where $R^o$, at each occurrence, independently can be H or a $C_{1-6}$ alkyl group (e.g., $CH_3$ or $CH_2CH_3$).

In certain embodiments, the optionally substituted fused ring moiety can be a rylene, and compounds according to these embodiments can be represented by the formula:

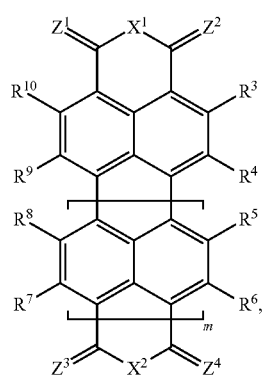

wherein:
$X^1$ and $X^2$ independently can be O, S, or an amine group;
$Z^1$, $Z^2$, $Z^3$, and $Z^4$ independently can be selected from O, S, and Se, provided that at least one of $Z^1$, $Z^2$, $Z^3$, and $Z^4$ is S or Se;
m is 0, 1 or 2; and $R^3$, $R^4$, $R^5$, $R^6$, $R^7$, $R^8$, $R^9$, and $R^{10}$ independently are H or an electron-withdrawing group as defined herein.

In various embodiments, the present compounds can have a perylene core and be represented by formula Ia:

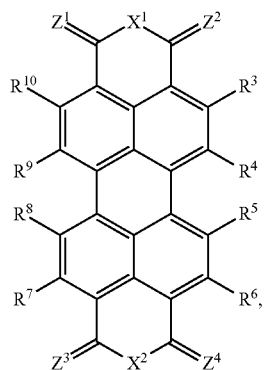

Ia where $X^1$, $X^2$, $Z^1$, $Z^2$, $Z^3$, $Z^4$, $R^3$, $R^4$, $R^5$, $R^6$, $R^7$, $R^8$, $R^9$, and $R^{10}$ are as defined herein.

For example, $Z^1$, $Z^2$, $Z^3$, and $Z^4$ can be defined as illustrated by the formulae:

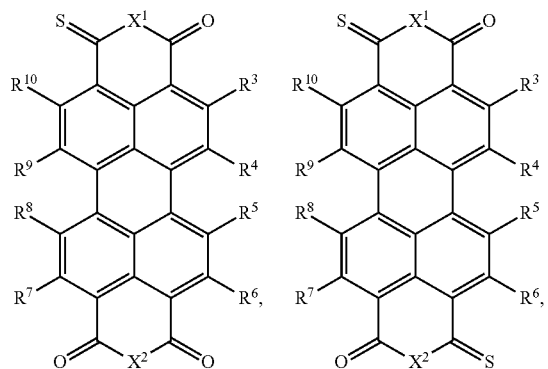

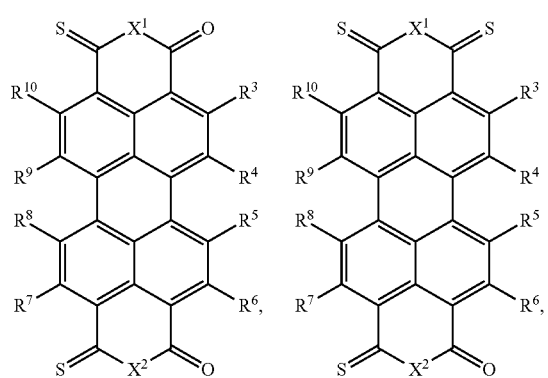

-continued

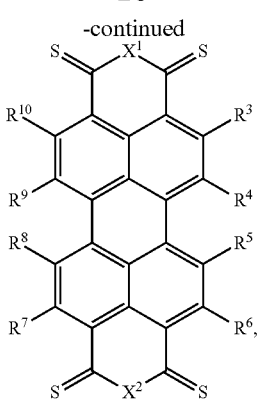

and their Se analogs (i.e., where S atoms are replaced by Se atoms), where $X^1$, $X^2$, $R^3$, $R^4$, $R^5$, $R^6$, $R^7$, $R^8$, $R^9$, and $R^{10}$ are as defined herein.

To further illustrate, $X^1$ and $X^2$ can be defined as illustrated by the formulae:

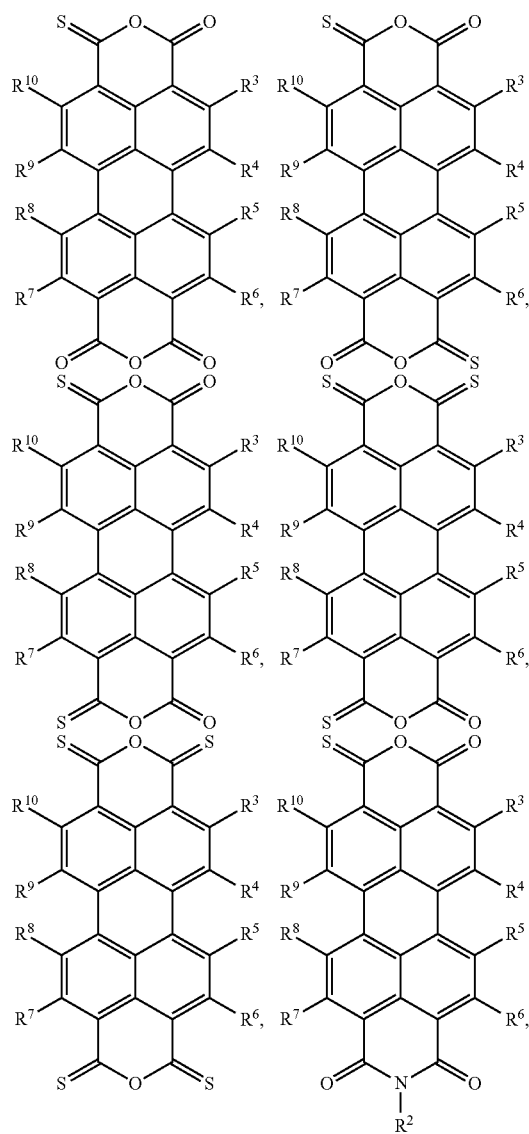

-continued

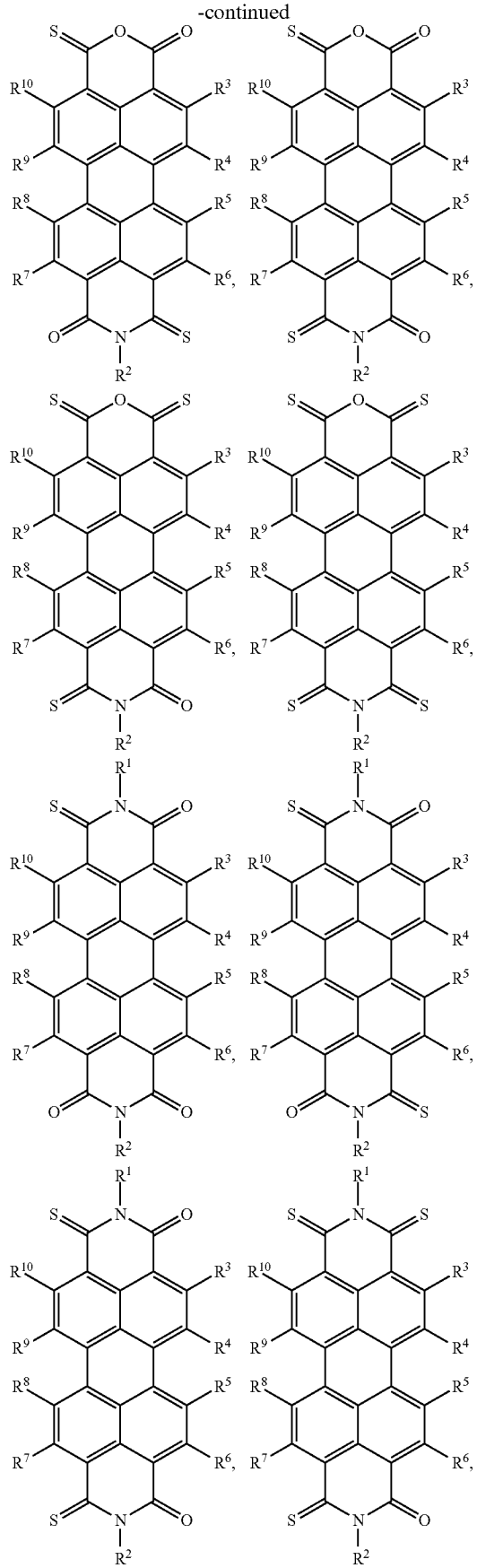

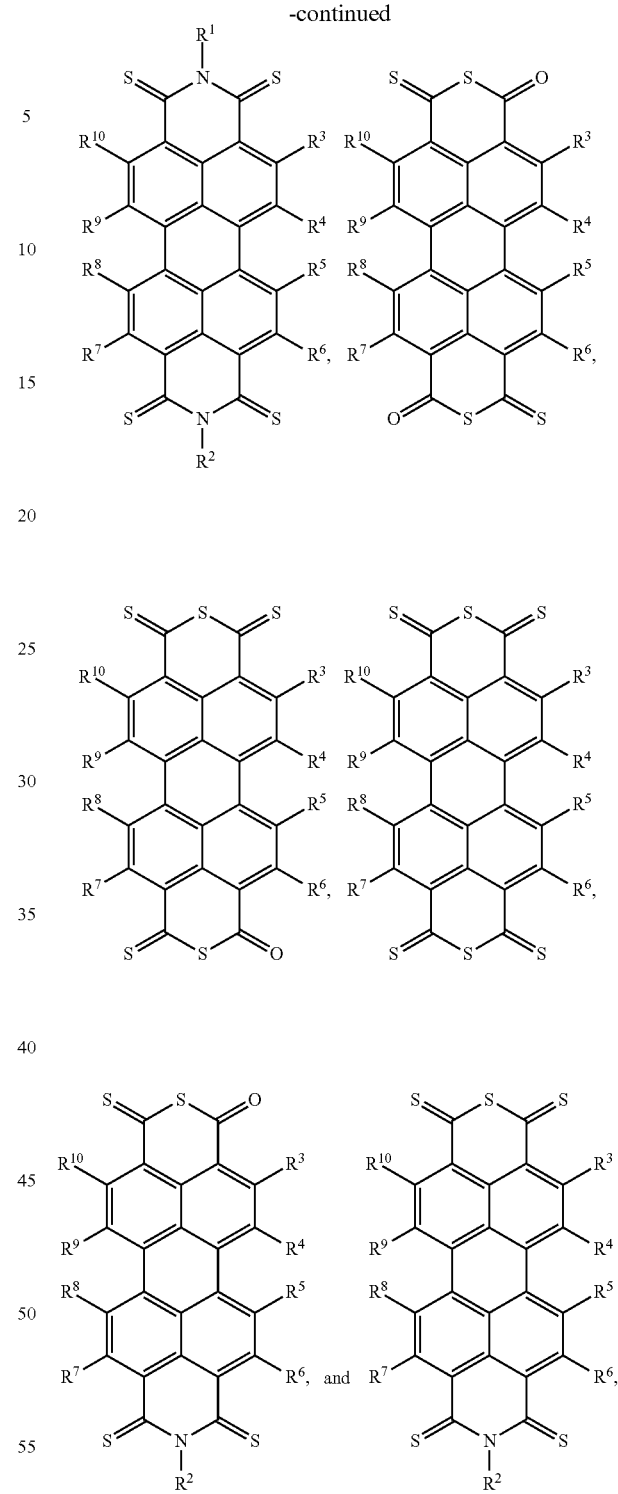

where $R^1$, $R^2$, $R^3$, $R^4$, $R^5$, $R^6$, $R^7$, $R^8$, $R^9$, and $R^{10}$ are as defined herein. In particular embodiments, $R^3$, $R^4$, $R^5$, $R^6$, $R^7$, $R^8$, $R^9$, and $R^{10}$, at each occurrence, independently can be selected from H, F, Cl, Br, CN, $NO_2$, and a $C_{1-6}$ haloalkyl group.

In certain embodiments, $X^1$ and $X^2$ can be $NR^1$ and $NR^2$, respectively, and certain compounds of the present teachings can be represented by the formula:

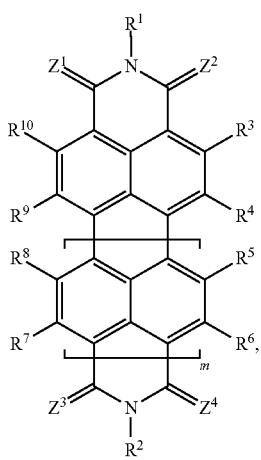

wherein:

$R^1$ and $R^2$ independently can be selected from H, a $C_{1-40}$ alkyl group, a $C_{2-40}$ alkenyl group, a $C_{2-40}$ alkynyl group, a $C_{1-40}$ haloalkyl group, and a $C_{3-40}$ cycloalkyl group, wherein each of the $C_{1-40}$ alkyl group, the $C_{2-40}$ alkenyl group, the $C_{2-40}$ alkynyl group, the $C_{1-40}$ haloalkyl group, and the $C_{3-40}$ cycloalkyl group can be optionally substituted as described herein;

$R^3$, $R^4$, $R^5$, $R^6$, $R^7$, $R^8$, $R^9$, and $R^{10}$, at each occurrence, independently can be selected from H and an electron-withdrawing group ($R^a$) such as F, Cl, Br, CN, $NO_2$, and a $C_{1-10}$ haloalkyl group;

$Z^1$, $Z^2$, $Z^3$, and $Z^4$ independently can be selected from O, S, and Se, provided that at least one of $Z^1$, $Z^2$, $Z^3$, and $Z^4$ is S or Se; and m can be 0, 1 or 2.

For example, certain compounds of the present teachings can be represented by the formula:

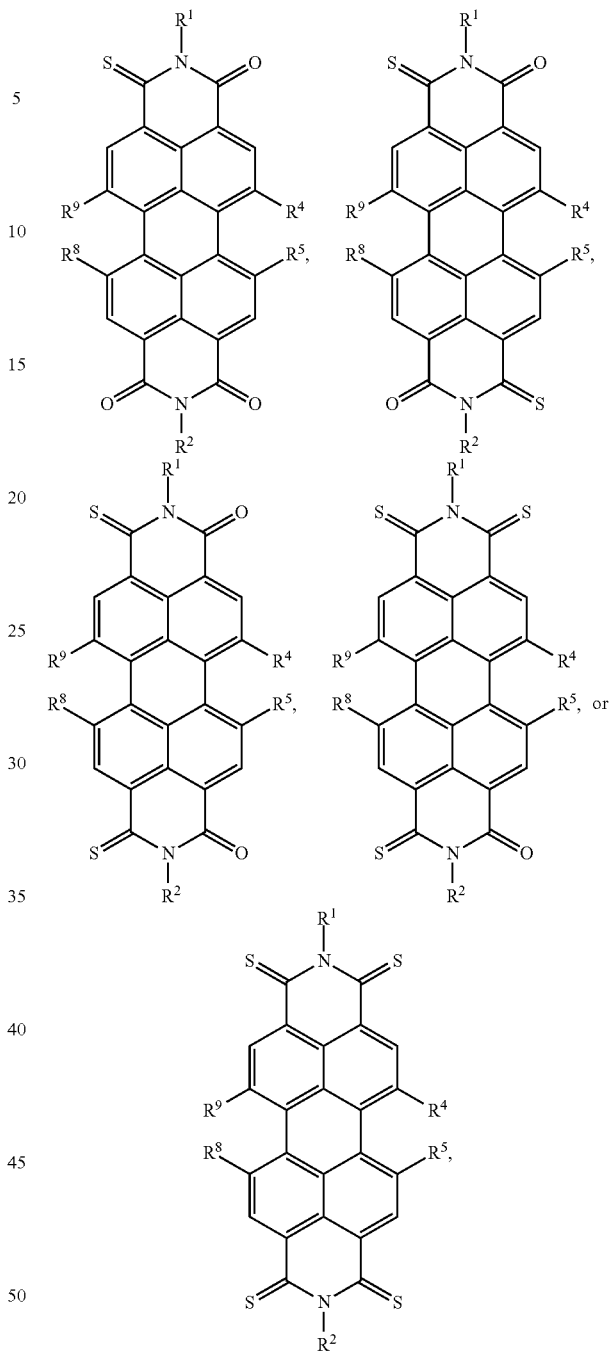

where $R^1$, $R^2$, $R^3$, $R^4$, $R^5$, $R^6$, $R^7$, $R^8$, $R^9$, $R^{10}$, $Z^1$, $Z^2$, $Z^3$, and $Z^4$ are as defined herein.

In particular embodiments, $R^3$, $R^6$, $R^7$, and $R^{10}$ can be H. Compounds according to these embodiments can have the formula:

where $R^4$, $R^5$, $R^8$, and $R^9$ (i.e., the four bay positions) independently can be H or $R^a$, and $R^a$, $R^1$ and $R^2$ are as defined herein. For example, $R^a$, at each occurrence, independently can be selected from a halogen, —CN, $NO_2$, —$SO_3H$, —$N(R^0)_3^+$, —$COR^0$, —$COOR^0$, and a $C_{1-6}$ haloalkyl group, where $R^0$, at each occurrence, independently can be H or a $C_{1-6}$ alkyl group. In various embodiments, the above perylene compounds can be (1,6- or 1,7-) disubstituted or tetrasubstituted with F, Cl, Br, or CN. For example, each of $R^4$, $R^5$, $R^8$, and $R^9$ independently can be selected from F, Cl, Br, and CN. In particular embodiments, two of $R^4$, $R^5$, $R^8$, and $R^9$ can be CN, and the other two of $R^4$, $R^5$, $R^8$, and $R^9$ can be selected from F, Cl, and Br. In other embodiments, two of $R^4$, $R^5$, $R^8$, and $R^9$ can be H, while the other two of $R^4$, $R^5$, $R^8$, and $R^9$ can be selected from F, Cl, Br, and CN. For example, one of $R^4$ and $R^5$ can be H and one of $R^8$ and $R^9$ can be H, while the other of $R^4$ and $R^5$ and the other of $R^8$ and $R^9$ can be selected from F, Cl, Br, and CN.

In some embodiments, the perylene compounds can have an unsubstituted core. Compounds according to these embodiments can have a formula selected from:

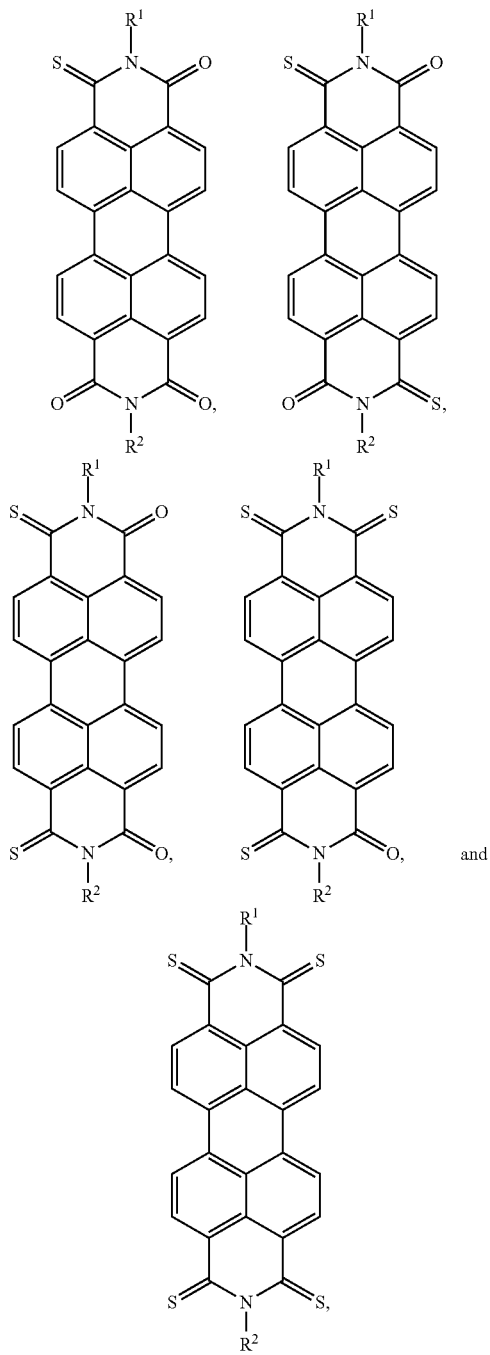

where $R^1$ and $R^2$ can be H or a substituent as described herein. For example, in various embodiments, $R^1$ and $R^2$ independently can be H or a substituent which can impart improved desirable properties to the compound as a whole. For example, certain substituents including one or more electron-withdrawing or electron-donating moieties can modulate the electronic properties of the compound, while substituents that include one or more aliphatic chains can improve the solubility of the compound in organic solvents.

Accordingly, in certain embodiments, $R^1$ and $R^2$ independently can be a $C_{1-40}$ alkyl group, a $C_{2-40}$ alkenyl group, a $C_{2-40}$ alkynyl group, and a $C_{1-40}$ haloalkyl group (e.g., a $C_{3-40}$ alkyl group, a $C_{4-40}$ alkenyl group, a $C_{4-40}$ alkynyl group, and a $C_{3-40}$ haloalkyl group), where each of these groups can be linear or branched, and can be optionally substituted as described herein. For example, $R^1$ and $R^2$ independently can be a $C_{2-40}$ alkenyl or alkynyl group optionally substituted with 1-5 substituents independently selected from a halogen, —CN, $NO_2$, —$SO_3H$, —$N(R^o)_3^+$, —$COR^o$, and —$COOR^o$; or $R^1$ and $R^2$ independently can be a $C_{1-40}$ alkyl or haloalkyl group optionally substituted with 1-5 substituents independently selected from a —CN, $NO_2$, —$SO_3H$, —$N(R^o)_3^+$, —$COR^o$, and —$COOR^o$, where $R^o$, at each occurrence, independently can be H or a $C_{1-40}$ alkyl group. In certain embodiments, $R^1$ and $R^2$ independently can be selected from a $C_{6-40}$ alkyl group, a $C_{6-40}$ alkenyl group, a $C_{6-40}$ alkynyl group, and a $C_{6-40}$ haloalkyl group, each of which can be linear or branched, and can be optionally substituted as described herein. In particular embodiments, $R^1$ and $R^2$ independently can be a $C_{6-40}$ alkyl group, a $C_{6-40}$ alkenyl group, or a $C_{6-40}$ haloalkyl group, which can be either linear or branched, and can be optionally substituted as described herein. For example, $R^1$ and $R^2$ independently can be a branched $C_{3-40}$ alkyl group represented by the formula:

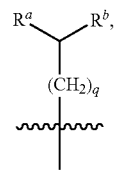

where $R^a$ and $R^b$ independently are a linear or branched $C_{1-20}$ alkyl group, and q is 0, 1, 2, 3, 4, 5, 6, 7, 8, 9 or 10. In certain embodiments, $R^1$ and $R^2$ independently can be a branched $C_{4-40}$ alkenyl group (similar to the branched $C_{3-40}$ alkyl group specified above but with one or more —$CH_2CH_2$— groups replaced by —CH=CH— groups). In certain embodiments, $R^1$ and $R^2$ independently can be a branched $C_{3-40}$ haloalkyl group (similar to the branched $C_{3-40}$ alkyl group specified above but with one or more hydrogen atoms replaced by halogen atoms such as F).

For example, specific examples of $R^1$ and $R^2$ can include linear or branched $C_{1-40}$ alkyl groups and $C_{2-40}$ alkenyl groups such as:

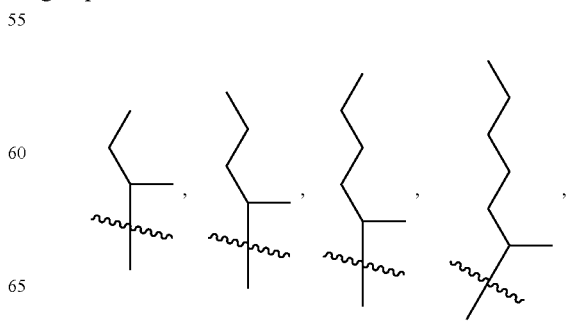

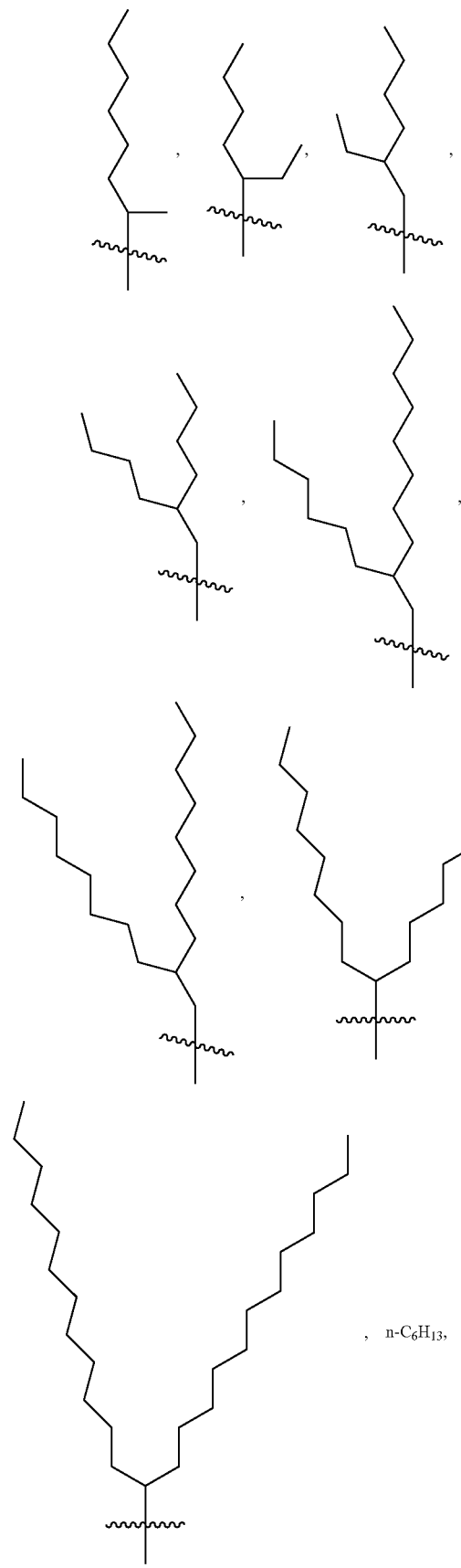

, n-C$_6$H$_{13}$, n-C$_{12}$H$_{25}$,

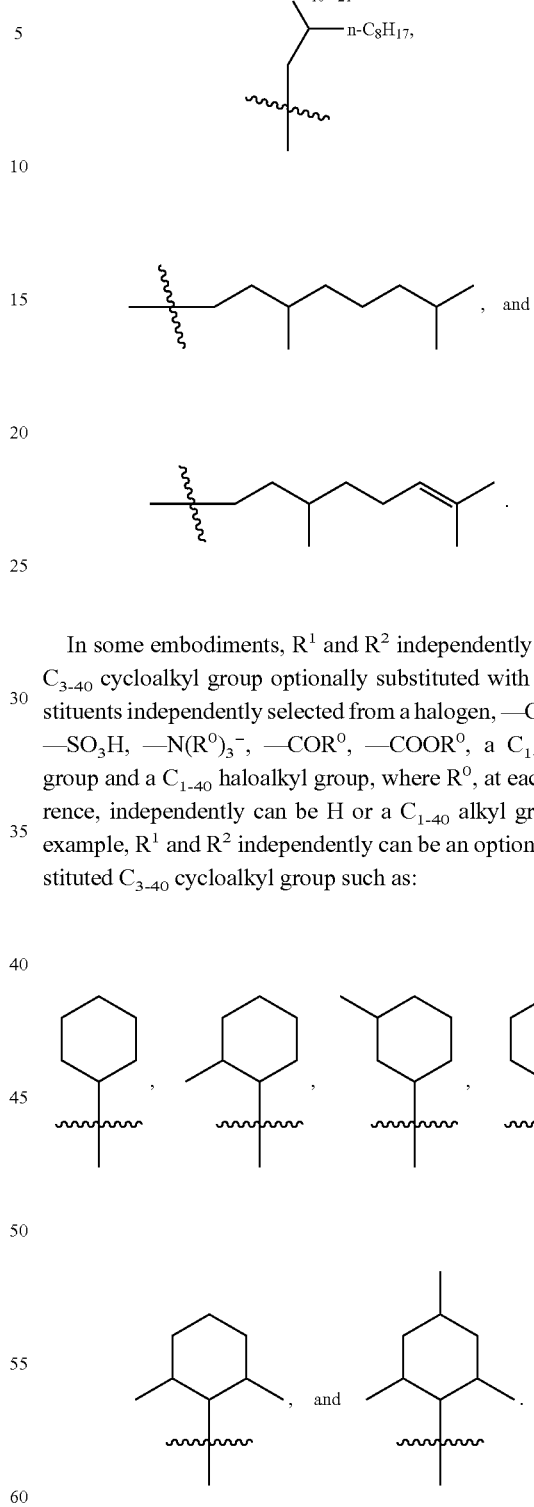

In some embodiments, R$^1$ and R$^2$ independently can be a C$_{3-40}$ cycloalkyl group optionally substituted with 1-5 substituents independently selected from a halogen, —CN, NO$_2$, —SO$_3$H, —N(R$^o$)$_3^-$, —COR$^o$, —COOR$^o$, a C$_{1-40}$ alkyl group and a C$_{1-40}$ haloalkyl group, where R$^o$, at each occurrence, independently can be H or a C$_{1-40}$ alkyl group. For example, R$^1$ and R$^2$ independently can be an optionally substituted C$_{3-40}$ cycloalkyl group such as:

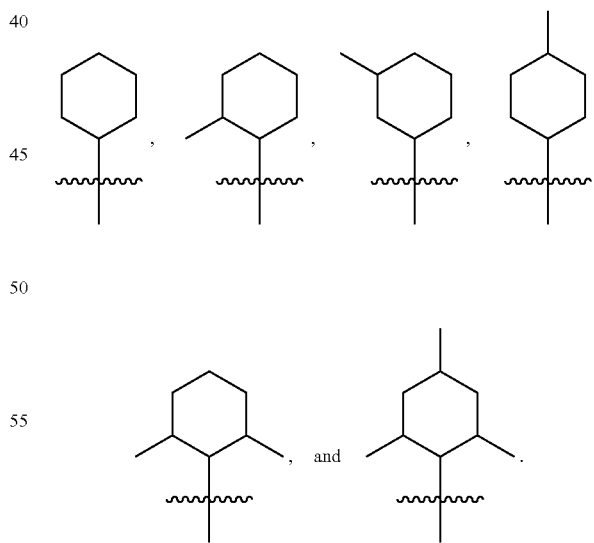

To further illustrate, certain compounds of the present teachings can be thionated in the trans positions (i.e., Z$^1$=Z$^4$=S and Z$^2$=Z$^3$=O) and have a formula selected from:

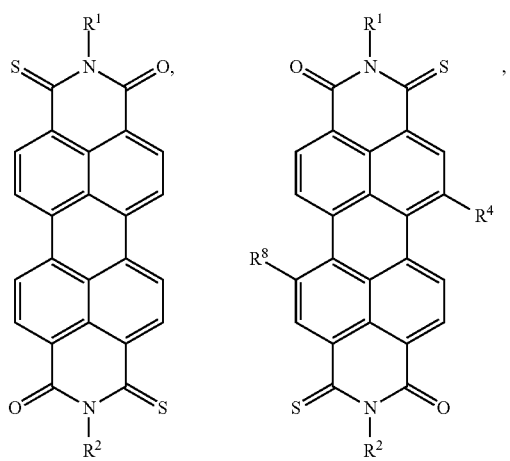 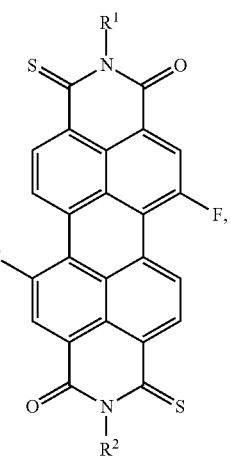 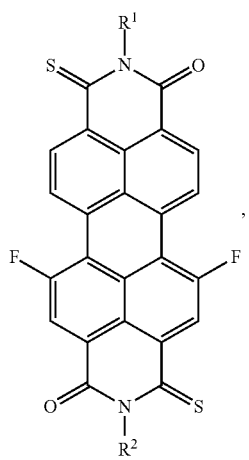
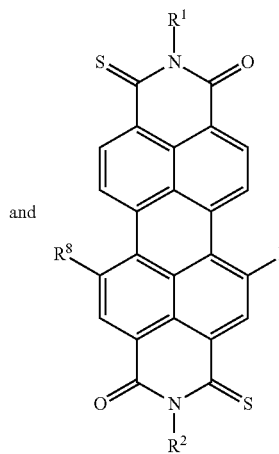
wherein $R^1$, $R^2$, $R^4$, $R^5$, and $R^8$ are as defined herein. For example, each of $R^4$, $R^5$ and $R^8$ can be an electron-withdrawing group independently selected from F, Cl, Br, I, CN, $CF_3$, $CH_2CF_3$ and $CF_2CF_3$. Particular examples of these embodiments can include:
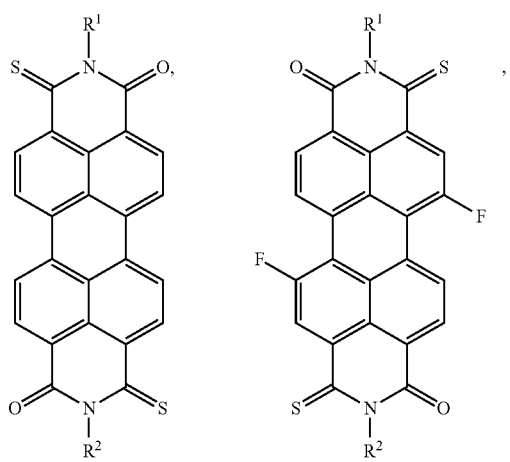 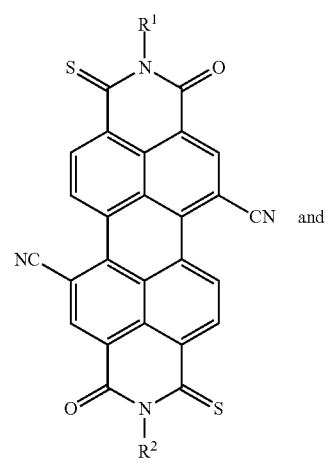

-continued

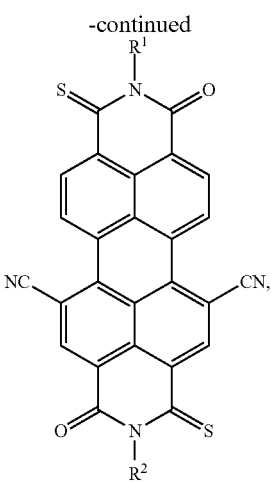

wherein $R^1$ and $R^2$ can be selected from a linear $C_{1-40}$ alkyl group, a linear $C_{2-40}$ alkenyl group, a linear $C_{1-40}$ haloalkyl group, a branched $C_{3-40}$ alkyl group, a branched $C_{4-40}$ alkenyl group, and a branched $C_{3-40}$ haloalkyl group, each of which can be optionally substituted as described herein.

In some embodiments, the present compounds can have a formula selected from:

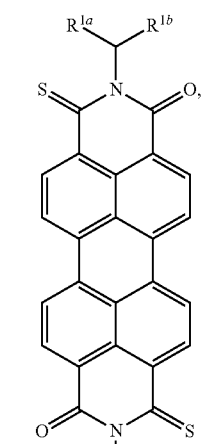 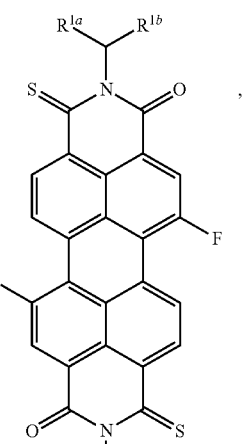 ,

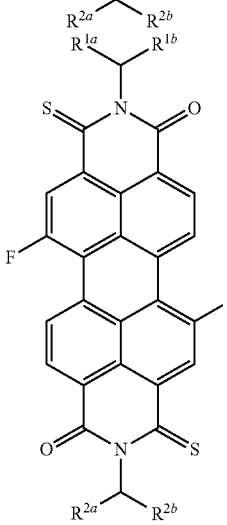 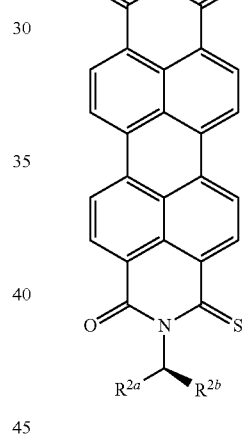 , and

-continued

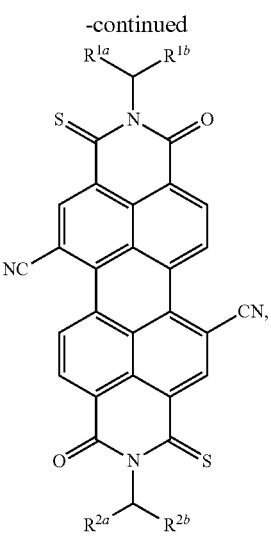

including stereoisomers thereof such as:

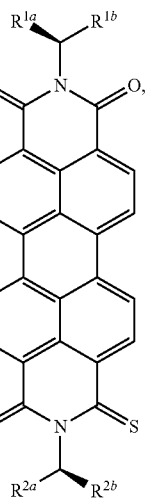 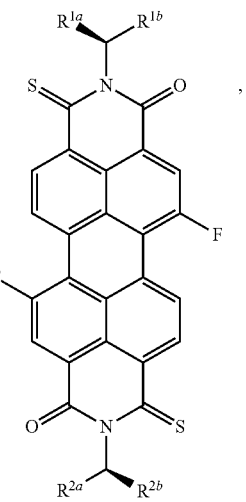

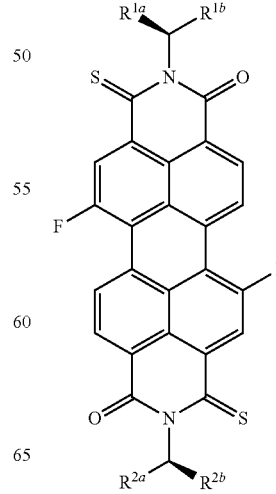 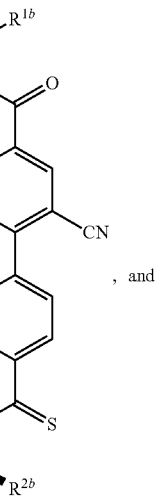 , and

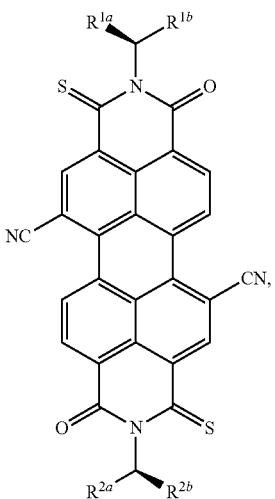

where $R^{1a}$, $R^{1b}$, $R^{2a}$ and $R^{2b}$ independently can be a $C_{1-20}$ alkyl group or a $C_{1-20}$ haloalkyl group. In certain embodiments, $R^{1a}$ can be different from $R^{1b}$, and $R^{2a}$ can be different from $R^{2b}$. In certain embodiments, one of $R^{1a}$ and $R^{1b}$ and one of $R^{2a}$ and $R^{2b}$ can be $CH_3$, while the other of $R^{1a}$ and $R^{1b}$ and $R^{2a}$ and $R^{2b}$ can be a $C_{2-20}$ alkyl group, for example, a $C_{4-20}$ alkyl group. In certain embodiments, one of $R^{1a}$ and $R^{1b}$ and one of $R^{2a}$ and $R^{2b}$ can be —$CH_2CH_3$, while the other of $R^{1a}$ and $R^{1b}$ and $R^{2a}$ and $R^{2b}$ can be a $C_{4-20}$ alkyl group.

In some embodiments, the present compounds can have a formula selected from:

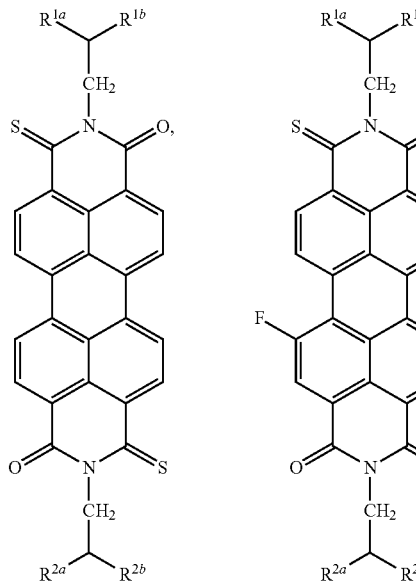

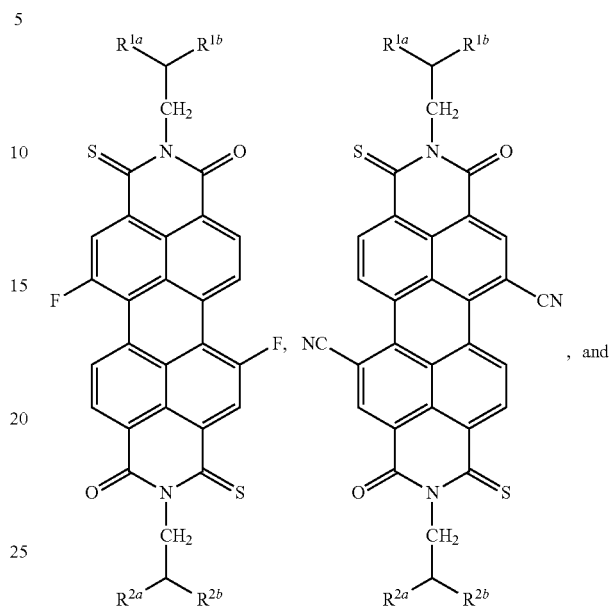

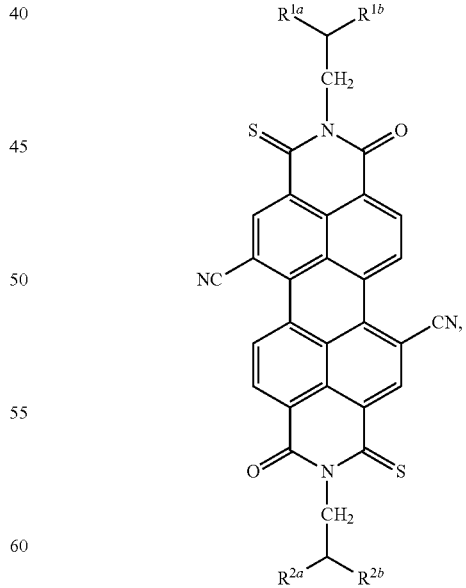

, and including stereoisomers thereof such as:

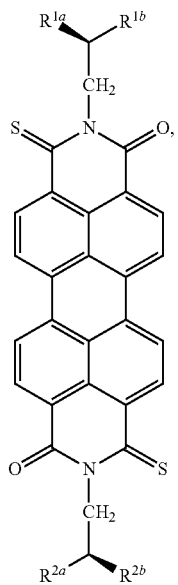
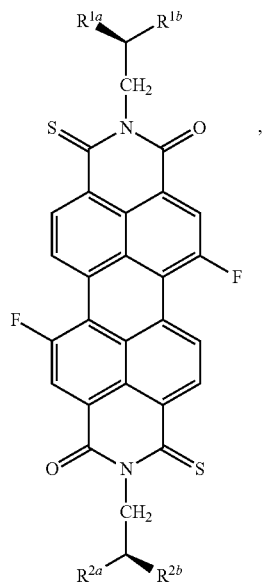

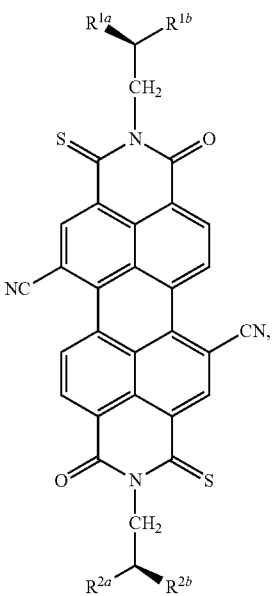

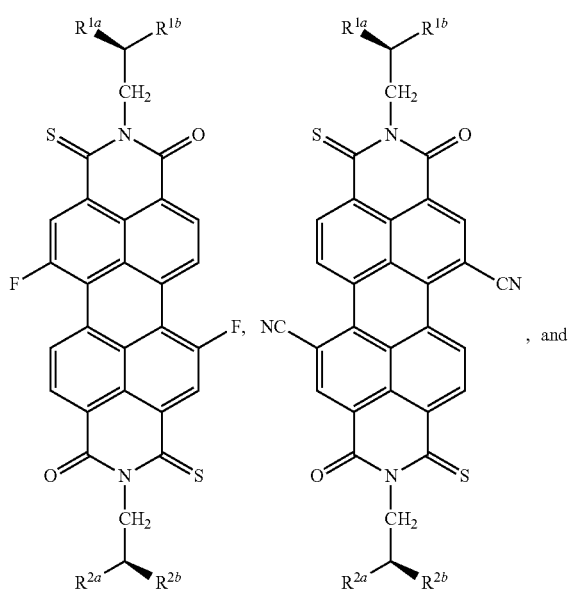, and where $R^{1a}$, $R^{1b}$, $R^{2a}$ and $R^{2b}$ independently can be a $C_{1-20}$ alkyl group or a $C_{1-20}$ haloalkyl group. In certain embodiments, $R^{1a}$ can be different from $R^{1b}$, and $R^{2a}$ can be different from $R^{2b}$. In certain embodiments, one of $R^{1a}$ and $R^{1b}$ and one of $R^{2a}$ and $R^{2b}$ can be $CH_3$, while the other of $R^{1a}$ and $R^{1b}$ and $R^{2a}$ and $R^{2b}$ can be a $C_{2-20}$ alkyl group, for example, a $C_{4-20}$ alkyl group. In certain embodiments, one of $R^{1a}$ and $R^{1b}$ and one of $R^{2a}$ and $R^{2b}$ can be —$CH_2CH_3$, while the other of $R^{1a}$ and $R^{1b}$ and $R^{2a}$ and $R^{2b}$ can be a $C_{4-20}$ alkyl group.

In various embodiments, the present compounds can have a naphthalene core and be represented by formula Ib:

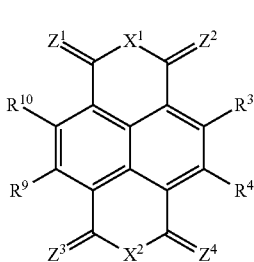

Ib wherein:

$X^1$ and $X^2$ independently can be O, S, or an amine group;

$Z^1$, $Z^2$, $Z^3$, and $Z^4$ independently can be selected from O, S, and Se, provided that at least one of $Z^1$, $Z^2$, $Z^3$, and $Z^4$ is S or Se; and $R^3$, $R^4$, $R^9$, and $R^{10}$ independently can be H or $R^a$, where $R^a$, at each occurrence, independently can be selected from a halogen, —CN, $NO_2$, —$SO_3H$, —$N(R^o)_3^+$, —$COR^o$, —$COOR^o$, and a $C_{1-6}$ haloalkyl group, where $R^o$, at each occurrence, independently can be H or a $C_{1-6}$ alkyl group.

For example, $Z^1$, $Z^2$, $Z^3$, and $Z^4$ can be defined as illustrated by the formulae:

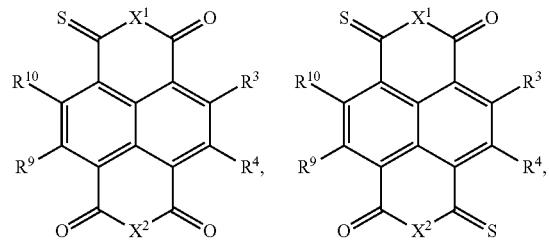

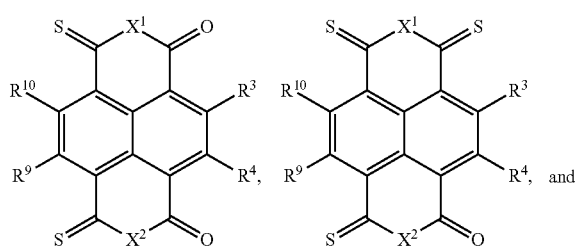

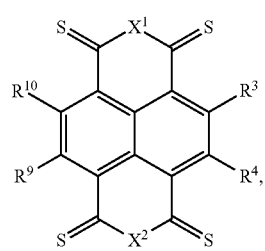

and their Se analogs (i.e., where S atoms are replaced by Se atoms), where $X^1$, $X^2$, $R^3$, $R^4$, $R^9$, and $R^{10}$ are as defined herein. In certain embodiments, $Z^1$ can be S or Se; $Z^2$ can be O; and $Z^3$, and $Z^4$ independently can be selected from O, S, and Se.

To further illustrate, $X^1$ and $X^2$ can be defined as illustrated by the formulae:

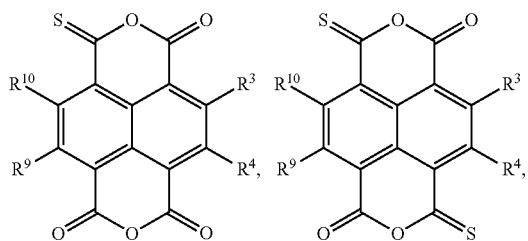

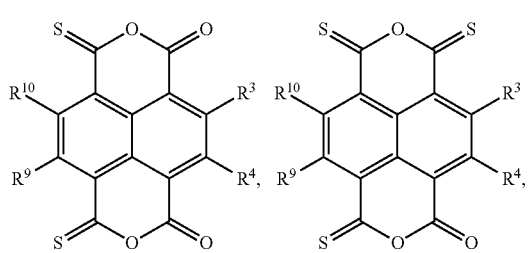

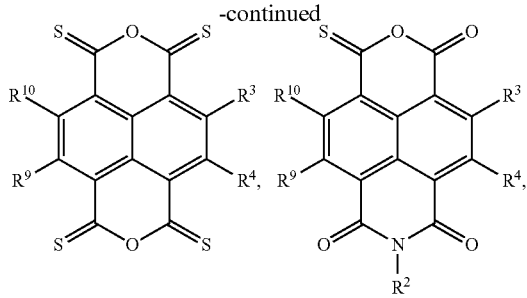

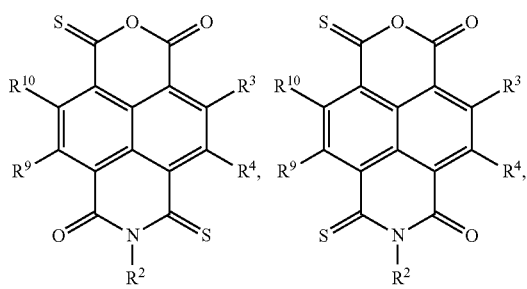

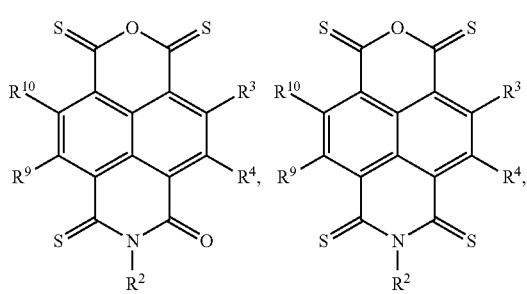

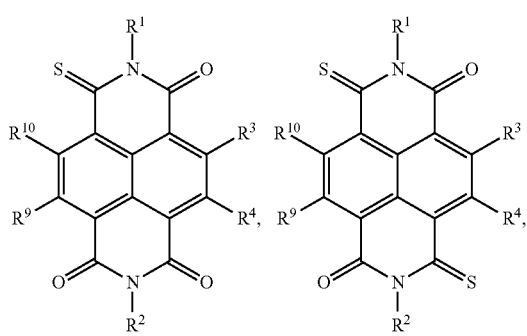

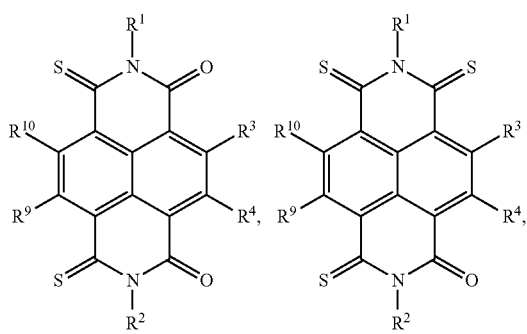

-continued

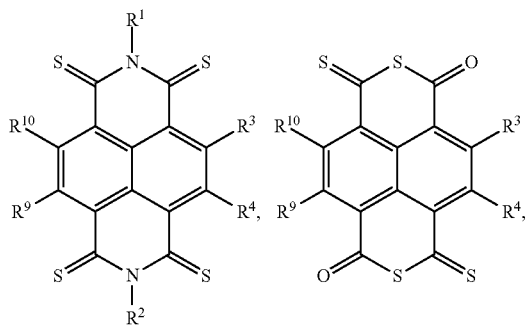

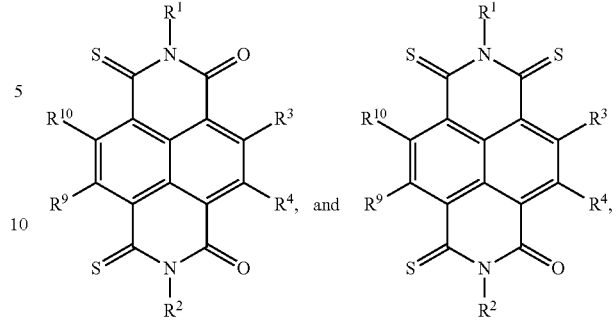

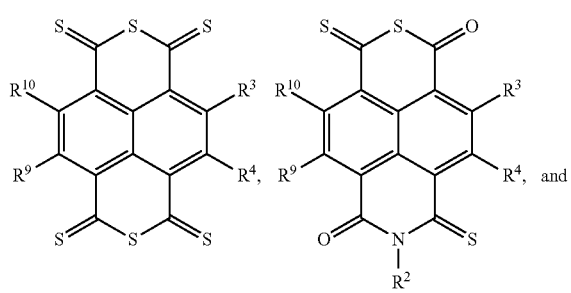

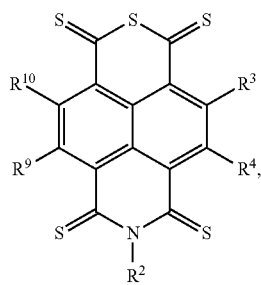

where $R^1$, $R^2$, $R^3$, $R^4$, $R^9$, and $R^{10}$ are as defined herein. In particular embodiments, $R^3$, $R^4$, $R^9$, and $R^{10}$, at each occurrence, independently can be selected from H, F, Cl, Br, and CN.

In certain embodiments, $X^1$ and $X^2$ can be $NR^1$ and $NR^2$, respectively, and compounds according to these embodiments can have a formula selected from:

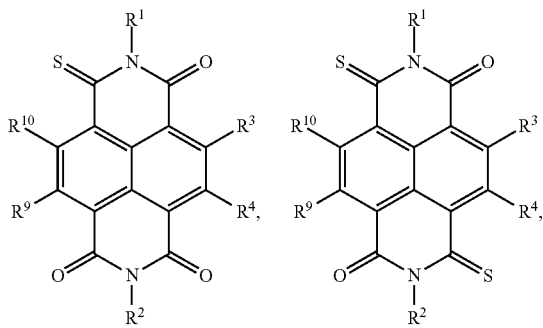

where $R^1$ and $R^2$ can be H or a substituent, and $R^3$, $R^4$, $R^9$, and $R^{10}$ are as described herein. For example, in various embodiments, $R^1$ and $R^2$ independently can be H or a substituent which can impart improved desirable properties to the compound as a whole. For example, certain substituents including one or more electron-withdrawing or electron-donating moieties can modulate the electronic properties of the compound, while substituents that include one or more aliphatic chains can improve the solubility of the compound in organic solvents.

Accordingly, in certain embodiments, $R^1$ and $R^2$ independently can be a $C_{1-40}$ alkyl group, a $C_{2-40}$ alkenyl group, a $C_{2-40}$ alkynyl group, and a $C_{3-40}$ haloalkyl group (e.g., a $C_{3-40}$ alkyl group, a $C_{4-40}$ alkenyl group, a $C_{3-40}$ alkynyl group, and a $C_{3-40}$ haloalkyl group), where each of these groups can be linear or branched, and can be optionally substituted as described herein. For example, $R^1$ and $R^2$ independently can be a $C_{2-40}$ alkenyl or alkynyl group optionally substituted with 1-5 substituents independently selected from a halogen, —CN, $NO_2$, —$SO_3H$, —$N(R^0)_3^+$, —$COR^0$, and —$COOR^0$; or $R^1$ and $R^2$ independently can be a $C_{1-40}$ alkyl or haloalkyl group optionally substituted with 1-5 substituents independently selected from a —CN, $NO_2$, —$SO_3H$, —$N(R^0)_3^+$, —$COR^0$, and —$COOR^0$, where $R^0$, at each occurrence, independently can be H or a $C_{1-40}$ alkyl group. In certain embodiments, $R^1$ and $R^2$ independently can be selected from a $C_{6-40}$ alkyl group, a $C_{6-40}$ alkenyl group, a $C_{6-40}$ alkynyl group, and a $C_{6-40}$ haloalkyl group, each of which can be linear or branched, and can be optionally substituted as described herein. In particular embodiments, $R^1$ and $R^2$ independently can be a $C_{6-40}$ alkyl group, a $C_{6-40}$ alkenyl group, or a $C_{6-40}$ haloalkyl group, which can be either linear or branched, and can be optionally substituted as described herein. For example, $R^1$ and $R^2$ independently can be a branched $C_{3-40}$ alkyl group represented by the formula:

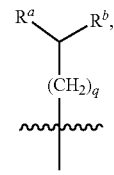

where $R^a$ and $R^b$ independently are a linear or branched $C_{1-20}$ alkyl group, and q is 0, 1, 2, 3, 4, 5, 6, 7, 8, 9 or 10. In certain embodiments, $R^1$ and $R^2$ independently can be a branched $C_{4-40}$ alkenyl group (similar to the branched $C_{3-40}$ alkyl group specified above but with one or more —$CH_2CH_2$— groups replaced by —CH=CH— groups). In certain embodiments, $R^1$ and $R^2$ independently can be a branched $C_{3-40}$ haloalkyl group (similar to the branched $C_{3-40}$ alkyl group specified above but with one or more hydrogen atoms replaced by halogen atoms such as F).

For example, specific examples of $R^1$ and $R^2$ can include linear or branched $C_{1-40}$ alkyl groups and $C_{2-40}$ alkenyl groups such as:

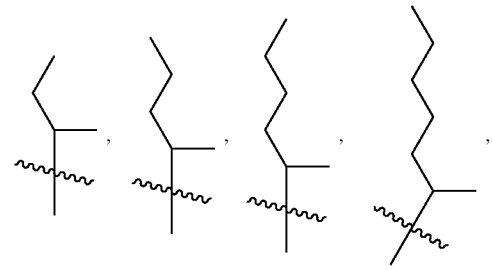

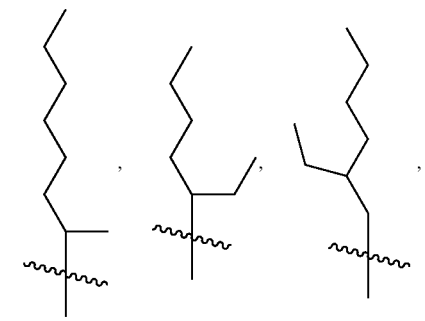

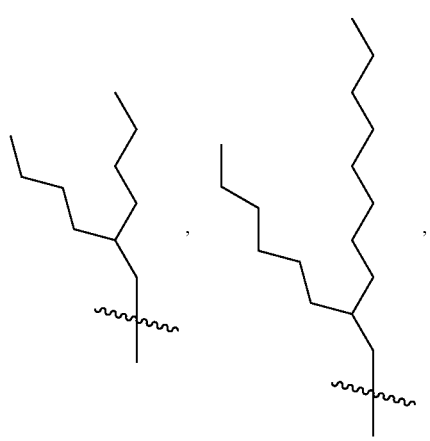

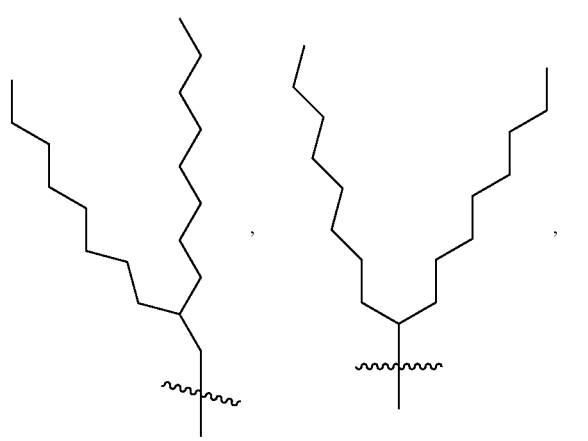

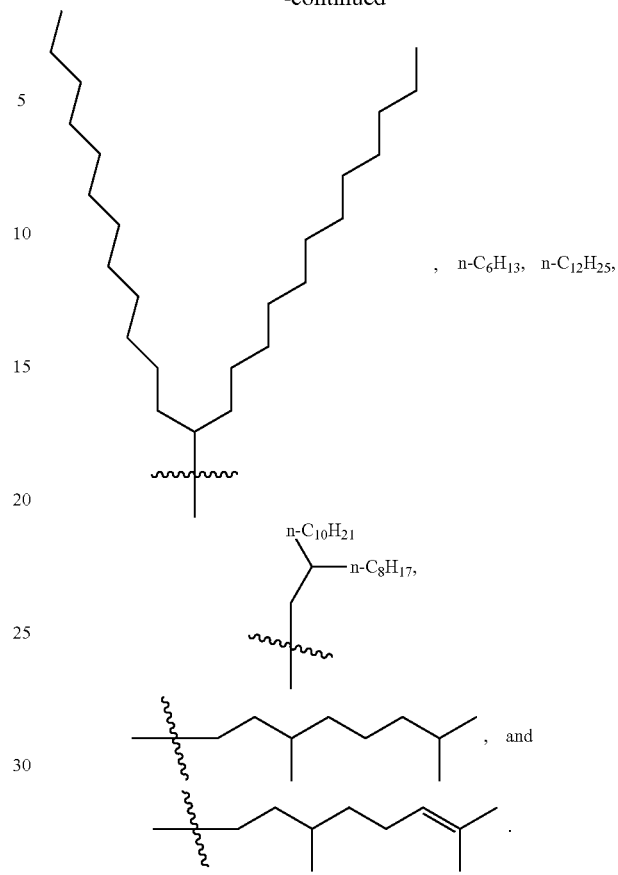

In some embodiments, $R^1$ and $R^2$ independently can be a $C_{3-40}$ cycloalkyl group optionally substituted with 1-5 substituents independently selected from a halogen, —CN, $NO_2$, —$SO_3H$, —$N(R^0)_3^+$, —$COR^0$, —$COOR^0$, a $C_{1-40}$ alkyl group and a $C_{1-40}$ haloalkyl group, where $R^0$, at each occurrence, independently can be H or a $C_{1-40}$ alkyl group. For example, $R^1$ and $R^2$ independently can be an optionally substituted $C_{3-40}$ cycloalkyl group such as:

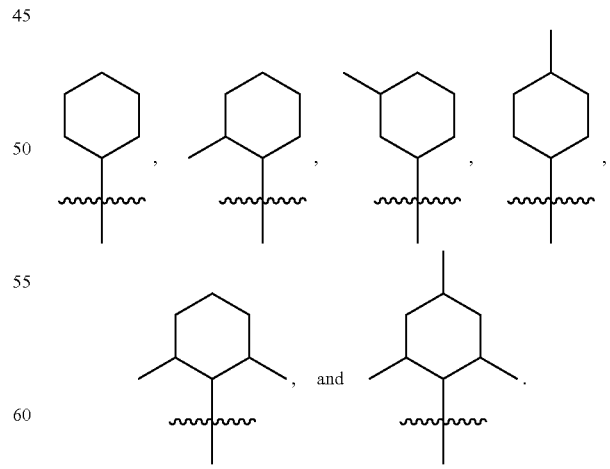

In various embodiments, compounds of formula Ib can have an unsubstituted naphthalene core (i.e., each of $R^3$, $R^4$, $R^9$, and $R^{10}$ is H) or a mono-, di-, tri-, or tetrasubstituted naphthalene core. In some embodiments, the above naphthalene compounds can be disubstituted or tetrasubstituted with F, Cl, Br, or CN. For example, each of $R^3$, $R^4$, $R^9$, and $R^{10}$ independently can be selected from F, Cl, Br, and CN. In certain embodiments, two of $R^3$, $R^4$, $R^9$, and $R^{10}$ can be CN, and the other two of $R^3$, $R^4$, $R^9$, and $R^{10}$ can be selected from F, Cl, and Br. In other embodiments, two of $R^3$, $R^4$, $R^9$, and $R^{10}$ can be H, while the other two of $R^3$, $R^4$, $R^9$, and $R^{10}$ can be selected from F, Cl, Br, and CN. For example, one of $R^3$ and $R^4$ can be H and one of $R^9$ and $R^{10}$ can be H, while the other of $R^3$ and $R^4$ and the other of $R^9$ and $R^{10}$ can be selected from F, Cl, Br, and CN.

In some embodiments, the naphthalene compounds can have an unsubstituted core. Compounds according to these embodiments can be have a formula selected from:

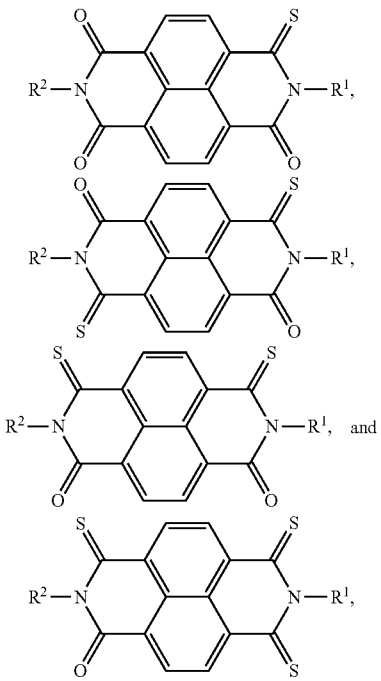

where $R^1$ and $R^2$ can be selected from a linear $C_{1-40}$ alkyl group, a linear $C_{2-40}$ alkenyl group, a linear $C_{1-40}$ haloalkyl group, a branched $C_{3-40}$ alkyl group, a branched $C_{4-40}$ alkenyl group, and a branched $C_{3-40}$ haloalkyl group, each of which can be optionally substituted as described herein.

In some embodiments, the naphthalene compounds can have a disubstituted core and be thionated in the trans positions (i.e., $Z^1=Z^4=S$ and $Z^2=Z^3=O$). Compounds according to these embodiments can be have a formula selected from:

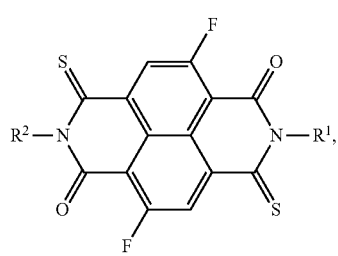

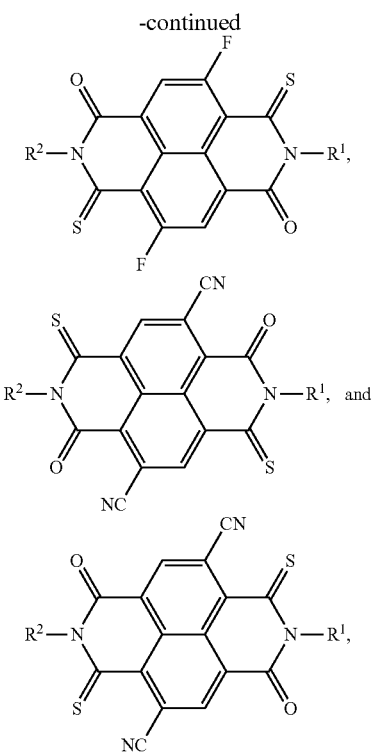

where $R^1$ and $R^2$ can be selected from a linear $C_{1-40}$ alkyl group, a linear $C_{2-40}$ alkenyl group, a linear $C_{1-40}$ haloalkyl group, a branched $C_{3-40}$ alkyl group, a branched $C_{4-40}$ alkenyl group, and a branched $C_{3-40}$ haloalkyl group, each of which can be optionally substituted as described herein.

In various embodiments, the present compounds can be represented by the formula Ic:

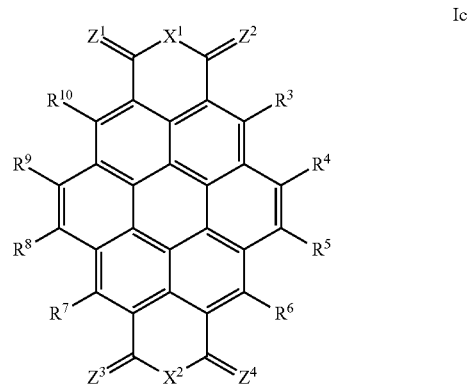

wherein:
$X^1$ and $X^2$ independently can be O, S, or an amine group (i.e., $NR^1$ and $NR^2$, respectively);
$Z^1$, $Z^2$, $Z^3$, and $Z^4$ independently can be selected from O, S, and Se, provided that at least one of $Z^1$, $Z^2$, $Z^3$, and $Z^4$ is S or Se; and
$R^1$, $R^2$, $R^3$, $R^4$, $R^5$, $R^6$, $R^7$, $R^8$, $R^9$, and $R^{10}$ are as defined herein.

In some embodiments, compounds of formula Ic can have an unsubstituted coronene core (i.e., each of $R^3$, $R^4$, $R^5$, $R^6$, $R^7$, $R^8$, $R^9$, and $R^{10}$ is H) or a mono-, di-, tri-, or tetrasubstituted coronene core. In some embodiments, the above coronene compounds can be disubstituted or tetrasubstituted with F, Cl, Br, or CN. For example, each of $R^4$, $R^5$, $R^8$, and $R^9$ independently can be selected from F, Cl, Br, and CN. In certain embodiments, two of $R^4$, $R^5$, $R^8$, and $R^9$ can be CN, and the other two of $R^4$, $R^5$, $R^8$, and $R^9$ can be selected from F, Cl, and Br. In other embodiments, two of $R^4$, $R^5$, $R^8$, and $R^9$ can be H, while the other two of $R^4$, $R^5$, $R^8$, and $R^9$ can be selected from F, Cl, Br, and CN. For example, one of $R^4$ and $R^5$ can be H and one of $R^8$ and $R^9$ can be H, while the other of $R^4$ and $R^5$ and the other of $R^8$ and $R^9$ can be selected from F, Cl, Br, and CN.

In certain embodiments, compounds of formula Ic can be represented by a formula selected from:

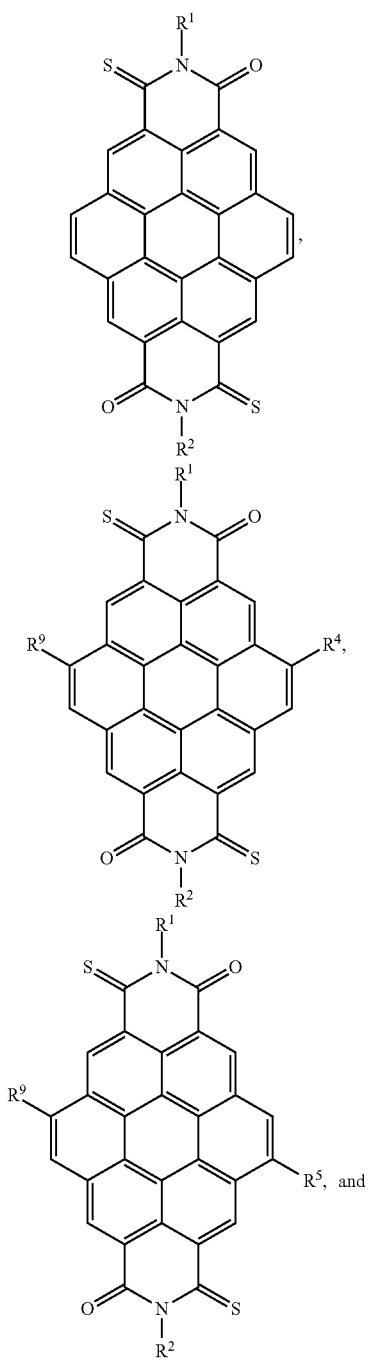

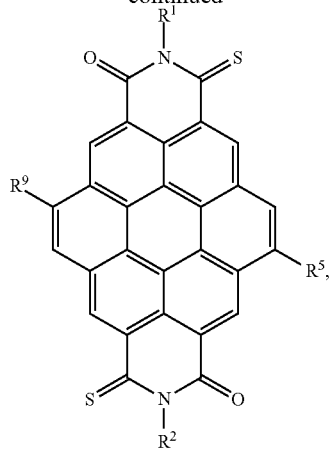

where $R^1$ and $R^2$ can be selected from a linear $C_{1-40}$ alkyl group, a linear $C_{2-40}$ alkenyl group, a linear $C_{1-40}$ haloalkyl group, a branched $C_{3-40}$ alkyl group, a branched $C_{4-40}$ alkenyl group, and a branched $C_{3-40}$ haloalkyl group, each of which can be optionally substituted as described herein; and each of $R^4$, $R^5$ and $R^9$ can be an electron-withdrawing group independently selected from F, Cl, Br, I, CN, $CF_3$, $CH_2CF_3$ and $CF_2CF_3$.

Although as described herein, the core of the present compounds in most embodiments is either unsubstituted or optionally substituted with one or more electron-withdrawing groups, the present teachings also encompass coronene compounds where the core of these compounds can be substituted with one or more electron-donating groups. For example, certain compounds of the present teachings can be represented by the formula:

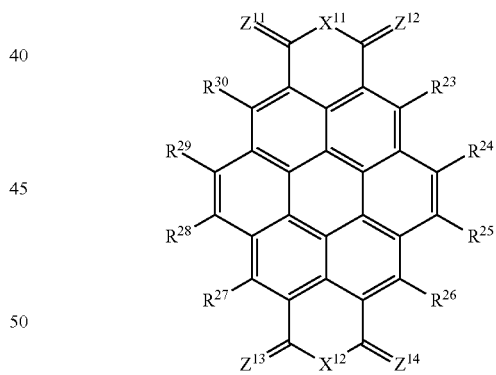

wherein:
$X^{11}$ and $X^{12}$ independently can be O, S, or an amine group (i.e., $NR^1$ and $NR^2$, respectively);
$Z^{11}$, $Z^{12}$, $Z^{13}$, and $Z^{14}$ independently can be selected from O, S, and Se, provided that at least one of $Z^{11}$, $Z^{12}$, $Z^{13}$ and $Z^{14}$ is S or Se;
$R^{23}$, $R^{24}$, $R^{25}$, $R^{26}$, $R^{27}$, $R^{28}$, $R^{29}$, and $R^{30}$ can be H or an electron-donating group such as a $C_{1-40}$ alkyl group, a $C_{2-40}$ alkenyl group, a $C_{2-40}$ alkynyl groups, or a $C_{1-40}$ alkoxy group, provided that at least one of $R^{23}$, $R^{24}$, $R^{25}$, $R^{26}$, $R^{27}$, $R^{28}$, $R^{29}$, and $R^{30}$ is an electron-donating group; and
$R^1$ and $R^2$ are as defined herein.

For example, certain compounds of the present teachings can be represented by the formula:

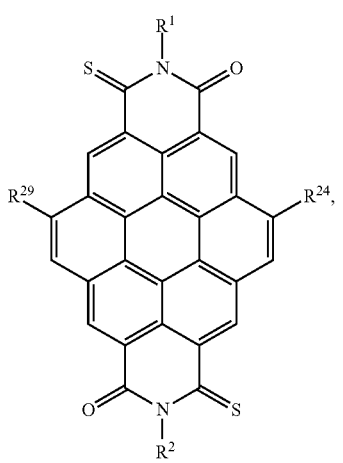

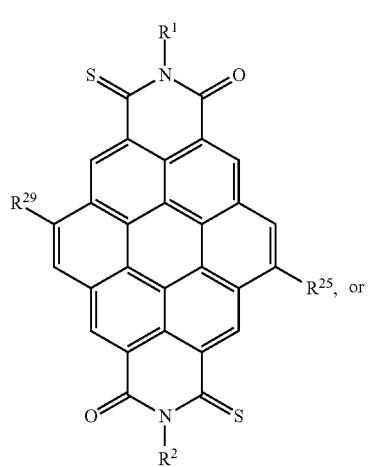

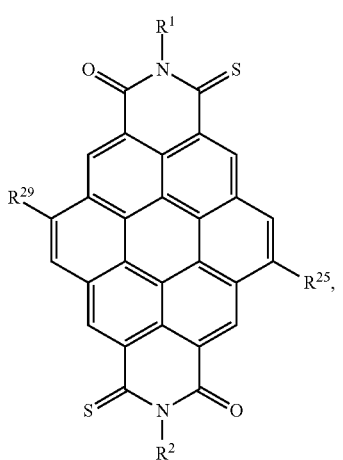

where $R^1$ and $R^2$ can be selected from a linear $C_{1-40}$ alkyl group, a linear $C_{2-40}$ alkenyl group, a linear $C_{1-40}$ haloalkyl group, a branched $C_{3-40}$ alkyl group, a branched $C_{4-40}$ alkenyl group, and a branched $C_{3-40}$ haloalkyl group, each of which can be optionally substituted as described herein; and each of $R^4$, $R^5$ and $R^9$ can be an electron-donating group selected from a $C_{1-40}$ alkyl group, a $C_{2-40}$ alkenyl group, a $C_{2-40}$ alkynyl groups, and a $C_{1-40}$ alkoxy group.

Illustrative compounds of formula I (including formulae Ia, Ib, and Ic) include:

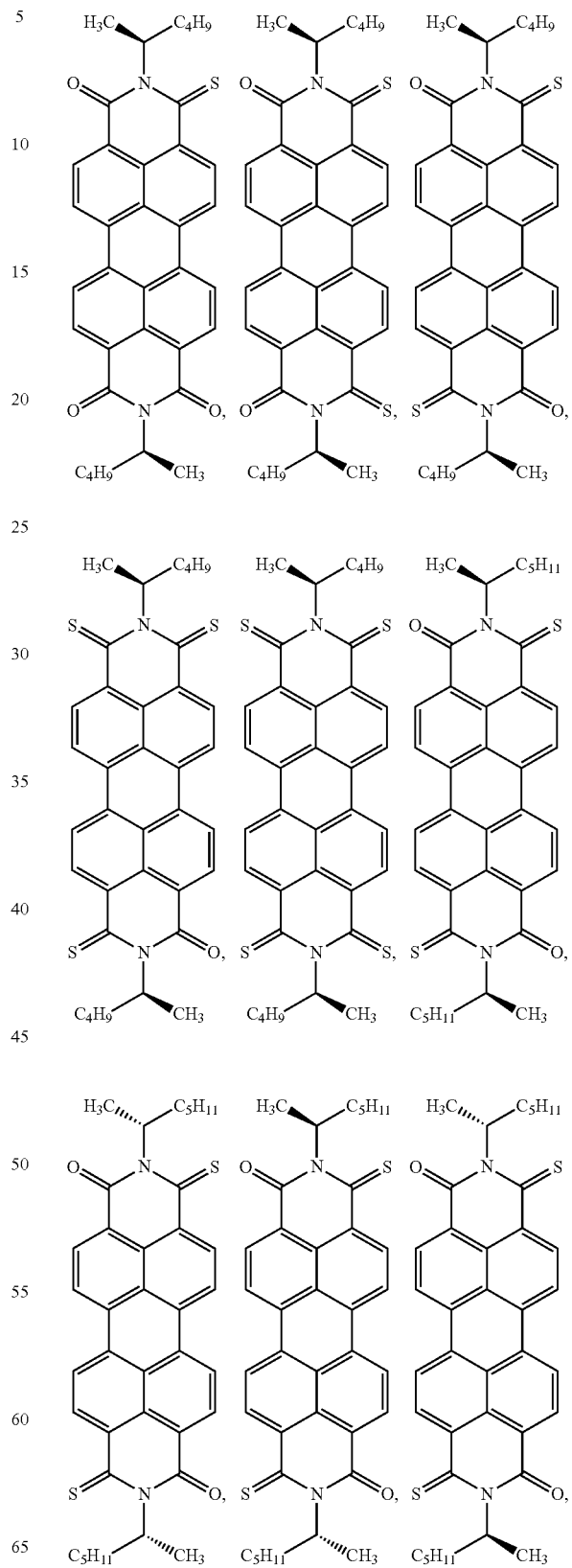

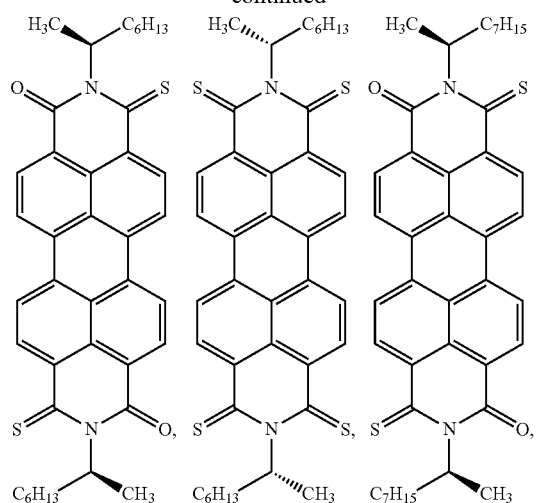
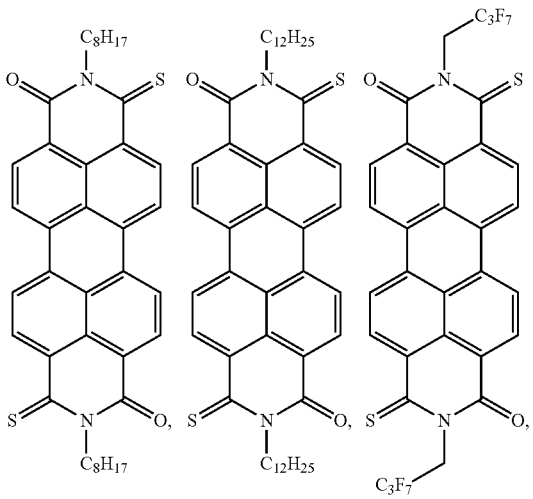
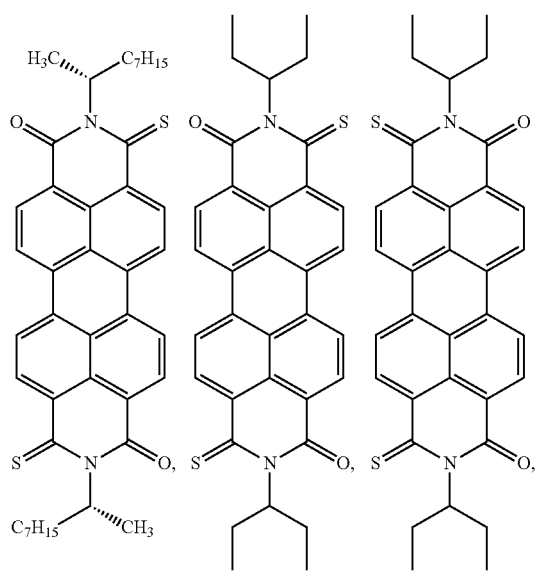
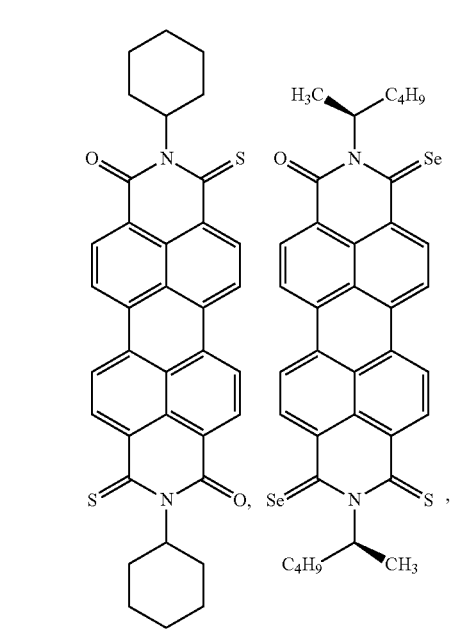
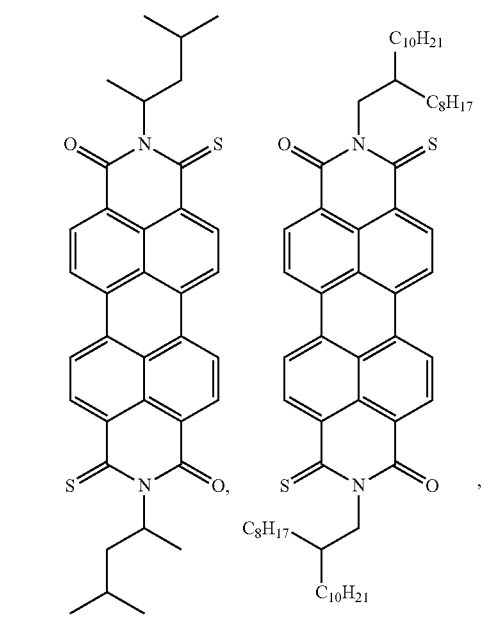
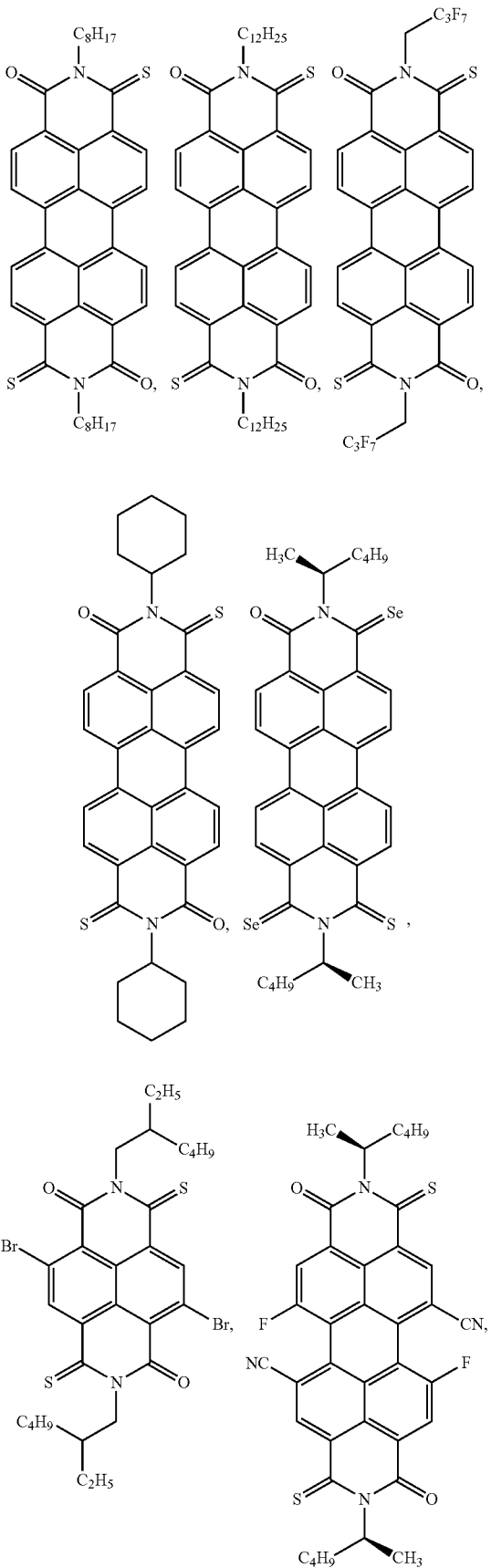

47
-continued
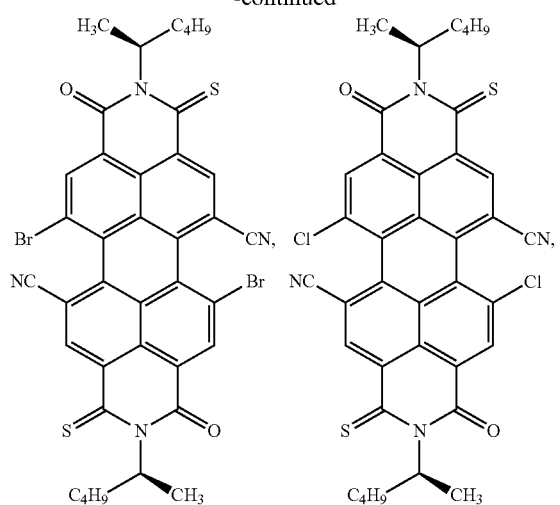
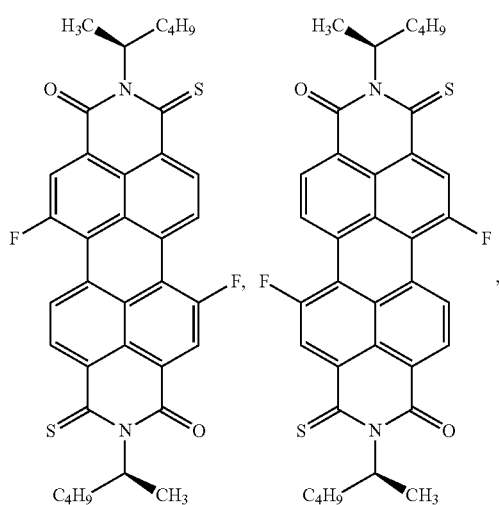
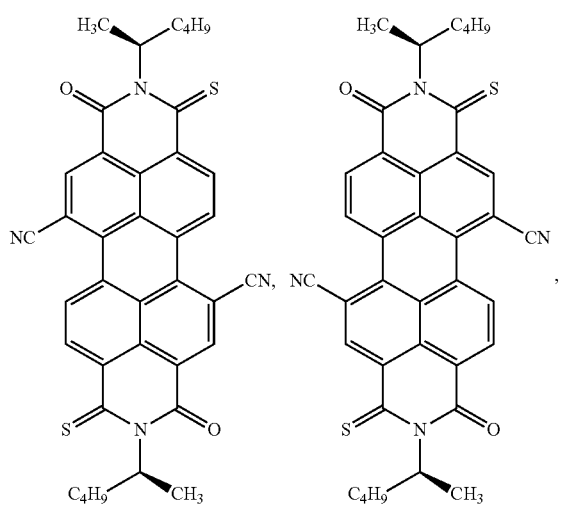
48
-continued
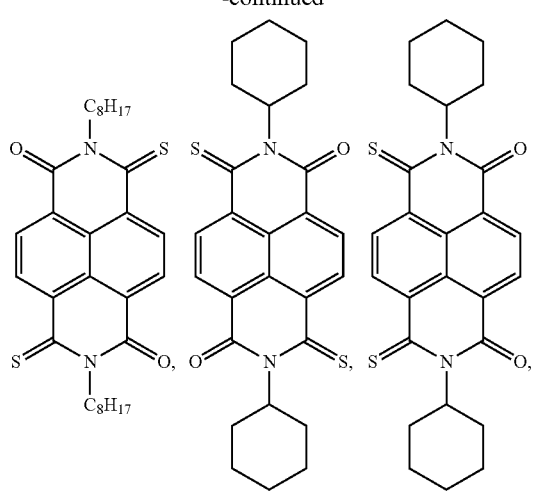
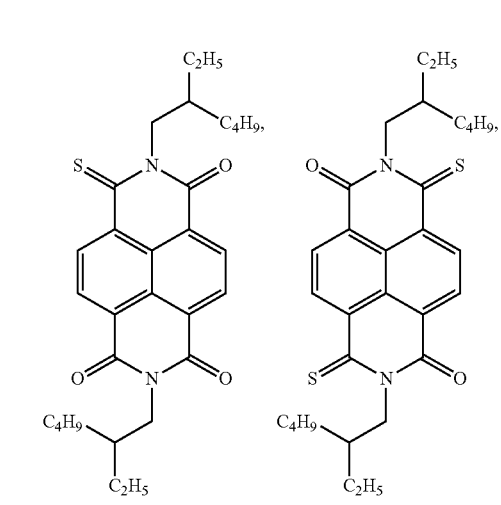
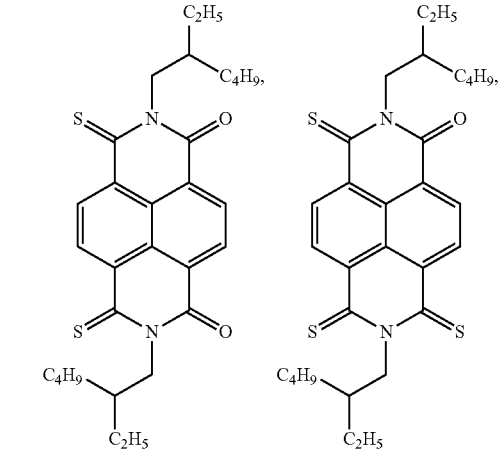

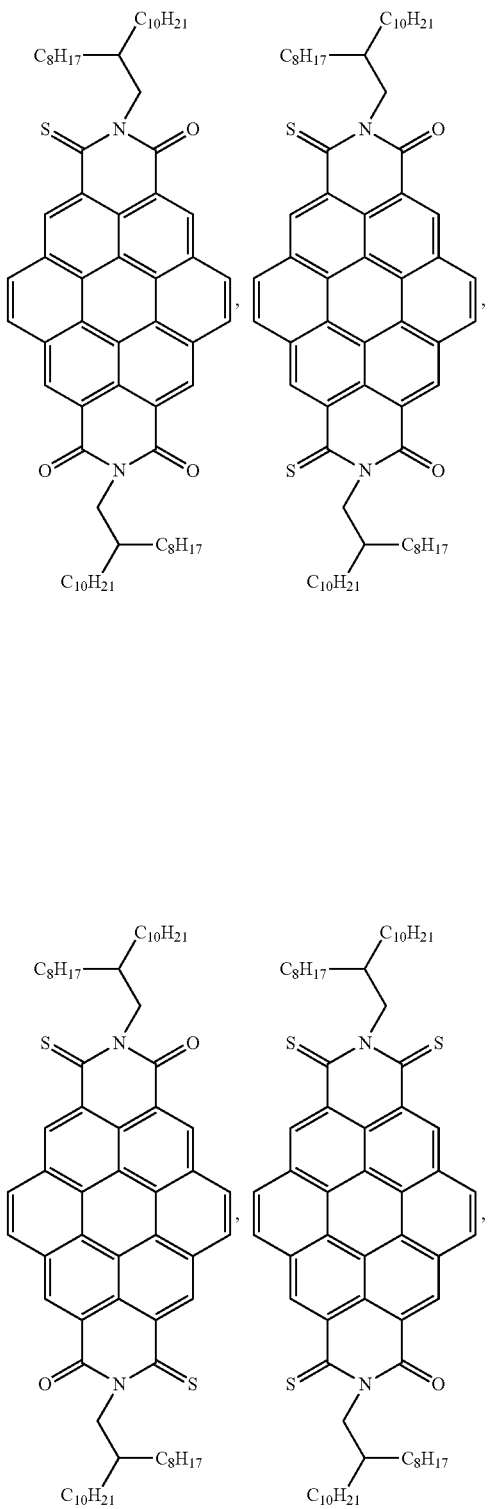

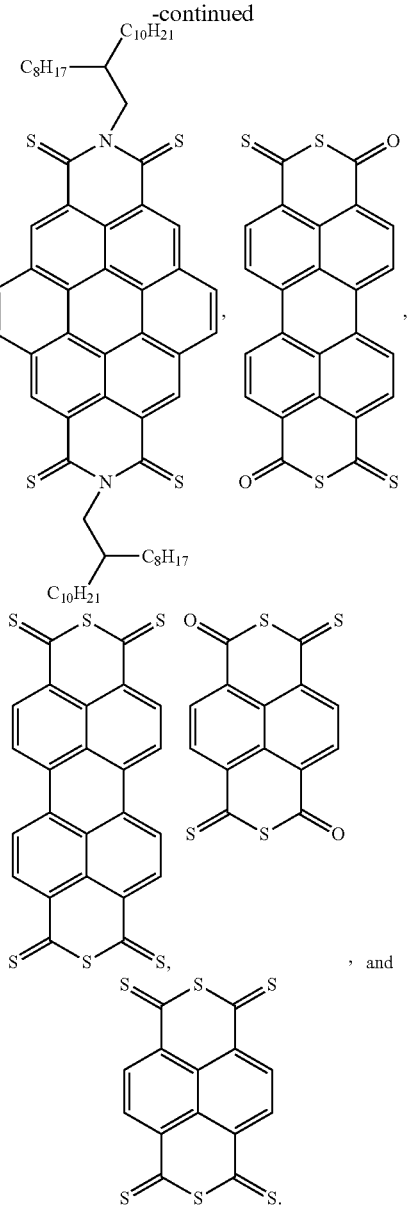

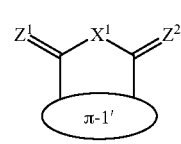

In another aspect, the present teachings relate to compounds of formula II:

$$\begin{array}{c} Z^1 = X^1 = Z^2 \\ \pi\text{-}1' \end{array} \quad \text{II}$$

wherein:
X$^1$ can be selected from O, S, and an amine group;
Z$^1$ and Z$^2$ independently can be selected from O, S, and Se, provided that at least one of Z$^1$ and Z$^2$ is S or Se; and
π'-1 can be a fused ring moiety optionally substituted with 1-4 electron-withdrawing groups.

For example, the optionally substituted fused ring moiety comprising π'-1 can be an optionally substituted naphthalene moiety or an optionally substituted perylene moiety. In some embodiments, compounds of formula II can have the formula:

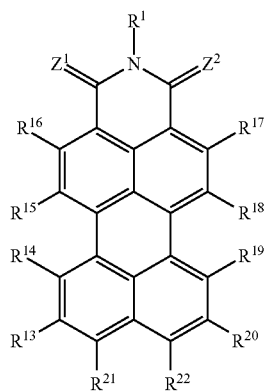

wherein:

$R^1$ is as defined herein;

$R^{13}$, $R^{14}$, $R^{15}$, $R^{16}$, $R^{17}$, $R^{18}$, $R^{19}$, $R^{20}$, $R^{21}$, and $R^{22}$ independently can be selected from H or $R^a$, where $R^a$ is an electron-withdrawing group as defined herein; and $Z^1$ and $Z^2$ are as defined herein.

In particular embodiments, compounds of formula II can have the formula:

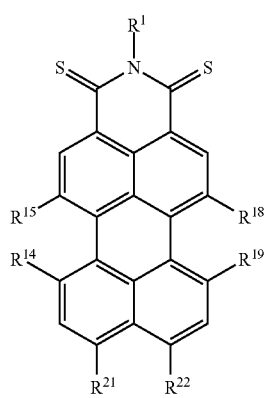

wherein $R^1$ can be selected from a linear $C_{1-40}$ alkyl group, a linear $C_{2-40}$ alkenyl group, a linear $C_{1-40}$ haloalkyl group, a branched $C_{3-40}$ alkyl group, a branched $C_{4-40}$ alkenyl group, and a branched $C_{3-40}$ haloalkyl group, each of which can be optionally substituted as described herein; and $R^{14}$, $R^{15}$, $R^{18}$, $R^{19}$, $R^{21}$, and $R^{22}$ independently can be selected from H, F, Cl, Br, and CN.

By way of example, compounds according to the present teachings can be prepared in accordance with the procedures outlined in Scheme 1 below.

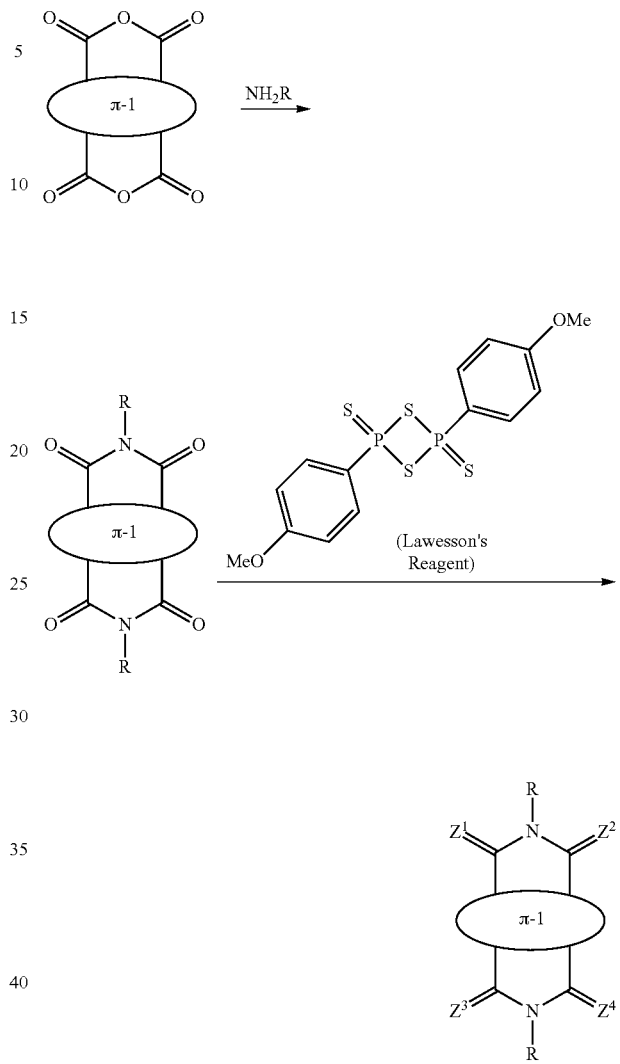

Referring to Scheme 1 above, a tetracarboxylic diimide can be reacted with a Lawesson's reagent to provide various compounds of formula I. For example, a perylene tetracarboxylic diimide (PDI) can be obtained initially by amination of the corresponding anhydride, then reacted with the Lawesson's reagent. Compounds of formula II can be prepared analogously starting from an appropriate dicarboxylic imide. In addition, other 1,3,2,4-dithiadiphosphetane 2,4-disulfides can be used in place of the Lawesson's reagent. For example, the Davy reagent, which has —S—$CH_3$ groups instead of the p-methoxyphenyl groups in the Lawesson's reagent, phosphorous pentasulfide, hexamethyl disilthiane, thiophosphoryl chloride, or elemental sulfur ($S_8$) can be used instead.

Coronene compounds according to formula Ic can be prepared in accordance with the procedures outlined in Scheme 2 below. In the illustrated scheme, each of $R^1$ and $R^2$ is a 2-octyldodecyl group, and each of $R^3$, $R^4$, $R^5$, $R^6$, $R^7$, $R^8$, $R^9$, and $R^{10}$ is H.

Scheme 2
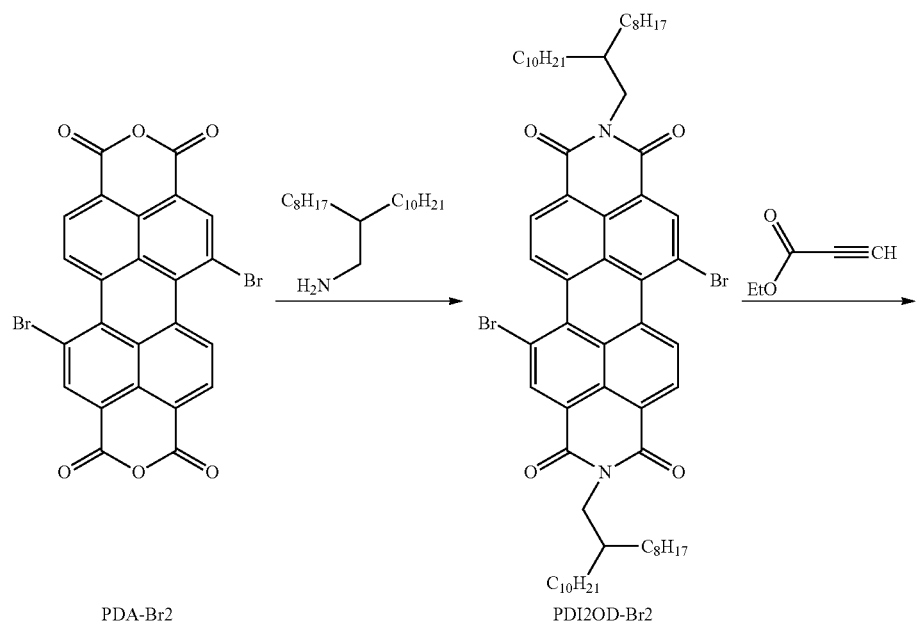
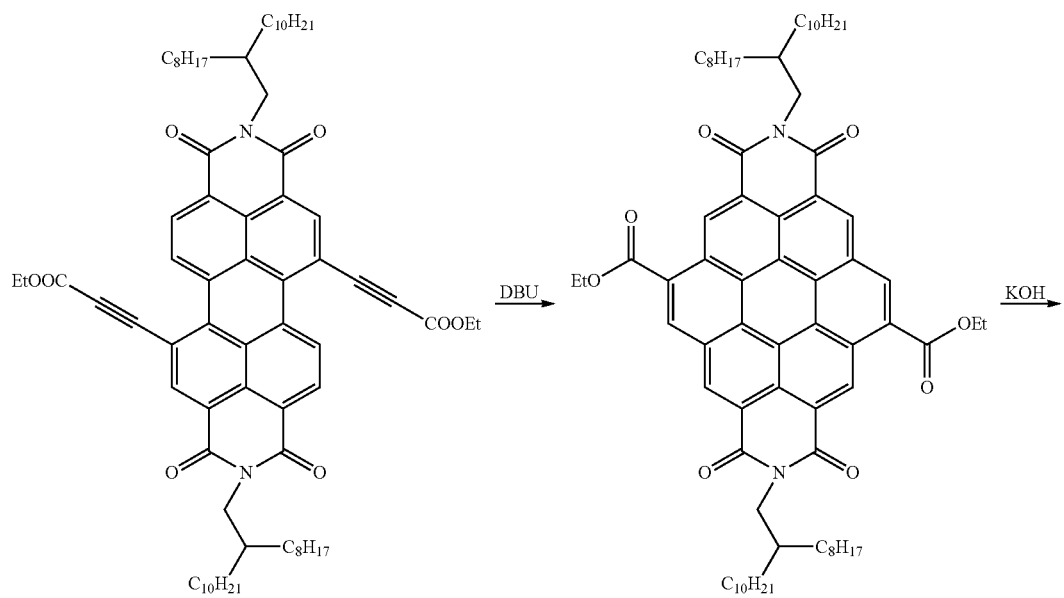

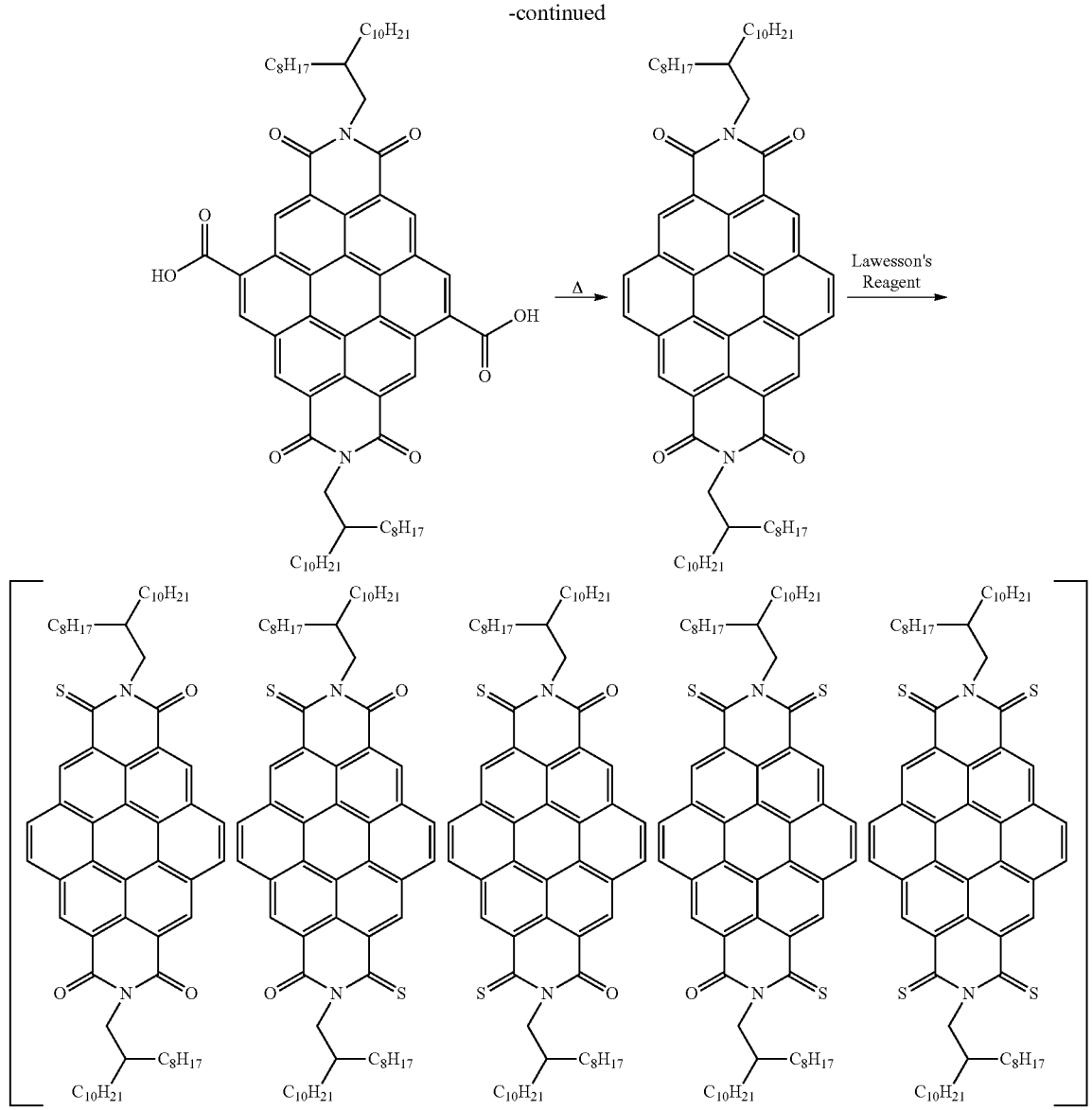

As shown, a brominated perylene tetracarboxylic dianhydride (PDA-Br$_2$) can be first reacted with an appropriate amine to provide the desired R$^1$ and R$^2$ groups (here, 2-octyldodecyl groups). Intramolecular diels-alders cycloaddition can be achieved by reacting the resulting diimide (PDI2OD-Br$_2$) with ethyl propiolate, then 1,8-diazabicyclo[5.4.0]undec-7-ene (DBU). Reaction with a base such as potassium hydroxide (KOH) followed by heating leads to removal of the ethyl acetate groups.

Alternatively, the present compounds can be prepared from commercially available starting materials, compounds known in the literature, or via other readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (NMR, e.g., $^1$H or $^{13}$C), infrared spectroscopy (IR), spectrophotometry (e.g., UV-visible), mass spectrometry (MS), or by chromatography such as high pressure liquid chromatography (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

In some embodiments, the present teachings can include isolating the trans isomers (where $Z^1=Z^4=S$ and $Z^2=Z^3=O$) from the cis and trans racemic mixture using separation methods known by those skilled in the art. For example, the trans isomers can be isolated by fractional crystallization of a salt, silica gel column chromatography, and/or separation by other chromatography techniques such as thin layer chromatography, flash chromatography, and high pressure liquid chromatography. Examples of useful solvents for carrying out such separation methods include toluene, methylene chloride, chloroform, acetone, and various hydrocarbons.

Certain embodiments disclosed herein can be stable in ambient conditions ("ambient stable") and soluble in common solvents. As used herein, a compound can be considered electrically "ambient stable" or "stable at ambient conditions" when a transistor (e.g., organic thin film transistor, OTFT) incorporating the compound as its semiconducting material exhibits a carrier mobility that is maintained at about its initial measurement when the compound is exposed to ambient conditions, for example, air, ambient temperature, and humidity, over a period of time. For example, a compound according to the present teachings can be described as ambient stable if a transistor incorporating the compound shows a carrier mobility that does not vary more than 20% or more than 10% from its initial value after exposure to ambient conditions, including, air, humidity and temperature, over a 3 day, 5 day, or 10 day period. In addition, a compound can be considered ambient stable if the optical absorption of the corresponding film does not vary more than 20% (preferably, does not vary more than 10%) from its initial value after exposure to ambient conditions, including air, humidity and temperature, over a 3 day, 5 day, or 10 day period.

As used herein, a compound can be considered soluble in a solvent when at least 0.1 mg of the compound can be dissolved in 1 mL of the solvent. Examples of common organic solvents include petroleum ethers; acetonitrile; aromatic hydrocarbons such as benzene, toluene, xylene, mesitylene, and 1-methylnaphthalene; ketones such as acetone, and methyl ethyl ketone; ethers such as tetrahydrofuran, dioxane, bis(2-methoxyethyl)ether, diethyl ether, di-isopropyl ether, and t-butyl methyl ether; alcohols such as methanol, ethanol, butanol, and isopropyl alcohol; aliphatic hydrocarbons such as hexanes; esters such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone. In various embodiments, the present compounds can have good solubility in solvents that are aromatic hydrocarbons such as benzene, toluene, xylene, mesitylene, and 1-methylnaphthalene.

OTFTs based on the present compounds can have long-term operability and continued high-performance in ambient conditions. For example, OTFTs based on certain embodiments of the present compounds can maintain satisfactory device performance in highly humid environment. Certain embodiments of the present compounds also can exhibit excellent thermal stability over a wide range of annealing temperatures. Photovoltaic devices can maintain satisfactory power conversion efficiencies over an extended period of time.

The present compounds can be fabricated into various articles of manufacture using solution processing techniques in addition to other more expensive processes such as vapor deposition. Various solution processing techniques have been used with organic electronics. Common solution processing techniques include, for example, spin coating, drop-casting, zone casting, dip coating, blade coating, or spraying. Another example of solution processing technique is printing. As used herein, "printing" includes a noncontact process such as inkjet printing, microdispensing and the like, and a contact process such as screen-printing, gravure printing, offset printing, flexographic printing, lithographic printing, pad printing, microcontact printing and the like.

Compounds of the present teachings can be used alone or in combination with other compounds to prepare semiconductor materials (e.g., compositions and composites), which in turn can be used to fabricate various articles of manufacture, structures, and devices. In some embodiments, semiconductor materials incorporating one or more compounds of the present teachings can exhibit n-type semiconductor activity, p-type semiconductor activity, ambipolar activity, light absorption, and/or light emission.

The present teachings, therefore, further provide methods of preparing a semiconductor material. The methods can include preparing a composition that includes one or more compounds disclosed herein dissolved or dispersed in a liquid medium such as a solvent or a mixture of solvents, depositing the composition on a substrate to provide a semiconductor material precursor, and processing (e.g., heating) the semiconductor precursor to provide a semiconductor material (e.g., in the form of a thin film or thin film semiconductor) that includes a compound disclosed herein. In various embodiments, the liquid medium can be an organic solvent, an inorganic solvent such as water, or combinations thereof. In some embodiments, the composition can further include one or more additives independently selected from viscosity modulators, detergents, dispersants, binding agents, compatiblizing agents, curing agents, initiators, humectants, antifoaming agents, wetting agents, pH modifiers, biocides, and bacteriostats. For example, surfactants and/or polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying.

Various articles of manufacture including electronic devices, optical devices, and optoelectronic devices, such as organic thin film semiconductors, organic field effect transistors (OFETs) (e.g., organic thin film transistors (OTFTs)), organic photovoltaics (OPVs), organic light emitting devices such as organic light emitting diodes (OLEDs) and organic light emitting transistors (OLETs), photodetectors, complementary metal oxide semiconductors (CMOSs), complementary inverters, diodes, capacitors, sensors, D flip-flops, rectifiers, and ring oscillators, that make use of the compounds disclosed herein are within the scope of the present teachings as are methods of making the same. The present compounds can offer processing and operation advantages in the fabrication and/or the use of these devices.

For example, articles of manufacture such as the various devices described herein can include a composite having a semiconductor material of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), and self-assembled superlattice/self-assembled nanodielectric (SAS/SAND) materials (e.g., as described in Yoon, M-H. et al., *PNAS,* 102 (13): 4678-4682 (2005), the entire disclosure of which is incorporated by reference herein), as well as hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)). One or more of the composites described herein can be embodied within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Accordingly, an aspect of the present teachings relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures.

FIGS. 1*a-d* illustrates the four common types of OFET structures: (FIG. 1*a*) bottom-gate top-contact structure 1a, (FIG. 1*b*) bottom-gate bottom-contact structure 1b, (FIG. 1*c*) top-gate bottom-contact structure 1c, and (FIG. 1*d*) top-gate top-contact structure 1d. As shown in FIGS. 1*a-d*, an OFET can include a dielectric layer (e.g., shown as 8, 8', 8", and 8'''), a semiconductor layer (e.g., shown as 6, 6', 6", and 6'''), a gate contact (e.g., shown as 10, 10', 10", and 10'''), a substrate (e.g., shown as 12, 12', 12", and 12'''), and source and drain contacts (e.g., shown as 2, 2', 2", 2''', 4, 4', 4", and 4''').

In certain embodiments, OTFT devices can be fabricated with the present compounds on doped silicon substrates, using $SiO_2$ as the dielectric, in top-contact geometries. In particular embodiments, the active semiconductor layer which incorporates at least a compound of the present teachings can be deposited at room temperature or at an elevated temperature. In other embodiments, the active semiconductor layer which incorporates at least one compound of the present teachings can be applied by spin-coating or printing as described herein. For top-contact devices, metallic contacts can be patterned on top of the films using shadow masks.

In certain embodiments, OTFT devices can be fabricated with the present compounds on plastic foils, using polymers as the dielectric, in top-gate bottom-contact geometries. In particular embodiments, the active semiconducting layer which incorporates at least a compound of the present teachings can be deposited at room temperature or at an elevated temperature. In other embodiments, the active semiconducting layer which incorporates at least a compound of the present teachings can be applied by spin-coating or printing as described herein. Gate and source/drain contacts can be made of Au, other metals, or conducting polymers and deposited by vapor-deposition and/or printing.

Other articles of manufacture in which compounds of the present teachings are useful include photovoltaics or solar cells. Compounds of the present teachings can exhibit broad optical absorption and/or a tuned redox properties and bulk carrier mobilities, making them desirable for such applications. Accordingly, the compounds described herein can be used as an acceptor (n-type) semiconductor or a donor (p-type) semiconductor in a photovoltaic design, which includes an adjacent p-type or n-type semiconductor material, respectively, that forms a p-n junction. The compounds can be in the form of a thin film semiconductor, which can be deposited on a substrate to form a composite. Exploitation of compounds of the present teachings in such devices is within the knowledge of a skilled artisan.

Figure 2:
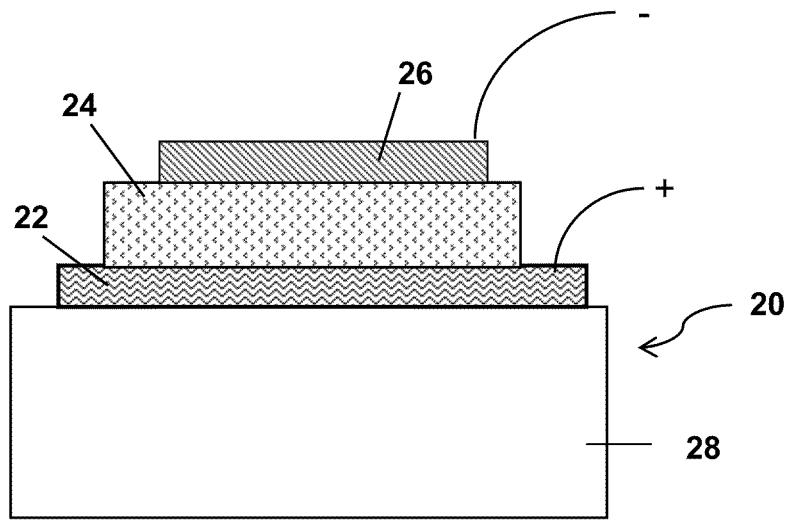
FIG. 2 illustrates a representative structure of a bulk-heterojunction organic photovoltaic device (also known as solar cell) which can incorporate one or more compounds of the present teachings as the donor and/or acceptor materials.
Figure 3:
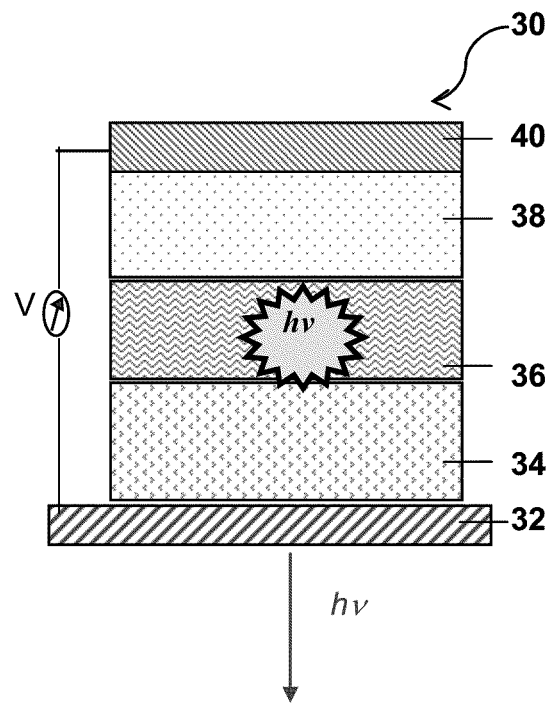
FIG. 3 illustrates a representative structure of an organic light-emitting device which can incorporate one or more compounds of the present teachings as electron-transporting and/or emissive and/or hole-transporting materials.
Figure 4:
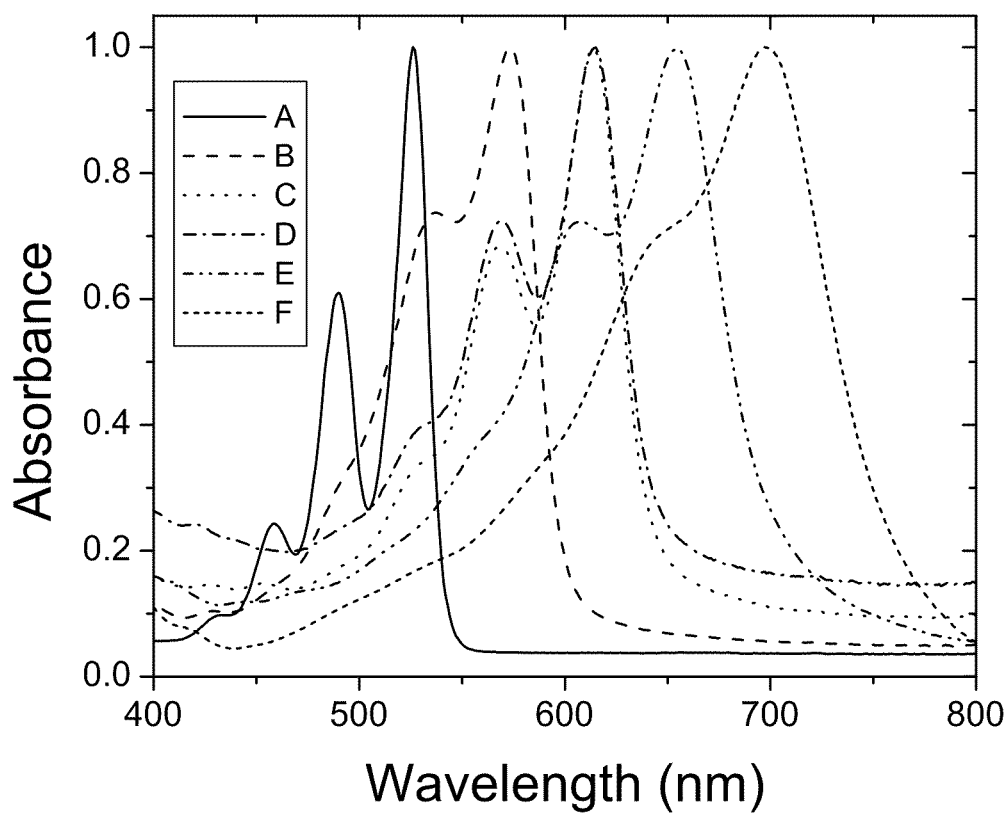
FIG. 4 shows the optical absorbance spectra of (S,S)—PDI1MP (A), (S,S)—PDIS$_1$1MP (B), (S,S)-trans-PDIS$_2$1MP (C), (S,S)-cis-PDIS$_2$1MP (D), (S,S)—PDIS$_3$1MP (E), and (S,S)—PDIS$_4$1MP (F) in chloroform solution.
Figure 5:
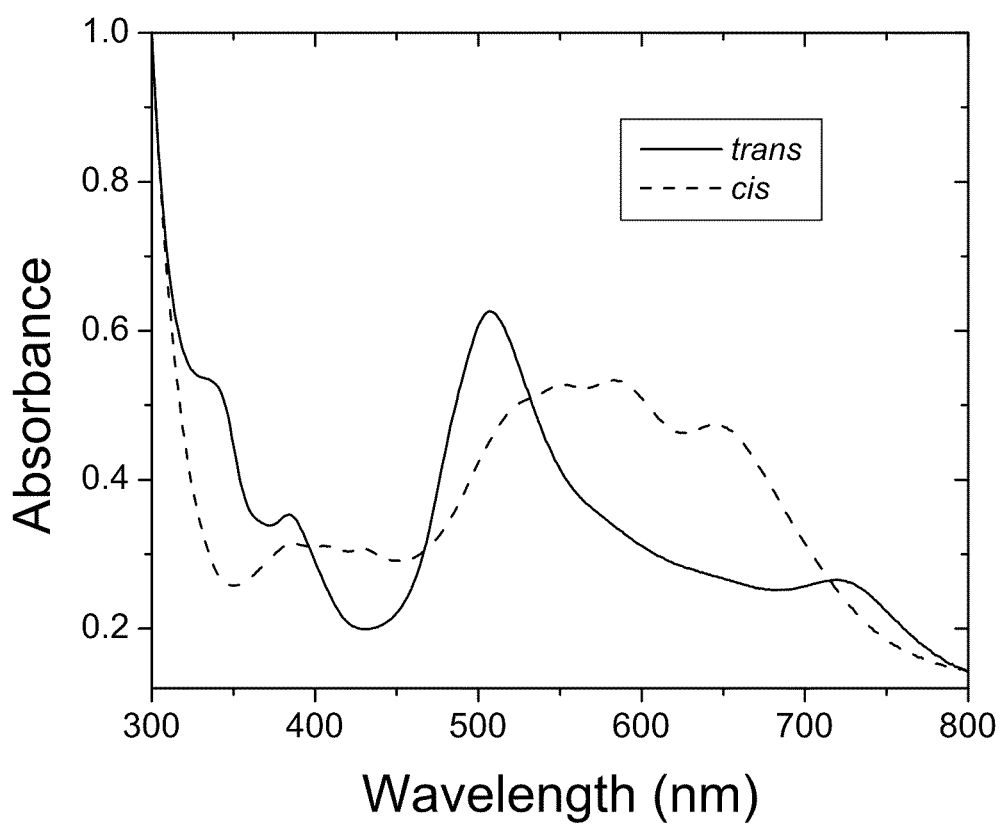
FIG. 5 shows the optical absorbance spectra of (S,S)-trans-PDIS$_2$1MP and cis-PDIS$_2$1MP as thin films.
Figure 6:
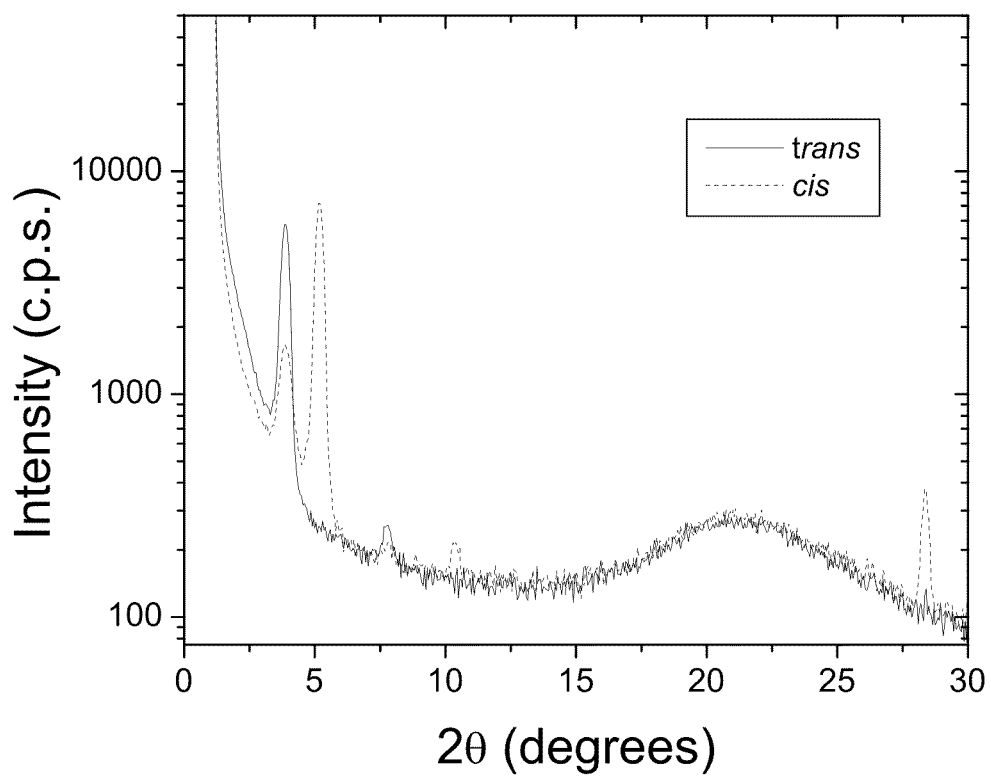
FIG. 6 shows the X-ray diffraction data of (S,S)-trans-PDIS$_2$1MP and cis-PDIS$_2$1MP as thin films.
Figure 7:
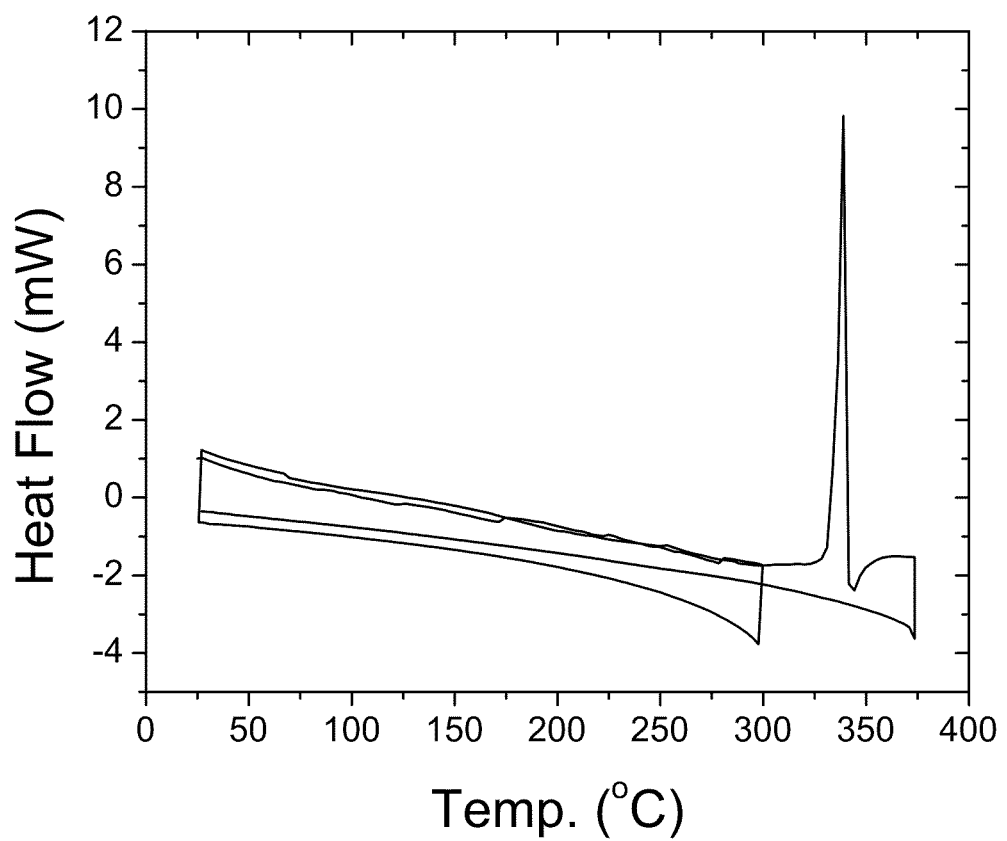
FIG. 7 shows the DSC thermograms of (S,S)-trans-PDIS$_2$1MP ($10°$ C. min$^{-1}$).
Figure 8:
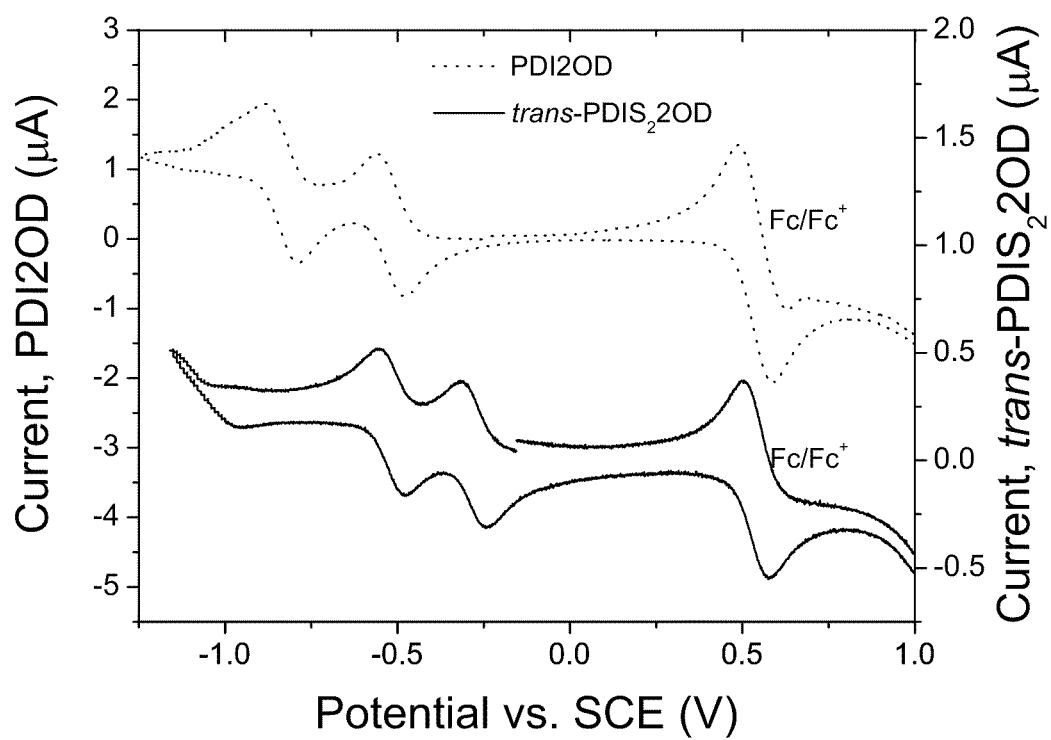
FIG. 8 shows the cyclic voltammograms of PDI2OD and trans-PDIS$_2$2OD (in THF, scan rate 20 mV s$^{-1}$). Working and counter electrodes were Pt and the reference electrode was Ag/Ag$^+$. The electrolyte was Bu$_4$NPF$_6$ (0.1 M).
Figure 9:
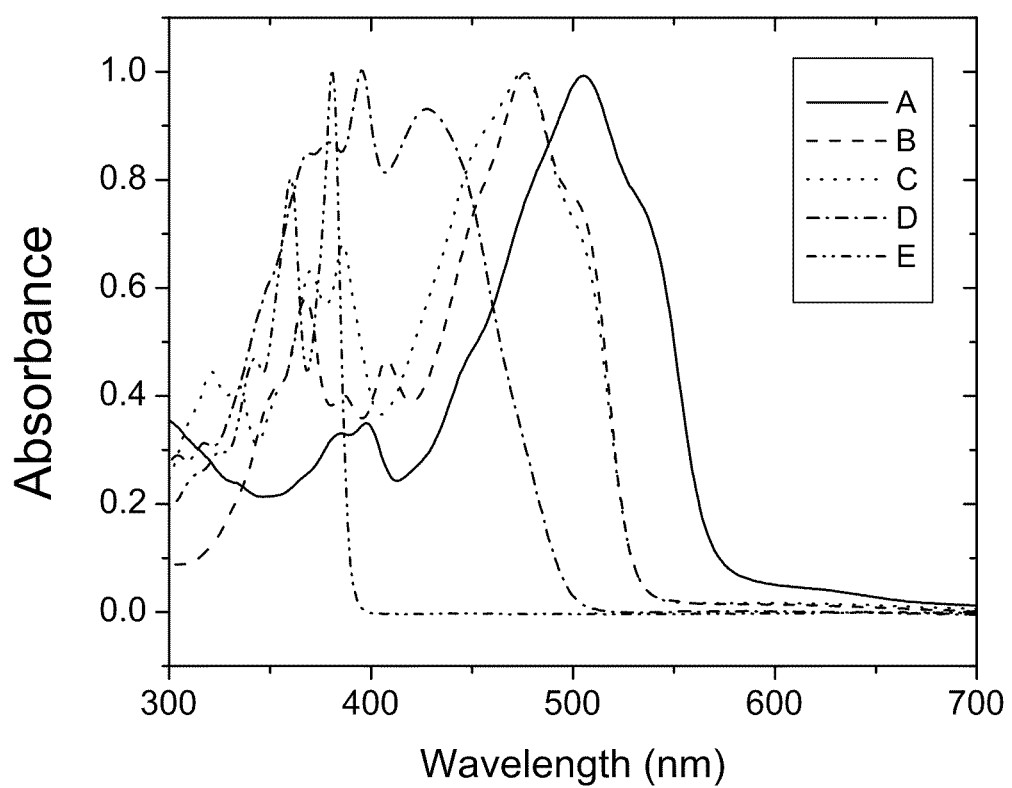
FIG. 9 shows the optical absorbance data of NDIS$_3$2EH (A), cis-NDIS$_2$2EH (B), trans-NDIS$_2$2EH (C), NDIS$_1$2EH (D), and NDI2EH (E) in chloroform solution.
Figure 10:
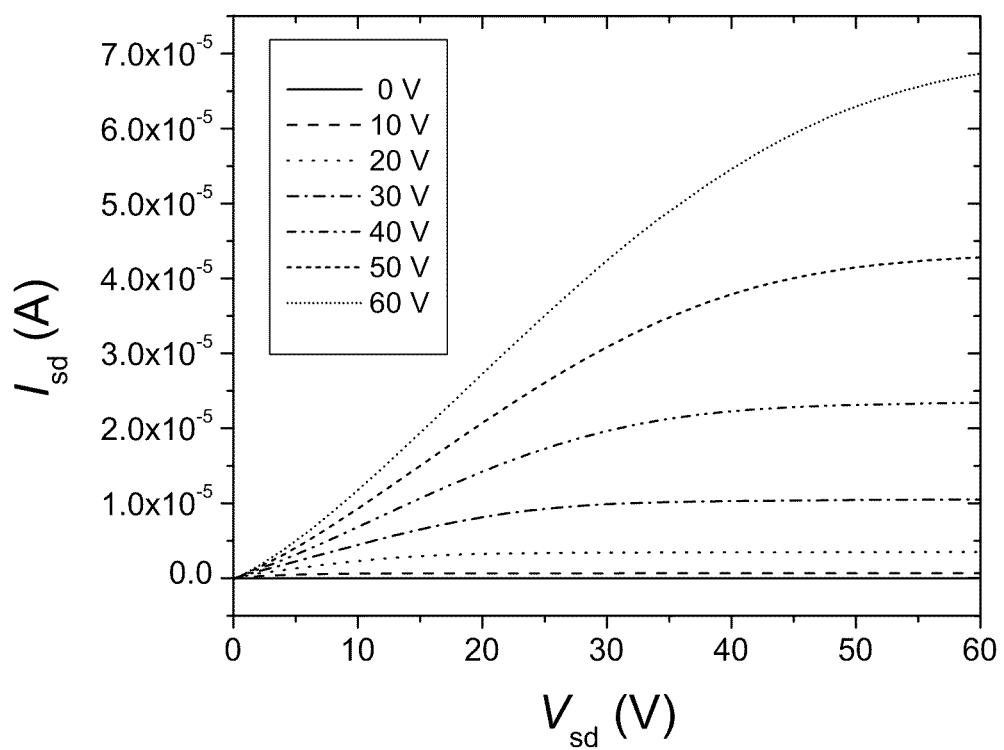
FIG. 10 shows typical output plots for (S,S)-trans-PDIS$_2$1MP at different gate voltages in bottom-gate bottom-contact configuration.
Figure 11:
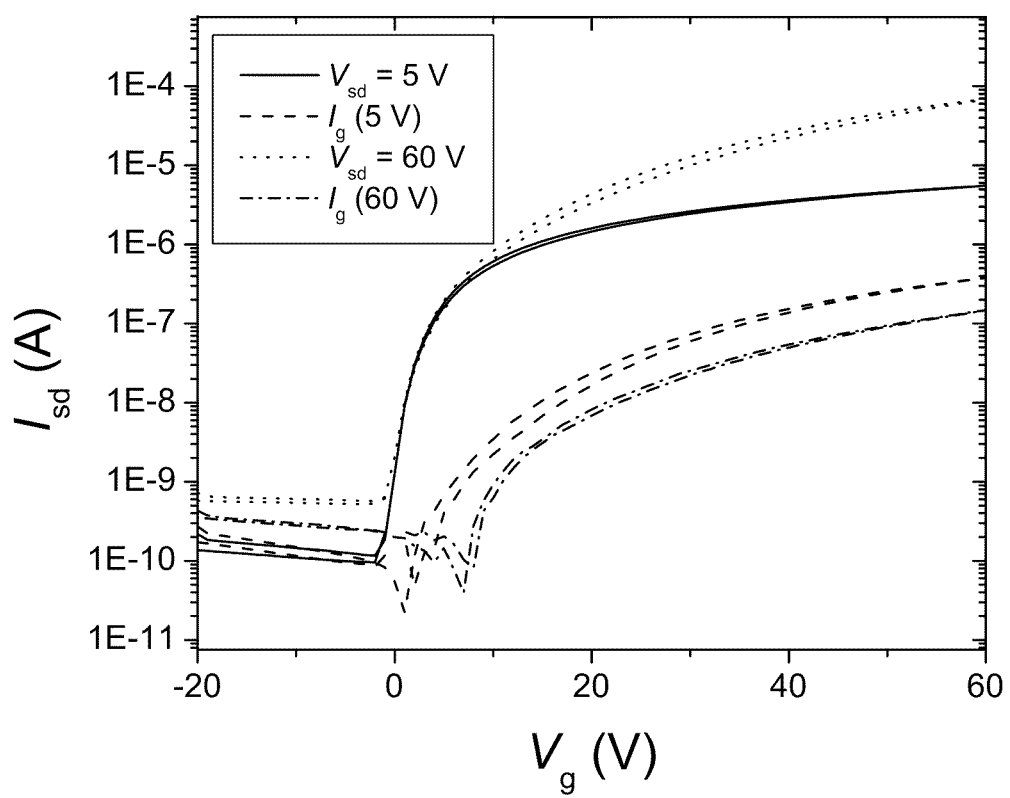
FIG. 11 shows typical transfer plots for (S,S)-trans-PDIS$_2$1MP in bottom-gate bottom-contact configuration.

Accordingly, another aspect of the present teachings relates to methods of fabricating an organic light-emitting transistor, an organic light-emitting diode (OLED), or an organic photovoltaic device that incorporates one or more semiconductor materials of the present teachings. FIG. 2 illustrates a representative structure of a bulk-heterojunction organic photovoltaic device (also known as solar cell) 20 which can incorporate one or more compounds of the present teachings as the donor and/or acceptor materials. As shown, a representative solar cell generally includes an anode 22 (e.g., ITO), a cathode 26 (e.g., aluminium or calcium), and an active layer 24 between the anode and the cathode which can incorporate one or more compounds of the present teachings as the electron donor (p-channel) and/or electron acceptor (n-channel) materials on a substrate 28 (e.g., glass). FIG. 3 illustrates a representative structure of an OLED 30 which can incorporate one or more compounds of the present teachings as electron-transporting and/or emissive and/or hole-transporting materials. As shown, an OLED generally includes a substrate (not shown), a transparent anode 32 (e.g., ITO), a cathode 40 (e.g., metal), and one or more organic layers which can incorporate one or more compounds of the present teachings as hole-transporting (n-channel) (layer 34 as shown) and/or emissive (layer 36 as shown) and/or electron-transporting (p-channel) materials (layer 38 as shown).

The following examples are provided to illustrate further and to facilitate the understanding of the present teachings and are not in any way intended to limit the invention.

Example 1

Synthesis

Example 1A

Preparation of (S,S)—PDI1MP, (S,S)—PDIS$_1$1MP, (S,S)-trans-PDIS$_2$1MP, (S,S)-cis-PDIS$_2$1MP (S,S)—PDIS$_3$1 MP and (S,S)—PDIS$_4$1MP

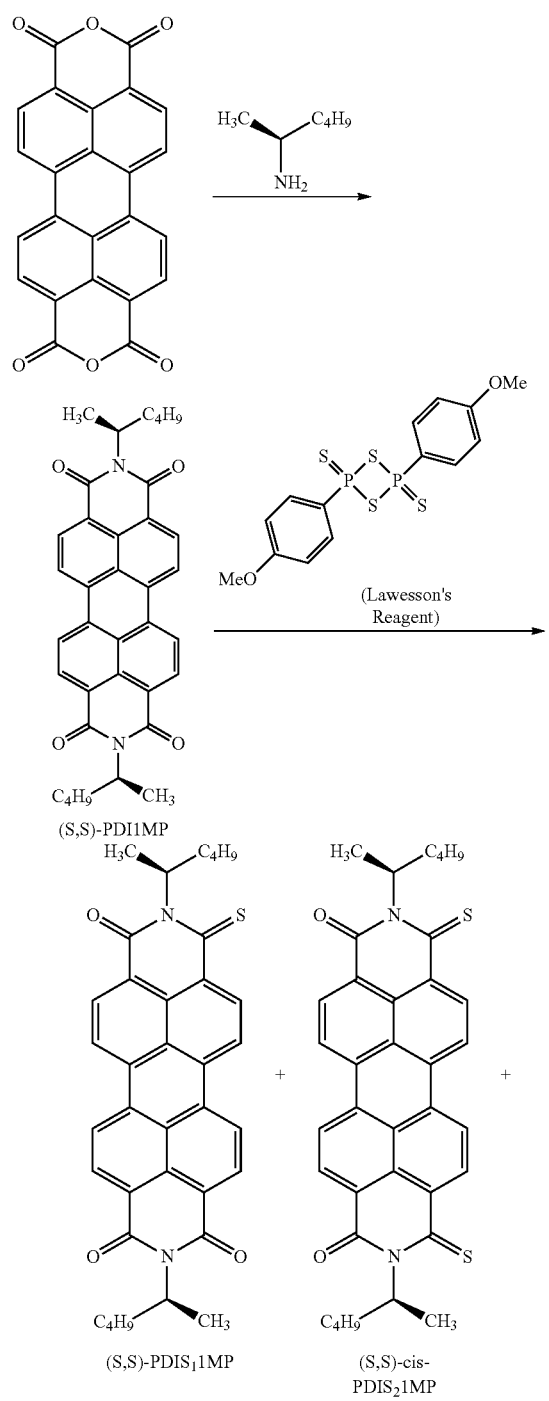
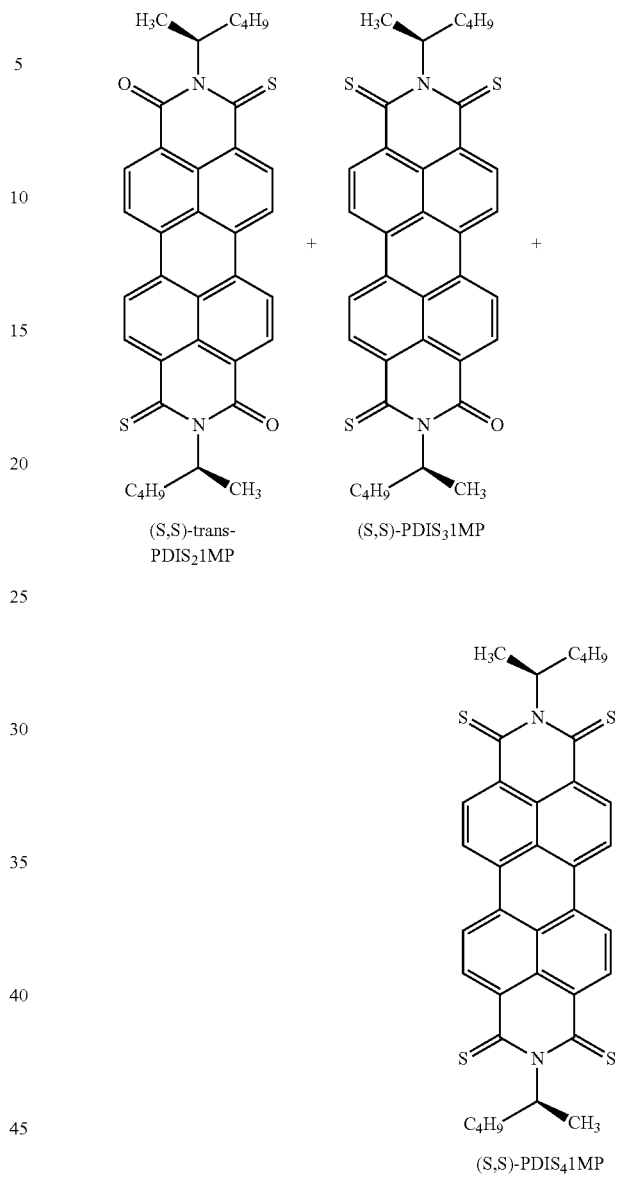

A mixture of 13.5 g (34.4 mmol) of perylene-3,4,9,10-tetracarboxylic dianhydride (Aldrich), 11.4 g (113 mmol) of (S)-(+)-2-aminohexane (Alfa Aesar, 99+% ee), and 130 g of imidazole was heated at 200° C. in a sealed vessel for 2 h. The mixture was cooled slightly and treated with 700 mL of 1,4-dioxane. The mixture was stirred at ambient temperature for 2 h then filtered. The filter cake was washed successively with methanol (100 mL) and diethyl ether (100 mL). The filter cake was dried to give 17.9 g (93% yield) of (S,S)—PDI1MP as a deep red powder.

$^1$H NMR (CDCl$_3$, 500 MHz): δ 8.62 (d, 4H, J=8.0), 8.51 (d, 4H, J=8.0), 5.32 (m, 2H), 2.25 (m, 2H), 1.98 (m, 2H), 1.67 (d, 6H, J=6.9), 1.44-1.24 (m, 8H), 0.90 (t, 6H, J=7.1). $^{13}$C NMR (CDCl$_3$, 125 MHz): δ 163.8, 134.3, 131.2, 129.3, 126.2, 122.6, 50.0, 33.3, 29.3, 22.6, 18.3, 14.0.

A mixture of 5.0 g (8.95 mmol) of (S,S)—PDI1MP, 10.0 g (24.7 mmol) of Lawesson's Reagent, and 100 mL of 1-methylnaphthalene was heated in an oil bath at 180° C. for 30 min. The mixture was cooled in a water bath and purified by flash chromatography (SiO$_2$, toluene, 7×40 cm). The concentrated product fractions were sonicated with acetone, filtered, and dried to give the thionated products.

(S,S)—PDIS$_4$1MP (trace) as a deep blue solid. R$_f$ 0.92 (TLC, toluene). $^1$H NMR (CDCl$_3$, 500 MHz): δ 8.96 (m, 4H), 8.47 (d, 4H, J=8.0), 6.74 (m, 2H), 2.52 (m, 2H), 2.22 (m, 2H), 1.85 (d, 6H, J=6.9), 1.38-1.26 (m, 8H), 0.88 (t, 6H, J=6.9).

(S,S)—PDIS$_3$1MP (~1% yield) as a deep blue solid. R$_f$ 0.83 (TLC, toluene). $^1$H NMR (CDCl$_3$, 500 MHz): δ 9.10-8.40 (m, 8H), 6.71 (m, 1H), 6.36 (m, 1H), 2.52 (m, 1H), 2.35-2.20 (m, 2H), 2.05 (m, 1H), 1.85 (d, 3H, J=6.9), 1.68 (d, 3H, J=6.7), 1.40-1.25 (m, 8H), 0.90 (t, 3H, J=7.1), 0.87 (t, 3H, J=7.1).

(S,S)-trans-PDIS$_2$1MP (1.52 g, 29% yield) as deep purple prisms. R$_f$ 0.67 (TLC, toluene). m.p. (DSC) 339° C. $^1$H NMR (CDCl$_3$, 500 MHz): δ 9.09 (d, 2H, J=8.4), 8.67 (d, 2H, J=8.0), 8.60 (d, 2H, J=8.2), 8.53 (d, 2H, J=8.5), 6.34 (m, 2H), 2.29 (m, 2H), 2.07 (m, 2H), 1.68 (d, 6H, J=6.8), 1.41-1.25 (m, 8H), 0.89 (t, 6H, J=7.0). Anal. Calcd for C$_{36}$H$_{34}$N$_2$O$_2$S$_2$: C, 73.19; H, 5.80; N, 4.74. Found: C, 72.94; H, 5.76; N, 4.74.

(S,S)-cis-PDIS$_2$1MP (20-30% typical yield) as a deep blue solid. R$_f$ 0.50 (TLC, toluene). $^1$H NMR (CDCl$_3$, 500 MHz): δ 9.13 (d, 2H, J=8.4), 8.71-8.65 (m, 4H), 8.56 (d, 2H, J=8.5), 6.34 (m, 2H), 2.30 (m, 2H), 2.07 (m, 2H), 1.67 (d, 6H, J=6.7), 1.40-1.25 (m, 8H), 0.89 (t, 6H, J=7.0). Anal. Calcd for C$_{36}$H$_{34}$N$_2$O$_2$S$_2$: C, 73.19; H, 5.80; N, 4.74. Found: C, 73.39; H, 5.99; N, 4.74.

(S,S)—PDIS$_1$1MP (<5% yield) as a deep purple solid. R$_f$ 0.23 (TLC, toluene). $^1$H NMR (CDCl$_3$, 500 MHz): δ 9.13 (d, 1H, J=8.4), 8.72-8.63 (m, 6H), 8.55 (d, 1H, J=8.5), 6.35 (m, 1H), 5.32 (m, 1H), 2.35-2.20 (m, 2H), 2.07 (m, 1H), 1.95 (m, 1H), 1.67 (d, 3H, J=6.7), 1.63 (d, 3H, J=6.9), 1.40-1.25 (m, 8H), 0.89 (t, 6H, J=7.1).

Optical absorbance data of (S,S)—PDI1MP, (S,S)—PDIS$_1$1MP, (S,S)-trans-PDIS$_2$1MP, (S,S)-cis-PDIS$_2$1MP, (S,S)—PDIS$_3$1MP, and (S,S)—PDIS$_4$1MP are summarized in Table 1.

TABLE 1

Summary of optical absorbance data (chloroform solution).

| | λ$_{onset}$ (nm) | E$_g$ (eV) |
|---|---|---|
| (S,S)-PDI1MP | 540 | 2.30 |
| (S,S)-PDIS$_1$1MP | 605 | 2.05 |
| (S,S)-trans-PDIS$_2$1MP | 645 | 1.92 |
| (S,S)-cis-PDIS$_2$1MP | 645 | 1.92 |
| (S,S)-PDIS$_3$1MP | 710 | 1.75 |
| (S,S)-PDIS$_4$1MP | 765 | 1.62 |

Example 1B

Preparation of trans-PDIS$_2$1 MHex and cis-PDIS$_2$1 MHex (Mixture of Racemic And Meso Forms)

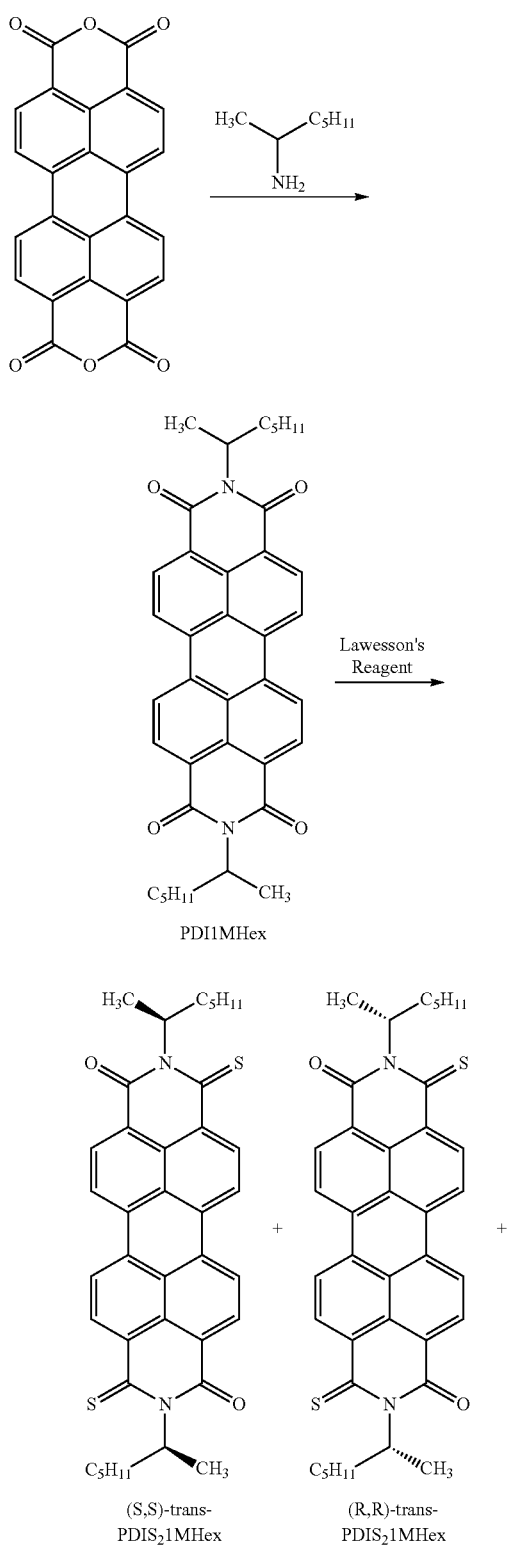

(S,S)-trans-PDIS$_2$MHex (R,R)-trans-PDIS$_2$MHex

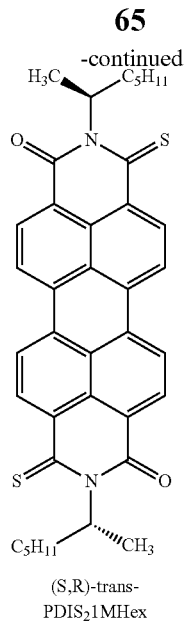
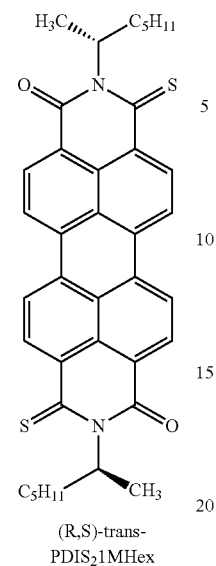

(S,R)-trans-PDIS₂1MHex  +  (R,S)-trans-PDIS₂1MHex

A mixture of 4.2 g (10.7 mmol) of perylene-3,4,9,10-tetracarboxylic dianhydride (Aldrich), 4.1 g (35.6 mmol) of (+/−)-2-aminoheptane (Aldrich), and 40 g of imidazole was heated in a sealed vessel at 200° C. for 2 h. The mixture was cooled slightly and triturated with 70 mL of 1,4-dioxane. The mixture was cooled to room temperature and filtered. The filter cake was refluxed with 180 mL of 1,4-dioxane for 10 min., cooled to room temperature, filtered, and washed successively with 100 mL of methanol and twice with 80 mL of diethyl ether. The filter cake was dried to give 4.8 g (76% yield) of PDI1MHex as a bright red powder.

$^1$H NMR (CDCl$_3$, 500 MHz): δ 8.68 (d, 4H, J=8.0), 8.63 (d, 4H, J=8.0), 5.30 (m, 2H), 2.23 (m, 2H), 1.94 (m, 2H), 1.61 (d, 6H, J=7.5), 1.42-1.20 (m, 12H), 0.85 (t, 6H, J=8.0). Anal. Calcd for C$_{38}$H$_{38}$N$_2$O$_4$: C, 77.79; H, 6.53; N, 4.77. Found: C, 77.69; H, 6.46; N, 4.85.

A mixture of 1.24 g (2.1 mmol) of PDI1MHex, 2.3 g (5.7 mmol) of Lawesson's Reagent, and 25 mL of 1-methylnaphthalene was heated in an oil bath at 180° C. for 8 min. The mixture was cooled immediately in a water bath and purified by flash chromatography (SiO$_2$, toluene, 5.5×40 cm). The concentrated product fraction was sonicated with 20 mL of acetone, filtered, and dried to give 180 mg (14% yield) of trans-PDIS$_2$1MHex (mixture of racemic and meso forms) as a deep purple solid.

$^1$H NMR (CDCl$_3$, 500 MHz): δ 8.97 (m, 2H), 8.59 (m, 2H), 8.45 (m, 2H), 8.36 (m, 2H), 6.30 (m, 2H), 2.27 (m, 2H), 2.07 (m, 2H), 1.68 (m, 6H), 1.47-1.23 (m, 12H), 0.86 (m, 6H). Anal. Calcd for C$_{38}$H$_{38}$N$_2$O$_2$S$_2$: C, 73.75; H, 6.19; N, 4.53. Found: C, 74.05; H, 6.16; N, 4.60.

cis-PDIS$_2$1MHex (mixture of racemic and meso forms) (180 mg, 14% yield) was isolated as a deep purple solid. $^1$H NMR (CDCl$_3$, 500 MHz): δ 8.89 (m, 2H), 8.50 (m, 2H), 8.33 (m, 2H), 8.19 (m, 2H), 6.29 (m, 2H), 2.26 (m, 2H), 2.08 (m, 2H), 1.69 (m, 6H), 1.46-1.24 (m, 12H), 0.87 (m, 6H). Anal. Calcd for C$_{38}$H$_{38}$N$_2$O$_2$S$_2$: C, 73.75; H, 6.19; N, 4.53. Found: C, 74.01; H, 6.00; N, 4.62.

Example 1C

Preparation of (S,S)-trans-PDIS$_2$1MHex

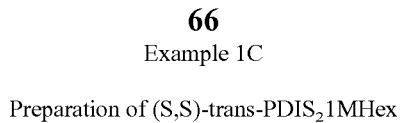

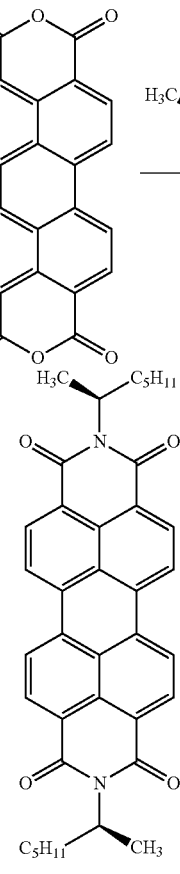

(S,S)-PDI1MHex

→ Lawesson's Reagent →

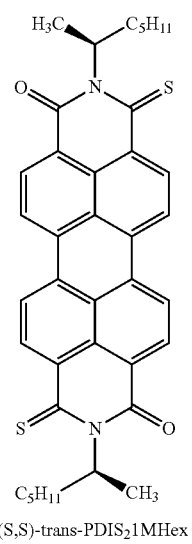

(S,S)-trans-PDIS$_2$1MHex

A mixture of 4.5 g (11.5 mmol) of perylene-3,4,9,10-tetracarboxylic dianhydride (Aldrich), 4.3 g (37.3 mmol) of (S)-(+)-2-aminoheptane (Alfa Aesar, 99+% ee), and 40 g of imidazole was heated at 200° C. in a sealed vessel for 2 h. The mixture was cooled slightly and triturated with 100 mL of 1,4-dioxane. The mixture was cooled to room temperature and filtered. The filter cake was refluxed with 180 mL of 1,4-dioxane for 10 min., cooled to room temperature, filtered, and washed successively with 100 mL of methanol and twice with 80 mL of diethyl ether. The filter cake was dried to give 5.9 g (88% yield) of (S,S)—PDI1MHex as a bright red powder.

$^1$H NMR (CDCl$_3$, 500 MHz): δ 8.68 (d, 4H, J=7.5), 8.63 (d, 4H, J=8.5), 5.30 (m, 2H), 2.22 (m, 2H), 1.94 (m, 2H), 1.61 (d, 6H, J=7.0), 1.42-1.21 (m, 12H), 0.85 (t, 6H, J=7.0). Anal. Calcd. for C$_{38}$H$_{38}$N$_2$O$_4$: C, 77.79; H, 6.53; N, 4.77. Found: C, 78.10; H, 6.55; N, 4.91.

A mixture of 1.61 g (2.7 mmol) of (S,S)—PDI1MHex, 3.0 g (7.4 mmol) of Lawesson's Reagent, and 30 mL of 1-methylnaphthalene was heated in an oil bath at 180° C. for 8 min. The mixture was cooled immediately in a water bath and purified by flash chromatography (SiO$_2$, toluene, 5.5×40 cm). The concentrated product fraction was sonicated with 20 mL of acetone, filtered, and dried to give 140 mg (8% yield) of (S,S)-trans-PDIS$_2$1MHex as a deep purple solid.

$^1$H NMR (CDCl$_3$, 500 MHz): δ 9.04 (d, 2H, J=8.5), 8.64 (d, 2H, J=8.0), 8.55 (d, 2H, J=8.0), 8.47 (d, 2H, J=8.5), 6.32 (m, 2H), 2.27 (m, 2H), 2.07 (m, 2H), 1.67 (d, J=7.0, 6H), 1.45-1.24 (m, 12H), 0.85 (t, 6H, J=7.5). Anal. Calcd. for C$_{38}$H$_{38}$N$_2$O$_2$S$_2$: C, 73.75; H, 6.19; N, 4.53. Found: C, 73.98; H, 5.97; N, 4.63.

Example 1D

Preparation of (R,R)-trans-PDIS$_2$1MHept

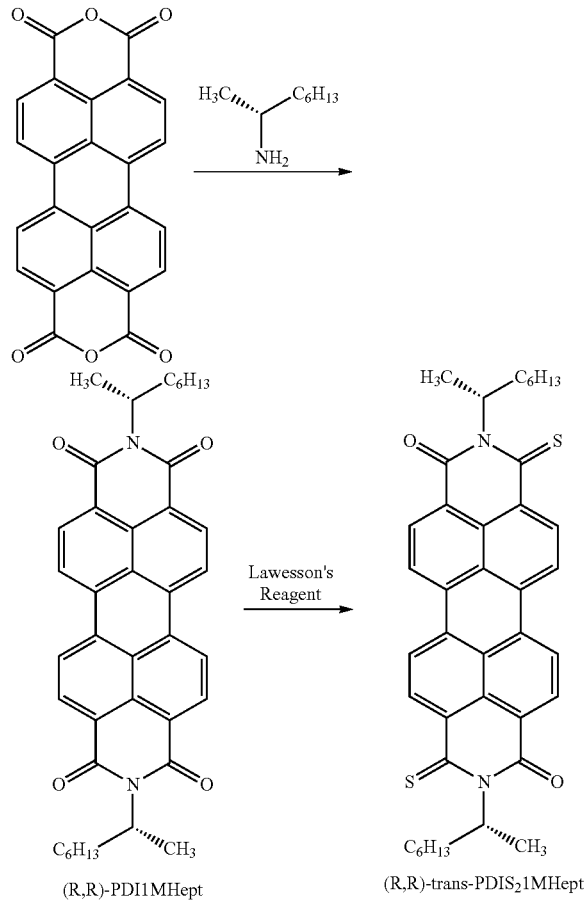

A mixture of 2.0 g (5.10 mmol) of perylene-3,4,9,10-tetracarboxylic dianhydride (Aldrich), 2.1 g (14.4 mmol) of (R)-(−)-2-aminooctane (Alfa Aesar, 99+% ee), and 30 g of imidazole was heated at 200° C. in a sealed vessel for 2 h. The mixture was cooled slightly and treated with 100 mL of dioxane. The mixture was stirred at ambient temperature then filtered. The filter cake was washed successively with dioxane (3×20 mL), and diethyl ether (3×20 mL). The filter cake was dried to give 2.71 g (87% yield) of (R,R)—PDI1MHept as a deep red powder.

$^1$H NMR (CDCl$_3$, 500 MHz): δ 8.68 (d, 4H, J=7.9), 8.62 (d, 4H, J=8.1), 5.31 (m, 2H), 2.23 (m, 2H), 1.95 (m, 2H), 1.63 (d, 6H, J=6.9), 1.40-1.25 (m, 16H), 0.86 (t, 6H, J=7.0).

A mixture of 2.08 g (3.38 mmol) of (R,R)—PDI1MHept, 3.7 g (9.15 mmol) of Lawesson's Reagent, and 30 mL of 1-methylnaphthalene was heated in an oil bath at 180° C. for 30 min. The mixture was cooled in a water bath and purified by flash chromatography (SiO$_2$, toluene, 7×40 cm). The concentrated product fraction was sonicated with 30 mL of acetone, filtered, and dried to give 545 mg (25% yield) of (R,R)-trans-PDIS$_2$1MHept as a deep purple solid.

$^1$H NMR (CDCl$_3$, 500 MHz): δ 9.03 (d, 2H, J=8.4), 8.63 (d, 2H, J=8.0), 8.52 (d, 2H, J=8.1), 8.44 (d, 2H, J=8.5), 6.33 (m, 2H), 2.27 (m, 2H), 2.07 (m, 2H), 1.70 (d, 6H, J=6.7), 1.44-1.25 (m, 16H), 0.86 (t, 6H, J=6.9). Anal. Calcd for C$_{40}$H$_{42}$N$_2$O$_2$S$_2$: C, 74.27; H, 6.54; N, 4.33. Found: C, 74.52; H, 6.38; N, 4.46.

Example 1E

Preparation of trans-PDIS$_2$1MHept

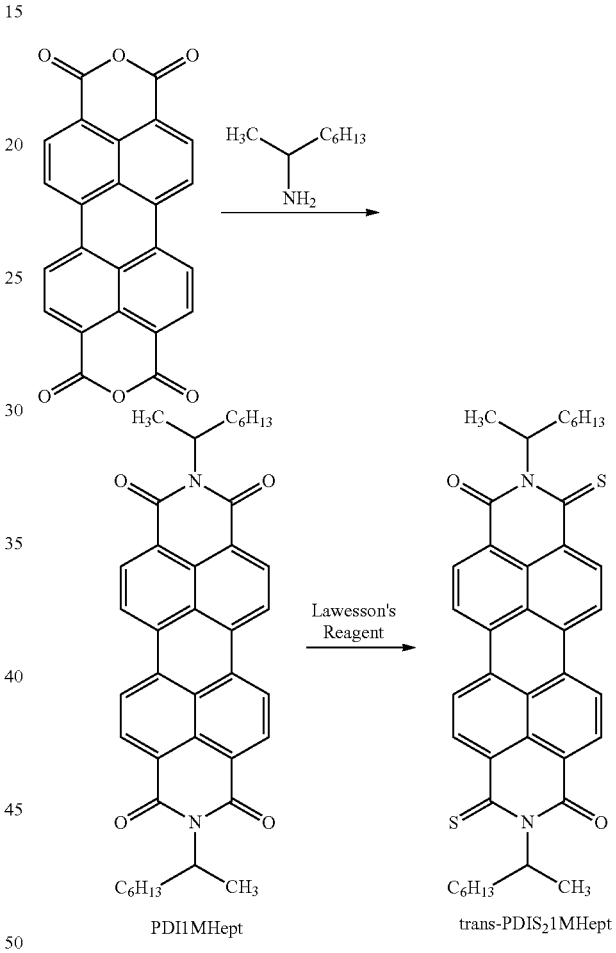

A mixture of 2.0 g (5.10 mmol) of perylene-3,4,9,10-tetracarboxylic dianhydride (Aldrich), 2.0 g (15.4 mmol) of (+/−)-2-aminooctane (Alfa Aesar), and 30 g of imidazole was heated in a sealed vessel at 200° C. for 2 h. The mixture was cooled slightly and treated with 200 ml of dioxane. The mixture was stirred at ambient temperature overnight then filtered. The filter cake was washed successively with 100 mL each of dioxane, methanol, acetone, and diethyl ether. The filter cake was dried to give 2.84 g (91% yield) of PDI1MHept as a bright red powder.

$^1$H NMR (CDCl$_3$, 500 MHz): δ 8.65 (d, 4H, J=7.9), 8.57 (d, 4H, J=8.1), 5.31 (m, 2H), 2.23 (m, 2H), 1.95 (m, 2H), 1.63 (d, 6H, J=6.9), 1.40-1.25 (m, 16H), 0.86 (t, 6H, J=7.0).

A mixture of 1.0 g (1.63 mmol) of PDI1MHept, 1.85 g (4.6 mmol) of Lawesson's Reagent, and 15 mL of 1-methylnaphthalene was heated in an oil bath at 180° C. for 30 min. The mixture was cooled immediately in a water bath and purified by flash chromatography (SiO₂, toluene, 5.5×40 cm). The concentrated product fraction was sonicated with 20 mL of acetone, filtered, and dried to give 230 mg (22% yield) of trans-PDIS₂1MHept as a deep purple solid.

¹H NMR (CDCl₃, 500 MHz): δ 8.95 (m, 2H), 8.59 (m, 2H), 8.43 (m, 2H), 8.34 (m, 2H), 6.31 (m, 2H), 2.29 (m, 2H), 2.10 (m, 2H), 1.70 (m, 6H), 1.44-1.25 (m, 16H), 0.87 (m, 6H). Anal. Calcd for C₄₀H₄₂N₂O₂S₂: C, 74.27; H, 6.54; N, 4.33. Found: C, 74.52; H, 6.29; N, 4.61.

Example 1F

Preparation of (S,S)-trans-PDIS₂1MO

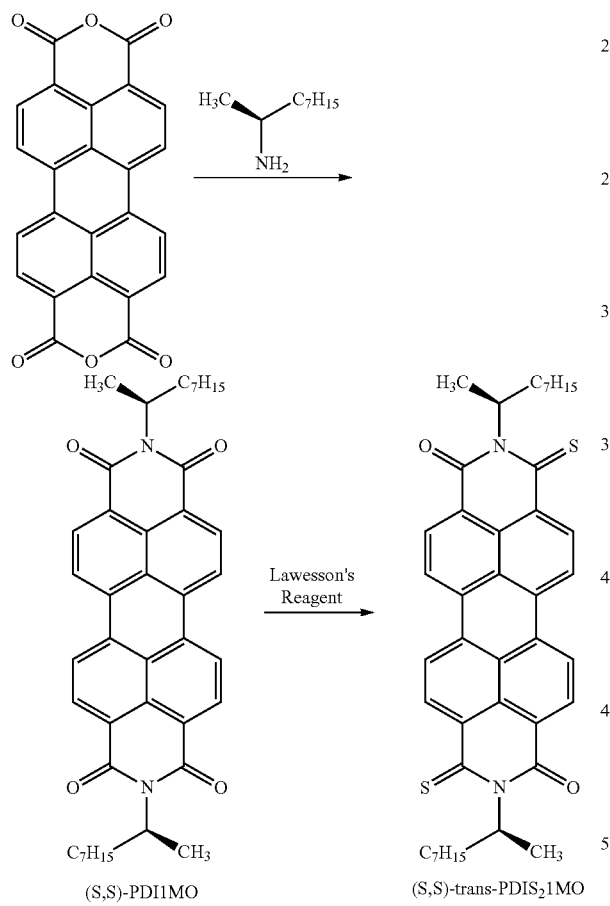

A mixture of 2.0 g (5.10 mmol) of perylene-3,4,9,10-tetracarboxylic dianhydride (Aldrich), 2.2 g (15.4 mmol) of (S)-(+)-2-aminononane (Alfa Aesar, 99+% ee), and 30 g of imidazole was heated at 200° C. in a sealed vessel for 2 h. The mixture was cooled slightly and treated with 150 mL of dioxane. The mixture was stirred at ambient temperature for 2 h then filtered. The filter cake was washed successively with methanol (2×100 mL), acetone (2×100 mL), and diethyl ether (2×100 mL). The filter cake was dried to give 3.05 g (93% yield) of (S,S)—PDI1MO as a deep red powder.

¹H NMR (CDCl₃, 500 MHz): δ 8.64 (d, 4H, J=7.9), 8.55 (d, 4H, J=8.1), 5.31 (m, 2H), 2.23 (m, 2H), 1.95 (m, 2H), 1.64 (d, 6H, J=6.9), 1.42-1.20 (m, 20H), 0.85 (t, 6H, J=7.0).

A mixture of 1.0 g (1.56 mmol) of (S,S)—PDI1MO, 1.75 g (4.33 mmol) of Lawesson's Reagent, and 7 mL of 1-methylnaphthalene was heated in an oil bath at 180° C. for 15 min. The mixture was cooled immediately in a water bath and purified by flash chromatography (SiO₂, toluene, 5.5×40 cm). The concentrated product fraction was sonicated with 25 mL of acetone, filtered, and dried to give 240 mg (23% yield) of (S,S)-trans-PDIS₂1MO as a deep purple solid.

¹H NMR (CDCl₃, 500 MHz): δ 9.07 (d, 2H, J=8.4), 8.67 (d, 2H, J=8.0), 8.58 (d, 2H, J=8.1), 8.52 (d, 2H, J=8.5), 6.33 (m, 2H), 2.29 (m, 2H), 2.06 (m, 2H), 1.68 (d, 6H, J=6.5), 1.44-1.20 (m, 20H), 0.85 (t, 6H, J=7.0). Anal. Calcd for C₄₂H₄₆N₂O₂S₂: C, 74.74; H, 6.87; N, 4.15. Found: C, 74.98; H, 6.62; N, 4.23.

Example 1G

Preparation of trans-PDIS₂1EPr and cis-PDIS₂1EPr

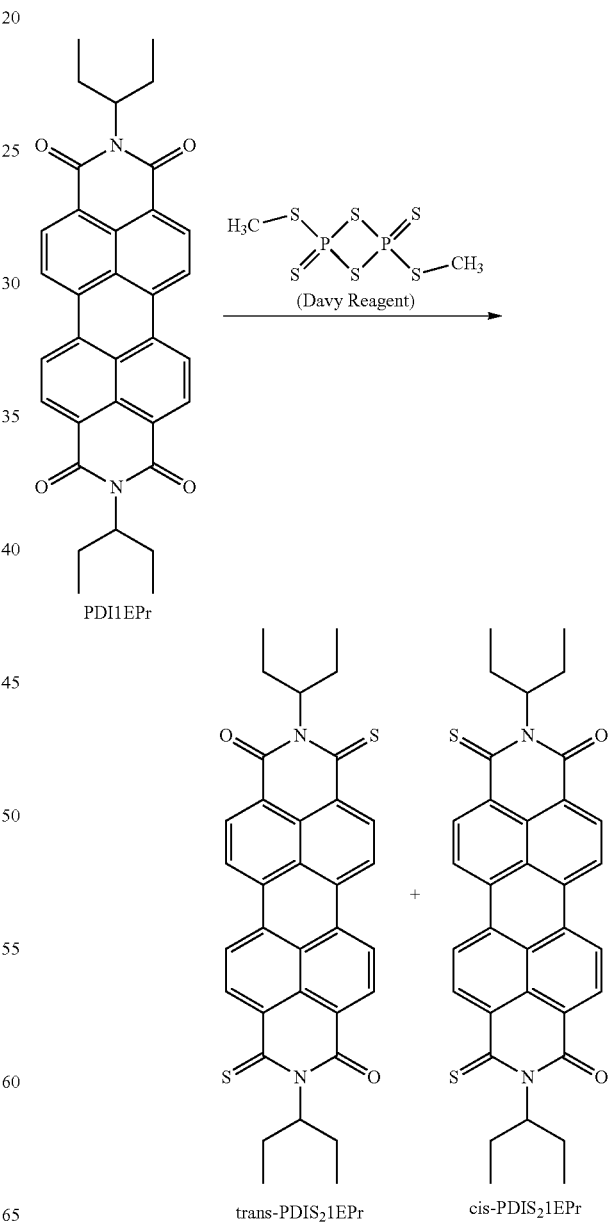

A mixture of 1.5 g (3.8 mmol) of perylene-3,4,9,10-tetra-carboxylic dianhydride (Aldrich), 1.0 g (11.4 mmol) of 3-aminopentane (Aldrich), and 20 g of imidazole was heated at 200° C. in a sealed vessel for 2 h. The mixture was cooled slightly and treated with 100 mL of dioxane. The mixture was stirred at ambient temperature for 2 h then filtered. The filter cake was washed successively with methanol (100 mL), and diethyl ether (100 mL). The filter cake was dried to give 1.86 g (92% yield) of PDI1EPr as deep red needles.

$^1$H NMR (CDCl$_3$, 500 MHz): δ 8.69 (d, 4H, J=7.8), 8.64 (d, 4H, J=8.1), 5.09 (m, 2H), 2.29 (m, 4H), 1.97 (m, 4H), 0.95 (t, 12H, J=7.5).

A mixture of 0.374 g (0.705 mmol) of PDI1EPr, 0.40 g (1.41 mmol) of Davy Reagent, and 15 mL of o-dichlorobenzene was heated in an oil bath at 180° C. for 7 min. The mixture was cooled immediately in a water bath and purified by flash chromatography (SiO$_2$, toluene→methylene chloride, 5.5×40 cm). The concentrated product fraction was sonicated with 25 mL of acetone, filtered, and dried to give 107 mg (27% yield) of trans-PDIS$_2$1EPr as a deep purple solid.

$^1$H NMR (CDCl$_3$, 500 MHz): δ 9.08 (d, 2H, J=8.4), 8.67 (d, 2H, J=8.1), 8.59 (d, 2H, J=8.1), 8.52 (d, 2H, J=8.5), 6.32 (m, 2H), 2.35 (m, 4H), 2.08 (m, 4H), 0.98 (t, 12H, J=7.5). Anal. Calcd for C$_{34}$H$_{30}$N$_2$O$_2$S$_2$: C, 72.57; H, 5.37; N, 4.98. Found: C, 72.65; H, 5.33; N, 5.06.

cis-PDIS$_2$1EPr (104 mg, 26% yield) was isolated as a deep purple solid.

$^1$H NMR (CDCl$_3$, 500 MHz): δ 9.09 (d, 2H, J=8.3), 8.66 (d, 2H, J=8.0), 8.62 (d, 2H, J=8.1), 8.49 (d, 2H, J=8.5), 6.32 (m, 2H), 2.35 (m, 4H), 2.08 (m, 4H), 0.98 (t, 12H, J=7.5). Anal. Calcd for C$_{34}$H$_{30}$N$_2$O$_2$S$_2$: C, 72.57; H, 5.37; N, 4.98. Found: C, 72.82; H, 5.42; N, 5.20.

Example 1H

Preparation of trans-PDIS$_2$1M3MB

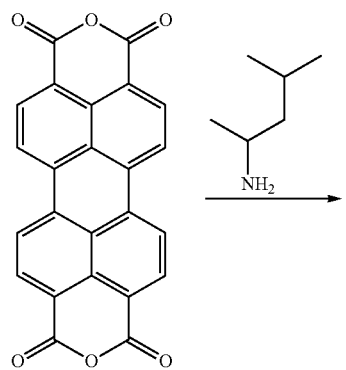

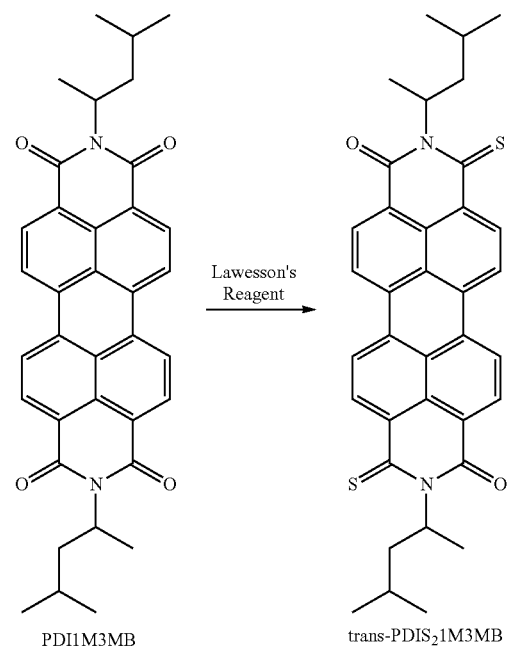

A mixture of 1.3 g (3.3 mmol) of perylene-3,4,9,10-tetra-carboxylic dianhydride (Aldrich), 1.0 g (9.8 mmol) of 1,3-dimethylbutylamine (Aldrich), and 25 g of imidazole was heated at 200° C. in a sealed vessel for 2 h. The mixture was cooled slightly and treated with 100 mL of 1,4-dioxane. The mixture was stirred at ambient temperature for 2 h then filtered. The filter cake was washed successively with methanol (100 mL), and diethyl ether (100 mL). The filter cake was dried to give 1.71 g (93% yield) of PDIS1M3 MB as a bright red powder.

$^1$H NMR (CDCl$_3$, 500 MHz): δ 0.88 (dd, 12H), 1.45-1.55 (m, 8H), 1.67 (m, 2H), 2.14 (m, 2H), 5.33 (m, 2H), 8.49 (d, 4H, J=8.0 Hz), 8.56 (d, 4H, J=8.0 Hz).

A mixture of 0.40 g (0.72 mmol) of PDIS1M3 MB, 0.81 g (2.00 mmol) of Lawesson's reagent, and 6 mL of 1-methylnaphthalene was heated in an oil bath at 180° C. for 30 min. The reaction mixture was cooled down to room temperature in a water bath and directly purified by flash column chromatography (SiO$_2$, toluene). The concentrated product fractions were sonicated with acetone, filtered, and dried to give trans-PDIS$_2$1M3 MB (72 mg, 17% yield) as a deep purple solid.

$^1$H NMR (CDCl$_3$, 500 MHz): δ 0.87 (d, 12H, J=6.5 Hz), 1.48-1.60 (m, 8H), 1.86 (m, 2H), 2.13 (m, 2H), 6.30 (m, 2H), 8.43 (d, 2H, J=8.5 Hz), 8.49 (d, 2H, J=8.5 Hz), 8.56 (d, 2H, J=8.5 Hz), 8.99 (d, 2H, J=8.5 Hz). Anal. Calcd for C$_{36}$H$_{34}$N$_2$O$_2$S$_2$: C, 73.19; H, 5.80; N, 4.74. Found: C, 73.21; H, 5.69; N, 4.69.

Example 1I

Preparation of trans-PDIS₂2OD

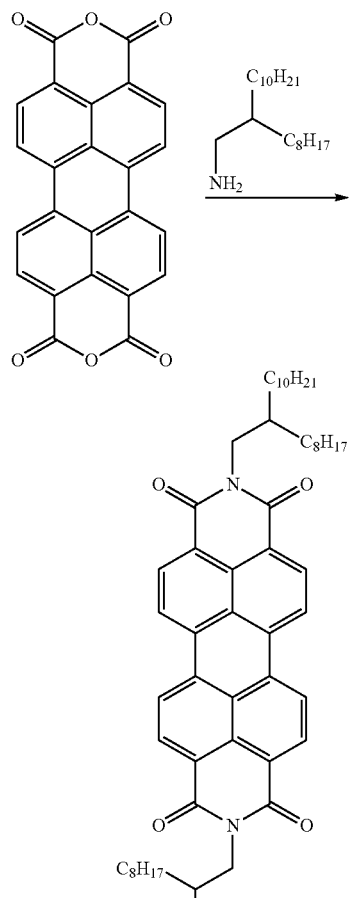

A mixture of 0.67 g (1.71 mmol) of perylene-3,4,9,10-tetracarboxylic dianhydride (Aldrich), 1.52 g (5.11 mmol) of 2-octyldodecylamine, 3 mL of o-xylene, and 0.92 g (13.5 mmol) of imidazole was stirred under nitrogen atmosphere at 180° C. for 4 h. The reaction mixture was cooled to room temperature, treated with methanol (20 mL), and the resulting mixture was sonicated for 10 min. The solid product was collected by filtration and then purified by column chromatography on silica gel with chloroform as eluent, affording 1.51 g (93% yield) of PDI2OD as a red solid.

$^1$H NMR (CDCl$_3$, 500 MHz): δ 8.56 (d, 4H, J=8.0), 8.44 (d, 4H, J=8.0), 4.13 (d, 4H, J=7.0), 2.00 (m, 2H), 1.49-1.18 (m, 64H), 0.88-0.82 (t, 12H, J=6.5). Anal. Calcd for C$_{64}$H$_{90}$N$_2$O$_4$: C, 80.79; H, 9.53; N, 2.94. Found: C, 80.76; H, 9.34; N, 3.08.

A mixture of 0.17 g (0.19 mmol) of PDI2OD, 0.15 g (0.37 mmol) of Lawesson's Reagent, and 20 mL of toluene was refluxed for 18 h. The mixture was concentrated in vacuo and purified by flash chromatography (SiO$_2$, chloroform, 3.5×40 cm) to give 45 mg (25% yield) of trans-PDIS$_2$2OD as a deep purple solid.

$^1$H NMR (CDCl$_3$, 500 MHz): δ 8.60 (d, 2H, J=8.2), 8.38 (d, 2H, J=7.9), 8.08 (d, 2H, J=8.1), 7.98 (d, 2H, J=8.4), 4.60 (d, 4H, J=6.6), 2.25 (m, 2H), 1.60-1.10 (m, 64H), 0.87 (m, 12H). Anal. Calcd for C$_{64}$H$_{90}$N$_2$O$_2$S$_2$: C, 78.15; H, 9.22; N, 2.85. Found: C, 77.98; H, 8.97; N, 3.01.

TABLE 2

| First reduction potentials and corresponding LUMO energies for PDI2OD and trans-PDIS₂2OD. | | |
|---|---|---|
|  | $E_{1/2}$ (V) | $E_{LUMO}$ (eV) |
| PDI2OD | -0.52 | -3.90 |
| trans-PDIS₂2OD | -0.28 | -4.16 |

Example 1J

Preparation of trans-PDIS₂1MP-CN₂

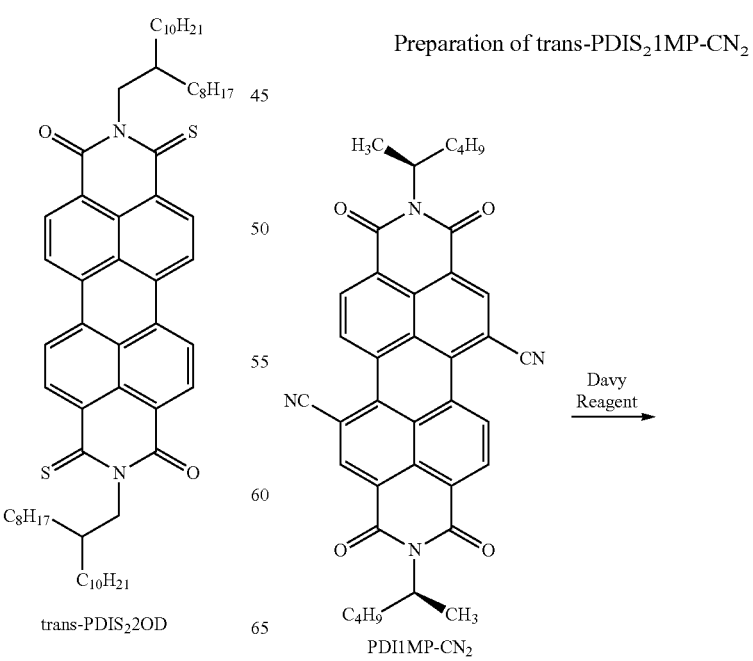

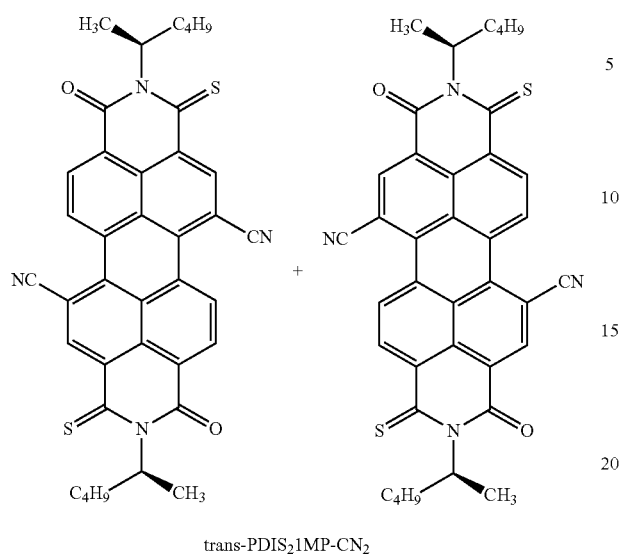

trans-PDIS₂1MP-CN₂

A mixture of 0.175 g (0.288 mmol) of PDI1MP-CN₂ (as a mixture of 1,6- and 1,7-cyanated isomers), 0.18 g (0.63 mmol) of Davy Reagent, and 4 mL of o-dichlorobenzene was heated in an oil bath at 180° C. for 15 min. The mixture was cooled in a water bath and purified by flash chromatography (SiO₂, chloroform, 3×20 cm). The concentrated product fractions were sonicated with 20 mL of methanol, filtered, and dried to give 40 mg (22% yield) of trans-PDIS₂1MP-CN₂ as a black solid.

¹H NMR (CDCl₃, 500 MHz): δ 9.70-8.80 (m, 6H), 6.21 (m, 2H), 2.27 (m, 2H), 2.04 (m, 2H), 1.65 (m, 6H), 1.40-1.19 (m, 8H), 0.87 (t, 6H, J=7.0). Anal. Calcd for $C_{38}H_{32}N_2O_2S_2$: C, 71.22; H, 5.03; N, 8.74. Found: C, 70.81; H, 5.22; N, 8.53.

Example 1K

Preparation of trans-NDIS₂Cy and cis-NDIS₂Cy

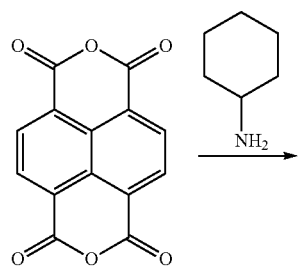

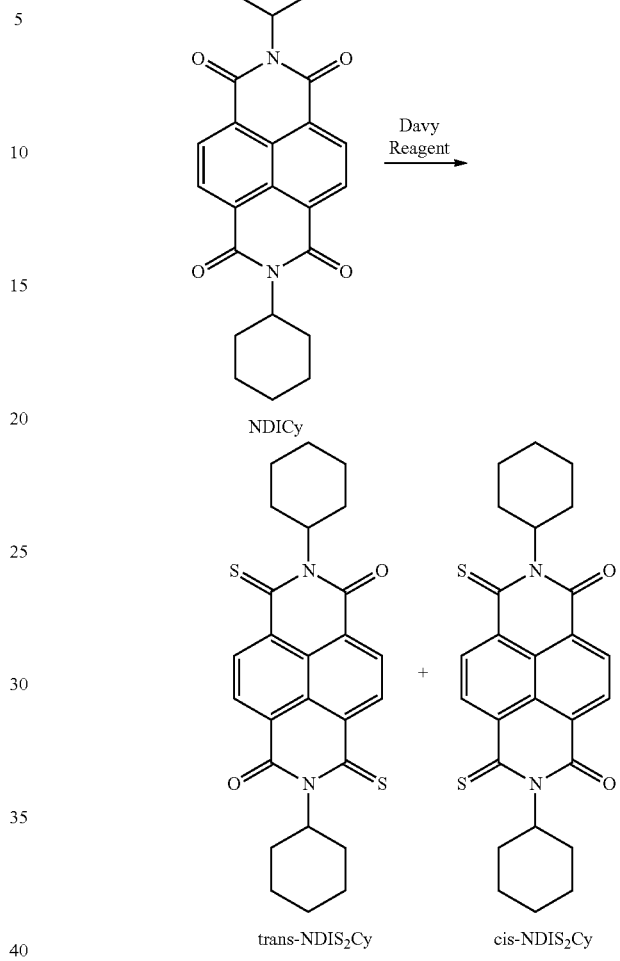

trans-NDIS₂Cy    cis-NDIS₂Cy

A mixture of 3.1 g (11.6 mmol) of naphthalene-3,4,9,10-tetracarboxylic dianhydride (Aldrich), 10 mL (87 mmol) of cyclohexylamine (Aldrich), and 40 g of imidazole was heated at 185° C. in a sealed vessel for 30 min. The mixture was cooled slightly and treated with 200 mL of acetone. The mixture was filtered and filter cake was washed three times with 50 mL each of acetone and dried to give 4.62 g (93% yield) of NDICy as a tan powder. The crude material was of sufficient purity to carry forward without further purification.

A mixture of 0.62 g (1.44 mmol) of NDICy, 0.85 g (3.0 mmol) of Davy Reagent, and 10 mL of 1-methylnaphthalene was heated in an oil bath at 180° C. for 10 min. The mixture was cooled immediately in a water bath and purified by flash chromatography (SiO₂, 0.1% pyridine in toluene, 5.5×40 cm). The product crystallized from the target fractions and was filtered off to give 81 mg (12% yield) of trans-NDIS₂Cy as bronze-colored prisms.

Anal. Calcd for $C_{26}H_{26}N_2O_2S_2$: C, 67.50; H, 5.66; N, 6.06. Found: C, 67.85; H, 5.71; N, 6.04.

The fractions containing the cis isomer were concentrated to dryness, sonicated with 20 mL of acetone, filtered and dried to give 236 mg (35% yield) of cis-NDIS₂Cy as a brown powder.

Anal. Calcd for $C_{26}H_{26}N_2O_2S_2$: C, 67.50; H, 5.66; N, 6.06. Found: C, 67.61; H, 5.66; N, 6.09.

Example 1L

Preparation of NDIS$_1$2EH, trans-NDIS$_2$2EH, cis-NDIS$_2$2EH, NDIS$_3$2EH

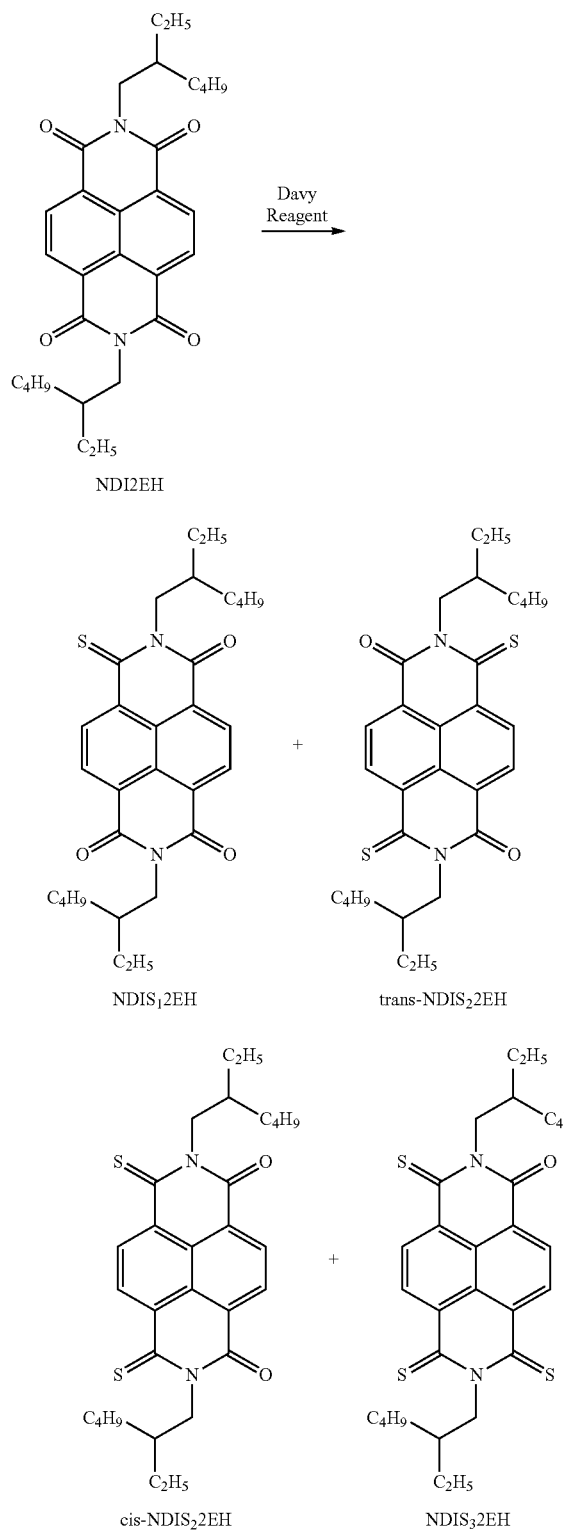

A mixture of 2.00 g (4.08 mmol) of NDI2EH, 2.70 g (9.49 mmol) of Davy reagent, and 100 mL of 1,2-dichlorobenzene was heated in an oil bath at 170° C. for 10 min. The reaction mixture was cooled down to room temperature in a water bath and directly purified by flash column chromatography (Silica gel, Chloroform:Hexanes (5:1, v/v)) affording pure fractions of thionated products.

NDIS$_1$2EH, 600 mg, 29% yield, yellow solid. $^1$H NMR (CDCl$_3$, 500 MHz): δ 0.86-0.95 (m, 10H), 1.28-1.43 (m, 18H), 1.94 (m, 1H), 2.17 (m, 1H), 4.14 (m, 2H), 4.73 (m, 2H), 8.64 (d, 1H, J=8.0 Hz), 8.74 (q, 2H), 9.05 (d, 1H, J=8.0 Hz). Anal. calcd. for (C$_{30}$H$_{38}$N$_2$O$_3$S): C, 71.11; N, 7.56; H, 5.53. Found: C, 71.16; N, 7.35; H, 5.52.

cis-NDIS$_2$2EH, 350 mg, 16% yield, red solid. $^1$H NMR (CDCl$_3$, 500 MHz): δ 0.86-0.94 (m, 10H), 1.28-1.44 (m, 18H), 2.17 (m, 2H), 4.72 (m, 4H), 8.74 (s, 2H), 8.94 (s, 2H). Anal. calcd. for (C$_{30}$H$_{38}$N$_2$O$_2$S$_2$): C, 68.93; N, 7.33; H, 5.36. Found: C, 69.01; N, 7.10; H, 5.32.

trans-NDIS$_2$2EH, 300 mg, 14% yield, red solid. $^1$H NMR (CDCl$_3$, 500 MHz): δ 0.88-0.94 (m, 10H), 1.30-1.45 (m, 18H), 2.19 (m, 2H), 4.75 (m, 4H), 8.66 (d, 2H, J=8.0 Hz), 9.07 (d, 2H, J=8.0 Hz). Anal. calcd. for (C$_{30}$H$_{38}$N$_2$O$_2$S$_2$): C, 68.93; N, 7.33; H, 5.36. Found: C, 69.21; N, 7.16; H, 5.31.

NDIS$_3$2EH, 10 mg, 0.5% yield, dark red solid. $^1$H NMR (CDCl$_3$, 500 MHz): δ 0.87-0.93 (m, 10H), 1.26-1.43 (m, 18H), 2.18 (m, 1H), 2.34 (m, 1H), 4.74 (m, 2H), 5.54 (m, 2H), 8.62 (d, 1H, J=8.0 Hz), 8.83 (q, 2H), 8.94 (d, 1H, J=8.0 Hz). Anal. calcd. for (C$_{30}$H$_{38}$N$_2$OS$_3$): C, 66.87; N, 7.11; H, 5.20. Found: C, 65.31; N, 6.82; H, 4.83.

Example 1M

Preparation of SPDI-F

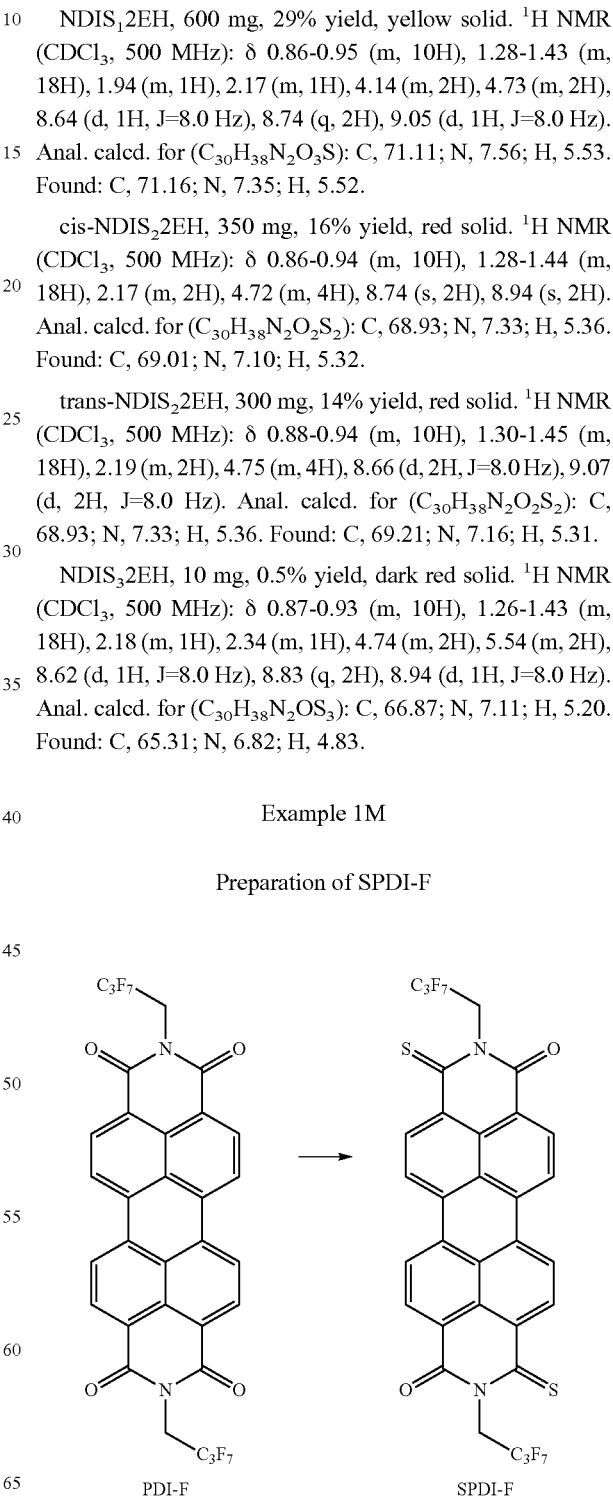

A mixture of 0.40 g (0.53 mmol) of PDI-F, 0.8 g (1.98 mmol) of Lawesson's Reagent, and 100 mL of 1-methylnaphthalene was heated in an oil bath at 180° C. for 15 minutes. The reaction mixture was then treated with 0.5 g of Davy Reagent and stirred for 15 minutes. The reaction mixture was then treated with another 0.5 g portion of Davy Reagent and stirred 30 minutes. The mixture was cooled in a water bath and purified by flash chromatography (SiO₂, toluene, 5.5×40 cm). The concentrated product fractions were sonicated with acetone, filtered, and dried to give SPDI-F as a black solid.

Example 1N

Preparation of trans-PDIS$_2$1MP-F$_2$

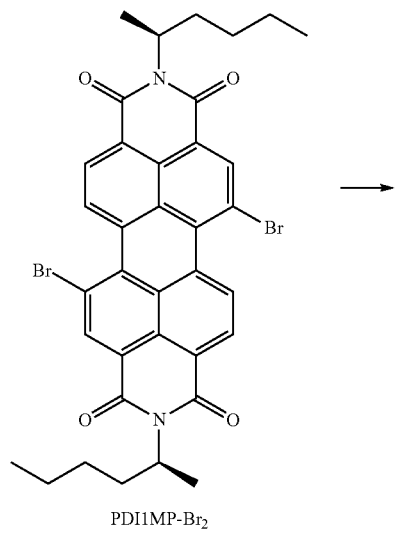

PDI1MP-Br$_2$

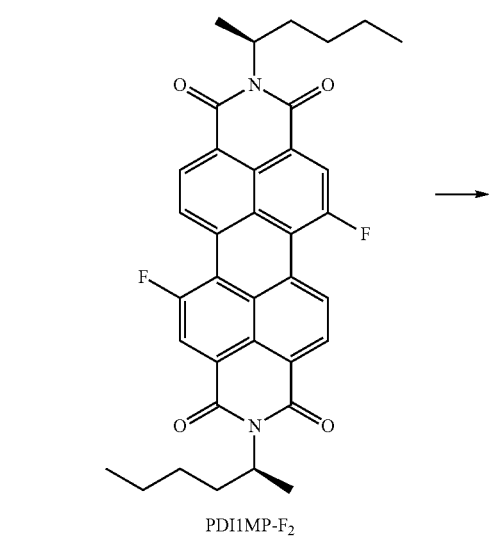

PDI1MP-F$_2$

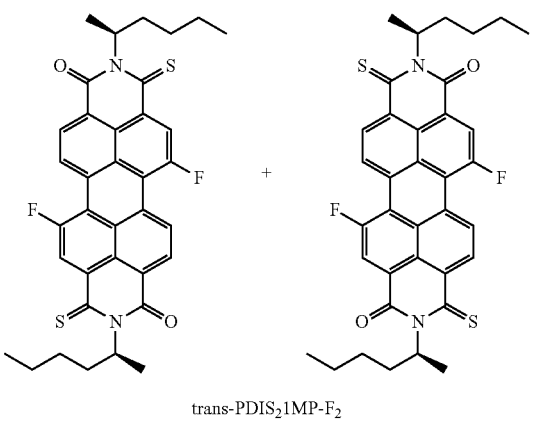

trans-PDIS$_2$1MP-F$_2$

A mixture of 1.20 g (2.18 mmol) of PDI1MP-Br$_2$ (as a mixture of 1,6- and 1,7-brominated isomers), 1.5 g (26.2 mmol) of potassium fluoride, 0.58 g (2.18 mmol) of 18-crown-6, and 60 mL of dimethyl sulfoxide was heated in an oil bath at 160° C. for 45 minutes. The mixture was cooled to room temperature and poured into 150 mL of water. The mixture was stirred for 10 minutes then filtered. The filter cake was washed with water then with methanol until the washings were colorless. The solid was then purified by flash chromatography (silica gel, chloroform, 4.5×25 cm) to give 0.60 g (46% yield) of PDI1MP-F$_2$ as a bright orange solid. $^1$H NMR (CDCl$_3$, 500 MHz): δ 9.15 (m, 2H), 8.71 (d, 2H), 8.52 (d, 2H), 5.29 (m, 2H), 2.27 (m, 2H), 1.93 (m, 2H), 1.63 (m, 6H), 1.3-1.1 (m, 8H), 0.87 (t, 6H, J=7.0).

A mixture of 0.266 g (0.447 mmol) of PDI1MP-F$_2$ (as a mixture of 1,6- and 1,7-fluorinated isomers), 0.55 g (1.36 mmol) of Lawesson's Reagent, and 5 mL of 1-methylnaphthalene was heated in an oil bath at 180° C. The mixture was stirred for 5 minutes then treated with 0.25 g of Lawesson's Reagent. The mixture was stirred for 5 minutes then treated with 0.25 g of Lawesson's Reagent. The mixture was stirred for 5 minutes, then cooled in a water bath and purified by flash chromatography (SiO$_2$, chloroform, 4.5×25 cm). The concentrated product fractions were sonicated with 20 mL of acetone, filtered, and dried to give trans-PDIS$_2$1MP-F$_2$ as a black crystalline solid. $^1$H NMR (CDCl$_3$, 500 MHz): δ 9.20-8.40 (m, 6H), 6.30 (m, 2H), 2.30 (m, 2H), 2.05 (m, 2H), 1.70-1.20 (m, 14H), 0.89 (t, 6H, J=7.0).

Example 1O

Preparation of S—C2OD-C6$_2$

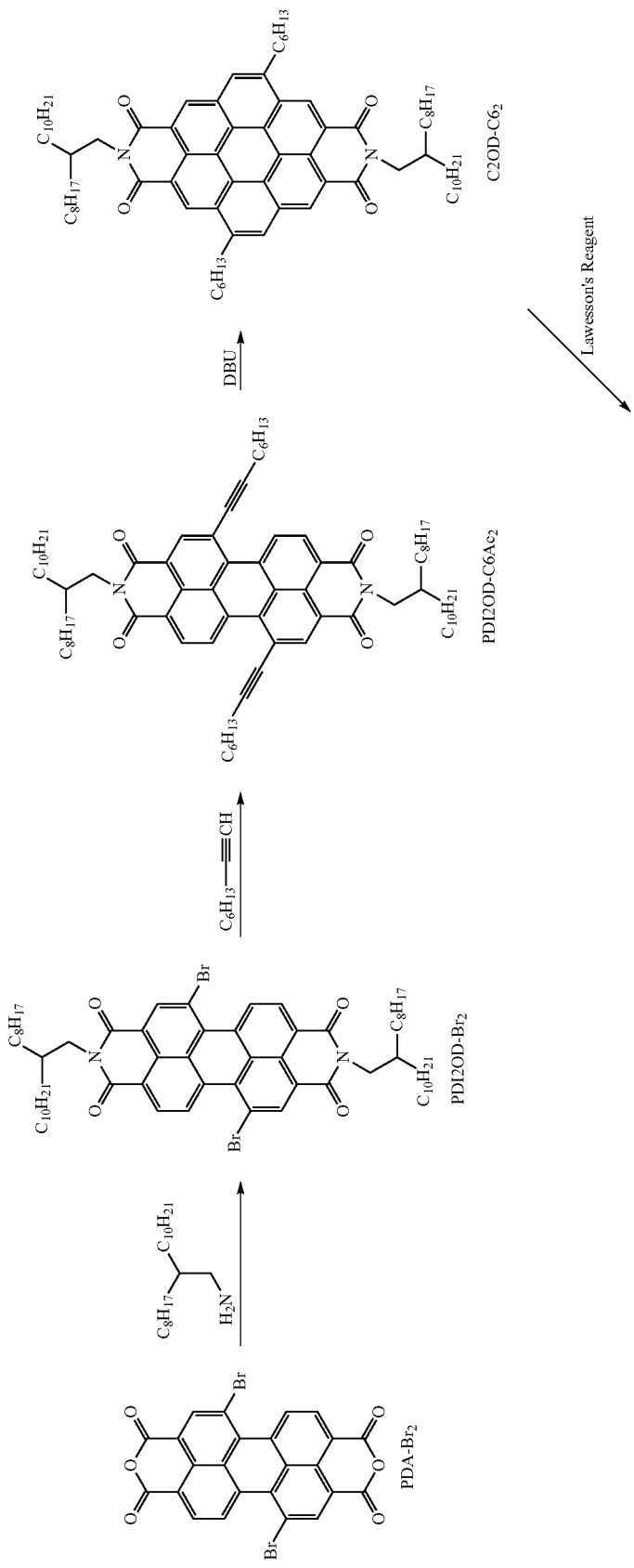

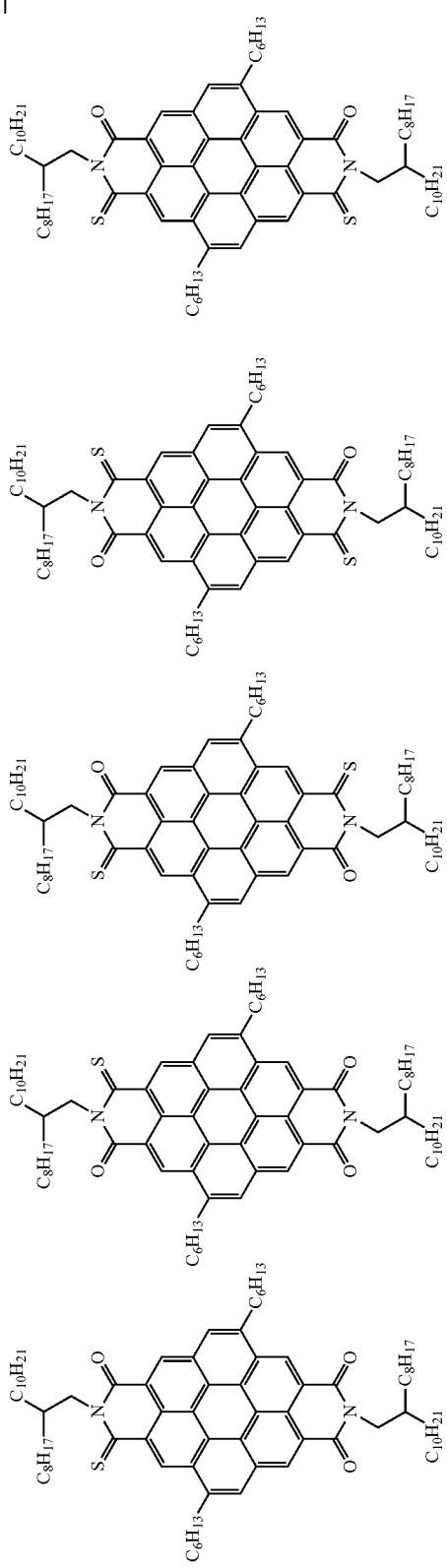
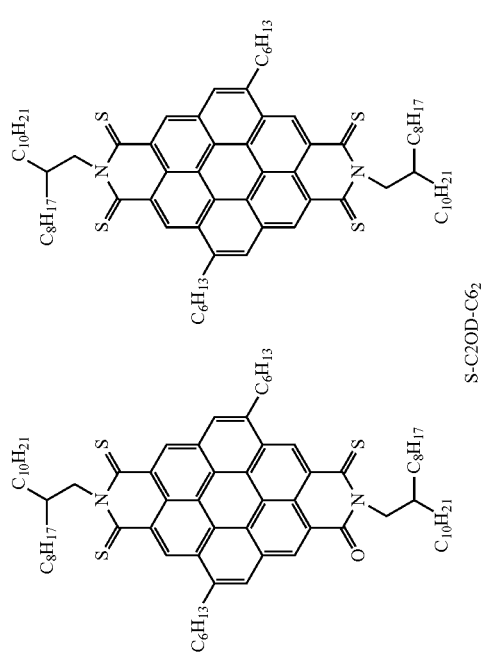

Synthesis of PDI2OD-Br$_2$: A mixture of PDA-Br$_2$ (3.48 g, 6.33 mmol), 2-octyldodecylamine (5.65 g, 18.99 mmol), propionic acid (7.9 mL), and o-xylene (24.0 mL) was heated at 140° C. for 24 hours in a sealed flask. The reaction mixture was then allowed to cool to room temperature, and concentrated on a rotary evaporator. The crude mixture was purified by flash column chromatography (silica gel, chloroform) to afford PDI2OD-Br$_2$ as a deep red solid (4.91 g, 70% yield).

$^1$H NMR (CDCl$_3$ 500 MHz): δ: 9.51 (d, 2H, J=8.0 Hz), 8.95 (s, 2H), 8.71 (d, 2H, J=8.0 Hz), 4.16 (d, 4H, J=7.0 Hz), 2.01 (m, 2H), 1.25-1.42 (m, 64H), 0.82-0.90 (m, 12H).

Synthesis of PDI2OD-C6A$_2$: Under nitrogen, 1-octyne (1.00 g, 9.1 mmol) was added to a mixture of PDI2OD-Br$_2$ (2.44 g, 2.2 mmol), Pd(PPh$_3$)$_4$ (0.24 g, 0.20 mmol), and CuI (0.04 g, 0.20 mmol) in anhydrous triethylamine (20 mL) and toluene (110 mL). The reaction mixture was heated at 80° C. for 18 hours, then it was cooled to room temperature and poured into water. Concentrated HCl (few drops) was added and the product extracted with CHCl$_3$ (3×50 mL). The combined fractions were washed twice with water and dried over MgSO$_4$. The solvent was removed under reduced pressure and the residue was purified by column chromatography (silica gel, CHCl$_3$-pentane) to give a dark red solid (1.77 g, 69%).

$^1$H NMR (CDCl$_3$): δ 9.97 (d, J=7.9 Hz, 2H), 8.66 (s, 2H), 8.54 (d, J=7.9 Hz, 2H), 4.18 (d, 4H, J=7.1 Hz), 2.65 (t, J=2.7 Hz, 4H), 2.02 (m, 2H), 1.8-1.1 (m, 80H), 0.82-0.90 (m, 18H). Anal. Calcd for C$_{80}$H$_{114}$N$_2$O$_4$: C, 82.28; H, 9.84; N, 2.40. Found: C, 81.98; H, 10.06; N, 2.47.

Synthesis of C2OD-C6$_2$: Under nitrogen, a mixture of PDI2OD-C6Ac$_2$ (1.57 g, 1.34 mmol) and 1,8-diazabicyclo[5.4.0]undec-7-ene (DBU, 1.6 mL) in toluene (150 mL) was heated to 100° C. After stirring for 20 hours, the mixture was cooled to room temperature, diluted with toluene (50 mL) and washed twice with diluted HCl (1N) and then with water. The solvent was removed under reduced pressure and the residue was purified by column chromatography (silica gel, CHCl$_3$-pentane) to give the product as a yellow solid (1.16 g, 74%).

$^1$H NMR (500 MHz, CDCl3): d 9.57 (s, 2H), 9.31 (s, 2H), 8.30 (s, 2H), 4.16 (d, 4H, J=7.1 Hz), 3.86 (t, J=6.8 Hz, 4H), 2.01 (m, 2H), 1.9-1.1 (m, 80H), 0.85-0.90 (m, 18H). Anal. Calcd for C$_{80}$H$_{114}$N$_2$O$_4$: C, 82.28; H, 9.84; N, 2.40. Found: C, 82.36; H, 9.77; N, 2.05.

Synthesis of S—C2OD-C6$_2$: A mixture of C2OD-C6$_2$ (0.50 g, 0.43 mmol) and Lawesson's Reagent (0.34 g, 0.84 mmol) in 50 mL of toluene was heated to reflux for 18 hours under nitrogen. The reaction mixture was cooled to room temperature and the solvent evaporated in vacuum to afford a dark solid (0.43 g after filtration over a silica-gel filter) composed of a mixture of S-coronene derivatives as identified by mass spectroscopy.

MS (MALDI): Calcd. for C$_{80}$H$_{114}$N$_2$O$_3$S: 1182.86; found 1183.01. Calcd for C$_{80}$H$_{114}$N$_2$O$_2$S$_2$: 1198.83; found 1198.07. Calcd. for C$_{80}$H$_{114}$N$_2$OS$_3$: 1214.81; found 1215.22. Calcd. for C$_{80}$H$_{114}$N$_2$S$_4$: 1230.79; found 1231.51.

Example 2

Preparation of Devices

Bottom-gate bottom-contact (BGBC) thin film transistors were prepared as follows: Step 1. Chromium (5 nm) plus gold (25 nm) were thermally evaporated on glass substrate as gate electrode. Step 2. Polyera Activink™ D1400 was spin-coated from anisole (150 mg/mL) at 1000 rpm as dielectric, followed by UV irradiation for 10 min. Step 3. Gold (30 nm) was thermally evaporated as S/D electrodes. Step 4. The S/D electrodes were treated with 2% 1-propanethiol/1-methylnaphthalene for 1 min., spun-off, and (S,S)-trans-PDIS$_2$1MP (10 mg/mL) in 1-methylnaphthalene was spin-coated at 4000 rpm for 6 s, followed by drying at 120° C. on a hotplate. Step 5. A baking step was performed on a 120° C. hotplate for 5 min.

Top-gate bottom-contact (TGBC) thin film transistors were prepared as follows: Step 1. Polyera Activink™ D1400 was spin-coated from 1:1 anisole/1,4-dioxane (80 mg/mL) at 4000 rpm as a planarization layer, followed by UV irradiation for 10 min. Step 2. Gold (30 nm) was thermally evaporated as S/D electrodes. Step 3. S/D electrodes were treated with 1-propanethiol vapor for 30 min., followed by 10 min. baking in a 110° C. vacuum oven. Step 4. (S,S)-trans-PDIS$_2$1MP/1-methylnaphthalene (10 mg/mL) was spin-coated at 1500 rpm for 12 s, then dried on a 120° C. hotplate, followed by baking for 5 min. Step 5. A polymeric dielectric, e.g., PMMA (50 mg/mL in an acetate formulation) was spin-coated on top as dielectric and baked on a 120° C. hotplate for 5 min. Step 6. Gold (30 nm) was thermally evaporated as gate electrode.

Table 3 summarizes exemplary charge transport properties of various devices made according to the procedures described above.

TABLE 3

Summary of electron mobilities (μ), on/off ratios, and V$_{on}$ for TFTs.

| Name | device | $\mu_{sat}$ (cm$^2$ V$^{-1}$ s$^{-1}$) | $I_{on/off}$ | $V_{on}$ (V) |
| --- | --- | --- | --- | --- |
| (S,S)-PDI1MP | TGBC | 2 × 10$^{-2}$ | 1 × 10$^{1-2}$ | 15~25 |
| (S,S)-PDIS$_1$1MP | TGBC | 1~5 × 10$^{-3}$ | 1 × 10$^{0-1}$ | 30~35 |
| (S,S)-PDIS$_2$1MP | TGBC | 1 × 10$^{-2}$ | 1 × 10$^{1-2}$ | 20~25 |
| (S,S)-trans-PDIS$_2$1MP | BGBC | 0.5~1.6 | 1 × 10$^{3-4}$ | −5~0 |
| (S,S)-trans-PDIS$_2$1MP | TGBC | 1~3.5 | 1 × 10$^4$ | −1~0 |
| (S,S)-PDIS$_3$1MP | TGBC | 1 × 10$^{-3}$ | 1 × 10$^{0-2}$ | 10~20 |
| trans-PDIS$_2$1MHex | TGBC | 1~2 × 10$^{-1}$ | 1 × 10$^{2-3}$ | 10~20 |
| cis-PDIS$_2$1Mhex | TGBC | 1~2 × 10$^{-2}$ | 1 × 10$^{1-2}$ | 20~30 |
| (S,S)-trans-PDIS$_2$1MHex | TGBC | 1.6~3 | 1 × 10$^{3-4}$ | −1~0 |
| (R,R)-trans-PDIS$_2$1MHept | TGBC | 1~3.3 | 1 × 10$^{3-4}$ | −5~0 |
| trans-PDIS$_2$1EPr | TGBC | 1 × 10$^{-3}$ | 1 × 10$^{1-3}$ | 15~25 |
| cis-PDIS$_2$1Epr | TGBC | 1~2 × 10$^{-3}$ | 1 × 10$^{1-3}$ | 15~25 |
| trans-NDIS$_2$Cy (vapor) | BGTC | 0.7~1.0 | 1 × 10$^{3-4}$ | −5~0 |
| trans-PDIS$_2$1MP-F$_2$ | TGBC | 0.2~0.3 | 1 × 10$^{4-5}$ | 0~5 |
| trans-PDIS$_2$1MP-CN$_2$ | TGBC | 4 × 10$^{-3}$ | 1 × 10$^{1-2}$ | 5~10 |

*Calculated from V$_g$ = 0 V to V$_g$ = 60 V.

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

The invention claimed is:

1. A compound having the formula:

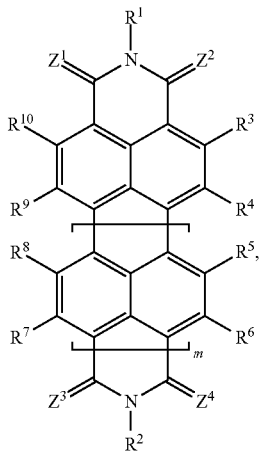

wherein:

$R^1$ and $R^2$ independently are selected from H, a $C_{1-40}$ alkyl group, a $C_{2-40}$ alkenyl group, a $C_{2-40}$ alkynyl group, a $C_{1-40}$ haloalkyl group, and a $C_{3-40}$ cycloalkyl group, wherein the $C_{1-40}$ alkyl group and the $C_{1-40}$ haloalkyl group optionally can be substituted with 1-5 substituents independently selected from a —CN, $NO_2$, —$SO_3H$, —$N(R^0)_3^+$, —$COR^0$, and —$COOR^0$; the $C_{2-40}$ alkenyl group and the $C_{2-40}$ alkynyl group optionally can be substituted with 1-5 substituents independently selected from a halogen, —CN, $NO_2$, —$SO_3H$, —$N(R^0)_3^+$, —$COR^0$, and —$COOR^0$; and the $C_{3-40}$ cycloalkyl group optionally can be substituted with 1-5 substituents independently selected from a halogen, —CN, $NO_2$, —$SO_3H$, —$N(R^0)_3^+$, —$COR^0$, —$COOR^0$, a $C_{1-40}$ alkyl group and a $C_{1-40}$ haloalkyl group, wherein $R^0$, at each occurrence, independently is H or a $C_{1-40}$ alkyl group;

$R^3$, $R^4$, $R^5$, $R^6$, $R^7$, $R^8$, $R^9$, and $R^{10}$, at each occurrence, independently is selected from H, F, Cl, Br, CN, $NO_2$, and a $C_{1-6}$ haloalkyl group;

$Z^1$, $Z^2$, $Z^3$, and $Z^4$ independently are selected from O, S, and Se, provided that at least one of $Z^1$, $Z^2$, $Z^3$, and $Z^4$ is S or Se; and m is 1.

2. The compound of claim 1 having a formula selected from:

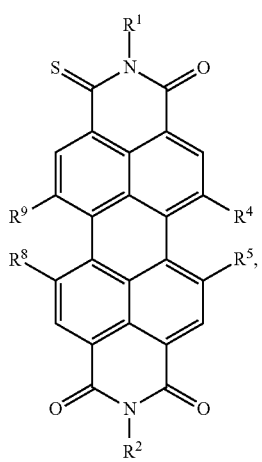

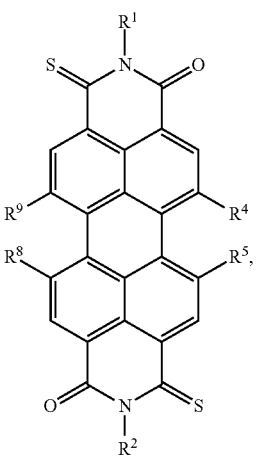

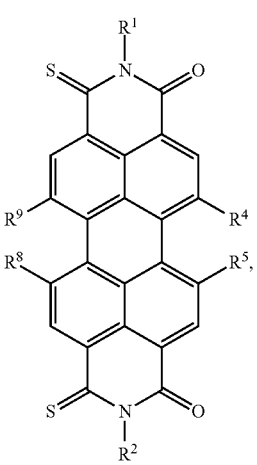

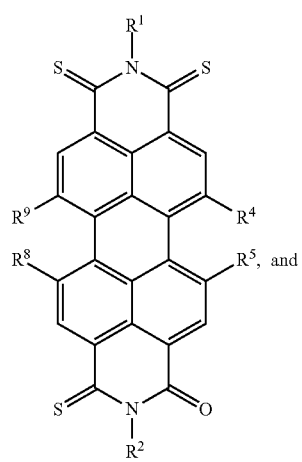

-continued

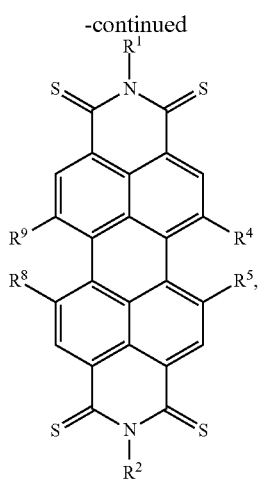

wherein $R^1$, $R^2$, $R^4$, $R^5$, $R^8$, and $R^9$ are as defined in claim 1.

3. The compound of claim 2, wherein:
each of $R^4$, $R^5$, $R^8$, and $R^9$ is H;
two of $R^4$, $R^5$, $R^8$, and $R^9$ are H, and the other two of $R^4$, $R^5$, $R^8$, and $R^9$ are selected from F, Cl, Br, and CN; or
two of $R^4$, $R^5$, $R^8$, and $R^9$ are CN, and the other two of $R^4$, $R^5$, $R^8$, and $R^9$ are selected from F, Cl, and Br.

4. The compound of claim 1 having a formula selected from:

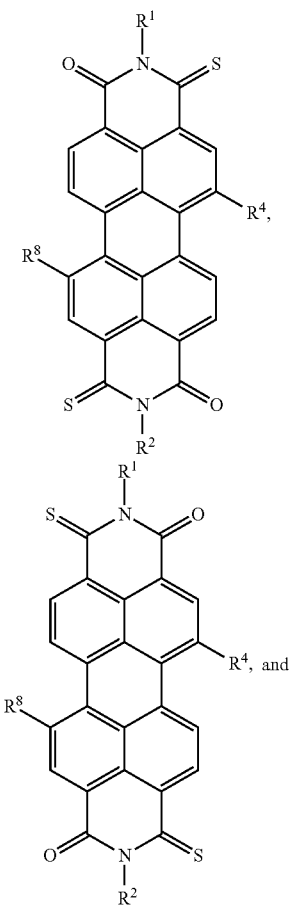

-continued

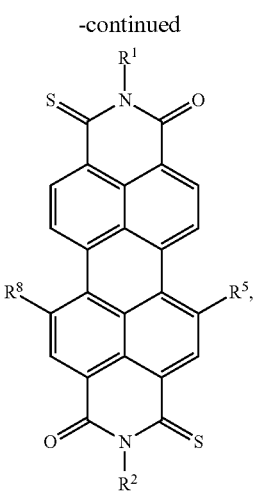

wherein $R^1$, $R^2$, $R^4$, $R^5$, and $R^8$ are as defined in claim 1.

5. The compound of claim 1 having a formula selected from:

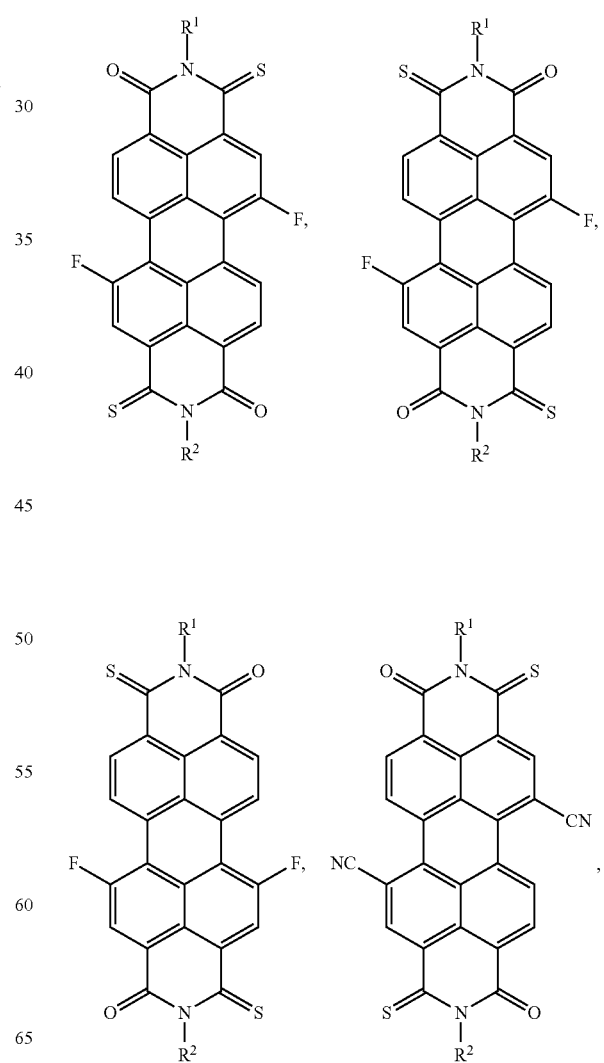

-continued

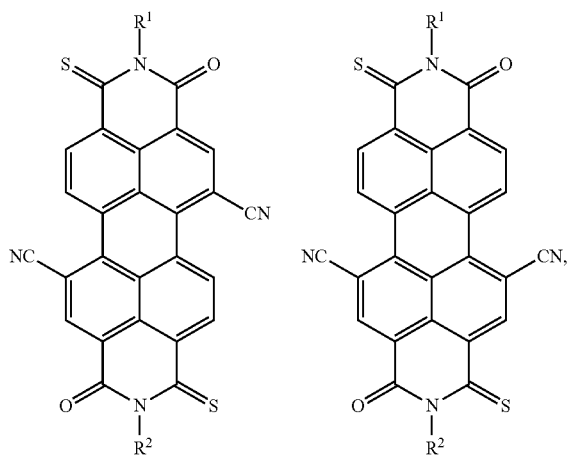

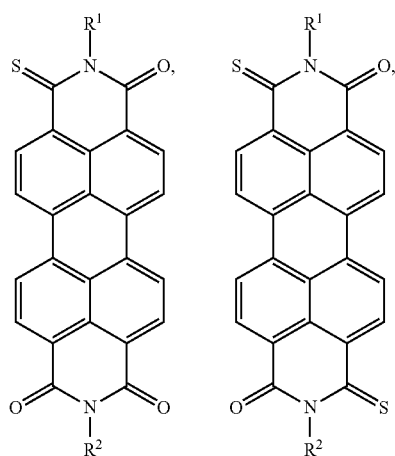

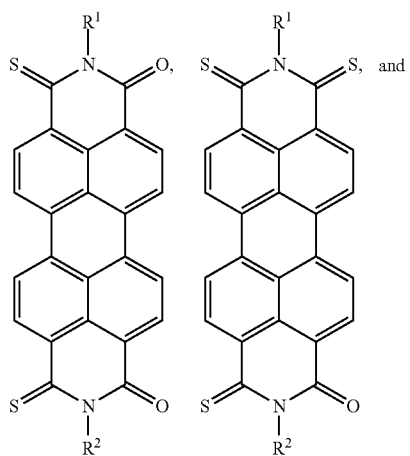

-continued

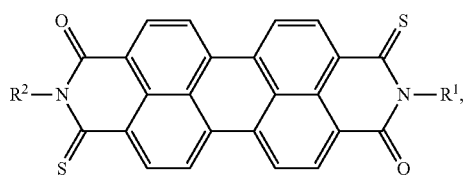

wherein $R^1$ and $R^2$ are as defined in claim 1.

6. The compound of claim 1 having the formula:

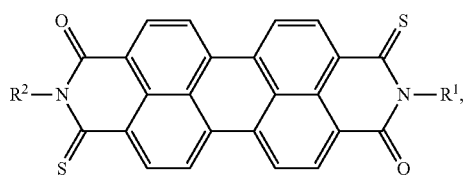

wherein $R^1$ and $R^2$ are as defined in claim 1.

7. The compound of claim 5, wherein $R^1$ and $R^2$ are selected from a $C_{1-40}$ alkyl group, a $C_{2-40}$ alkenyl group, a $C_{2-40}$ alkynyl group, a $C_{1-40}$ haloalkyl group, and a $C_{3-8}$-cycloalkyl group.

8. The compound of claim 7, wherein $R^1$ and $R^2$ are selected from a linear $C_{1-40}$ alkyl group, a linear $C_{2-40}$ alkenyl group, a linear $C_{1-40}$ haloalkyl group, a branched $C_{3-40}$ alkyl group, a branched $C_{4-40}$ alkenyl group, and a branched $C_{3-40}$ haloalkyl group.

9. The compound of claim 1 having a formula selected from:

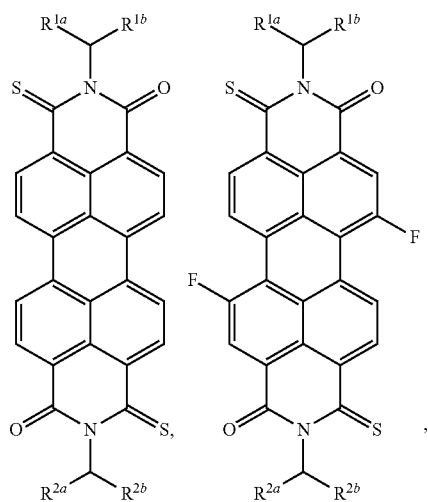

-continued

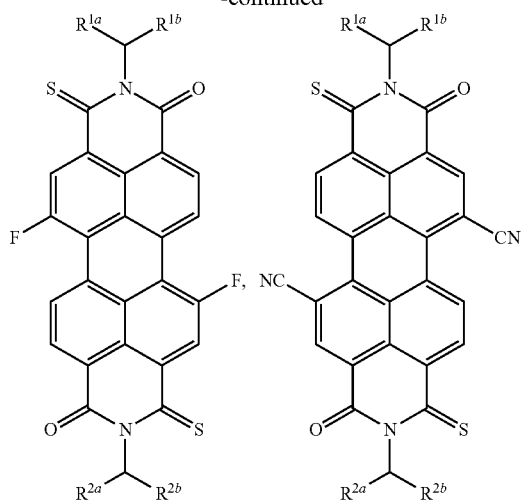

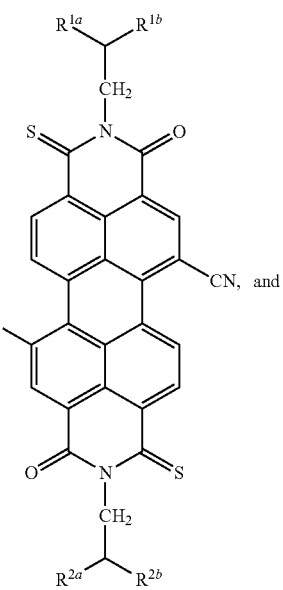

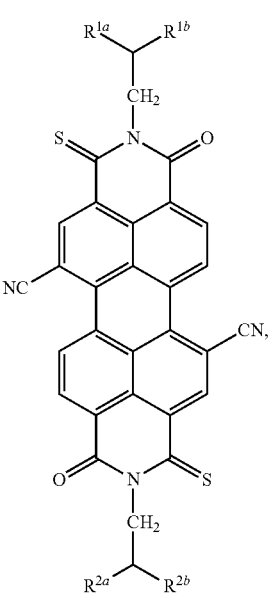

wherein $R^{1a}$, $R^{1b}$, $R^{2a}$ and $R^{2b}$ independently are a $C_{1-20}$ alkyl group or a $C_{1-20}$ haloalkyl group.

10. The compound of claim 9, wherein $R^{1a}$ and $R^{1b}$ are different, and $R^{2a}$ and $R^{2b}$ are different.

11. The compound of claim 9, wherein one of $R^{1a}$ and $R^{1b}$ is $CH_3$, and one of $R^{2a}$ and $R^{2b}$ is $CH_3$.

12. The compound of claim 9, wherein one of $R^{1a}$ and $R^{1b}$ is —$CH_2CH_3$, and one of $R^{2a}$ and $R^{2b}$ is —$CH_2CH_3$.

13. A compound selected from:
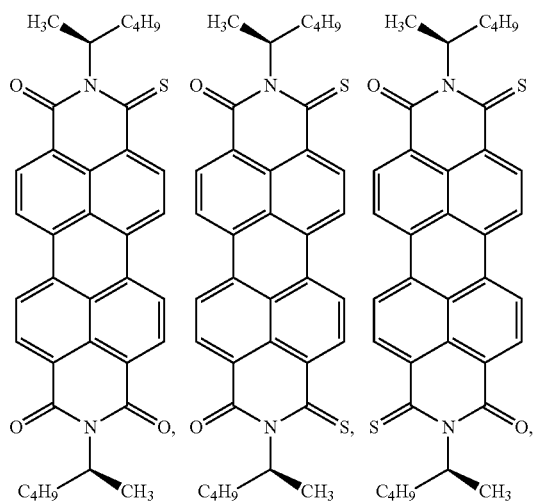
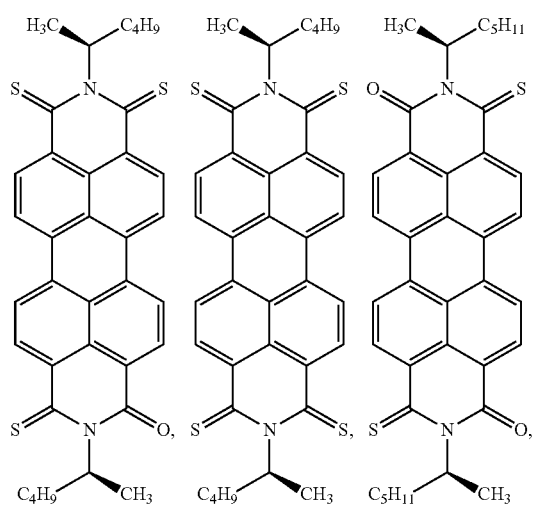
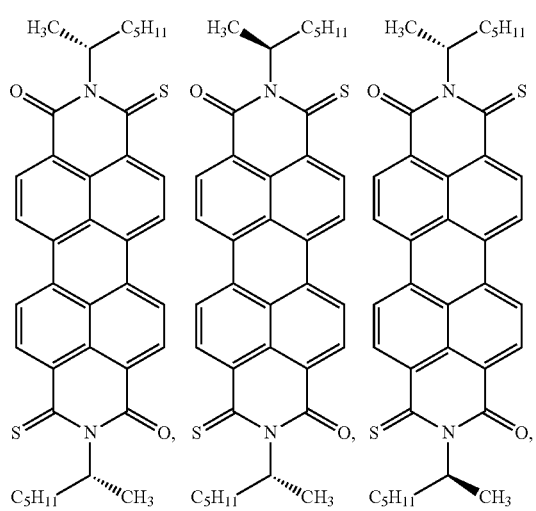
-continued
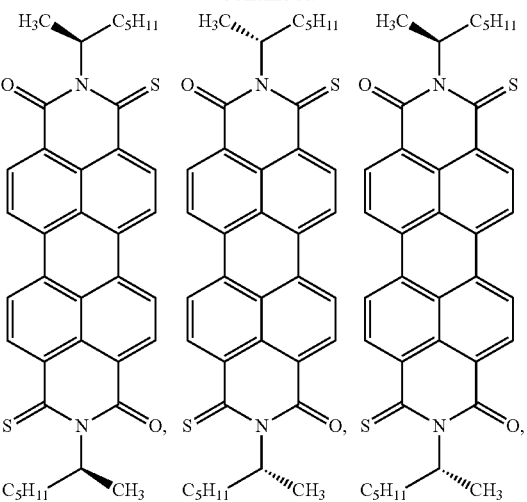
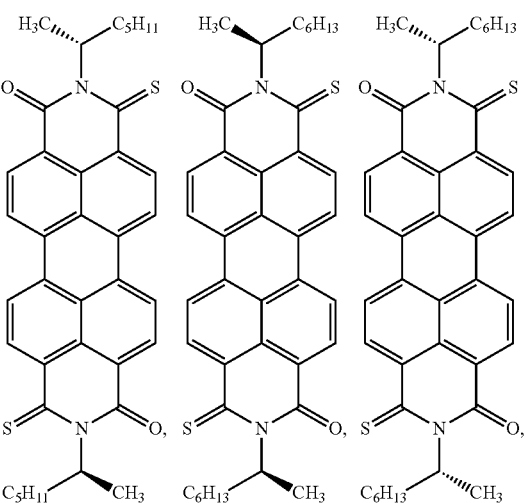
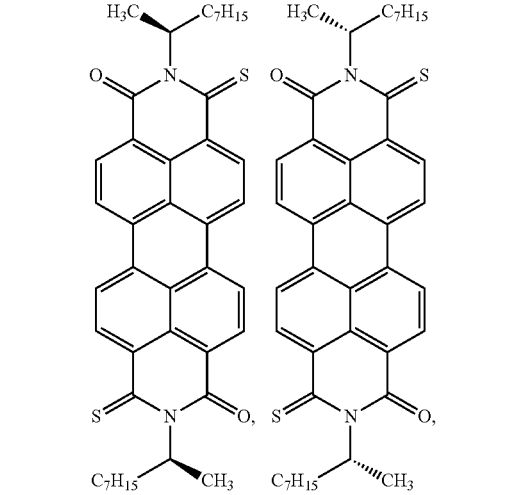

97
-continued
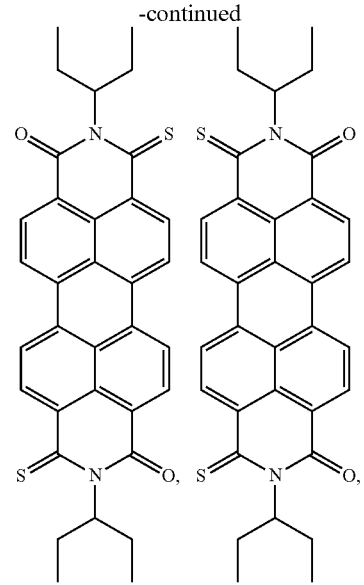
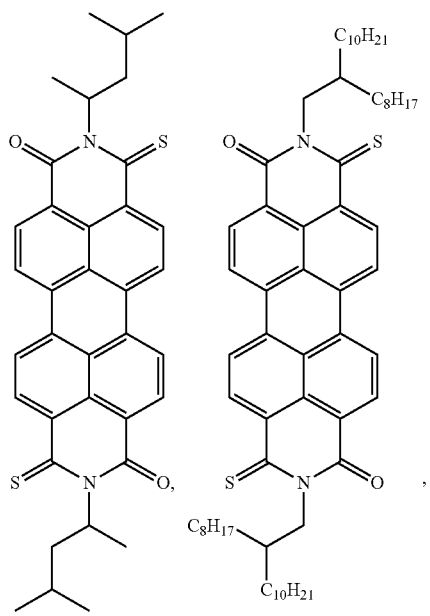
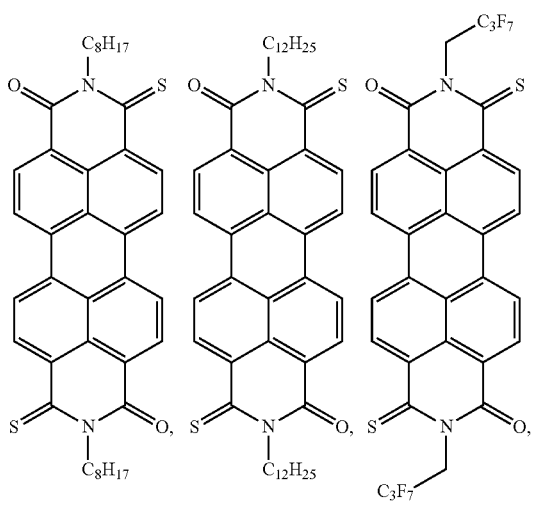
98
-continued
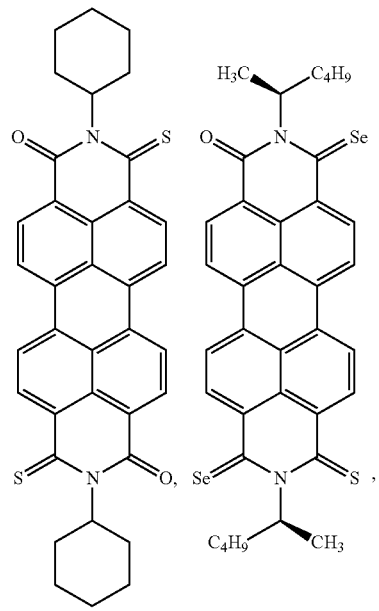
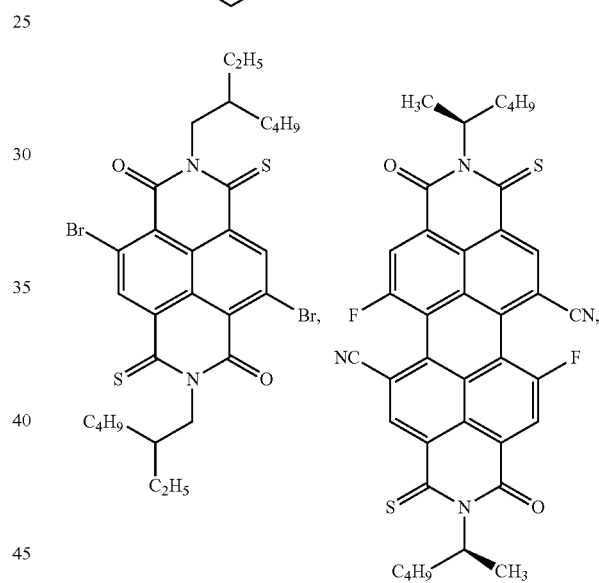
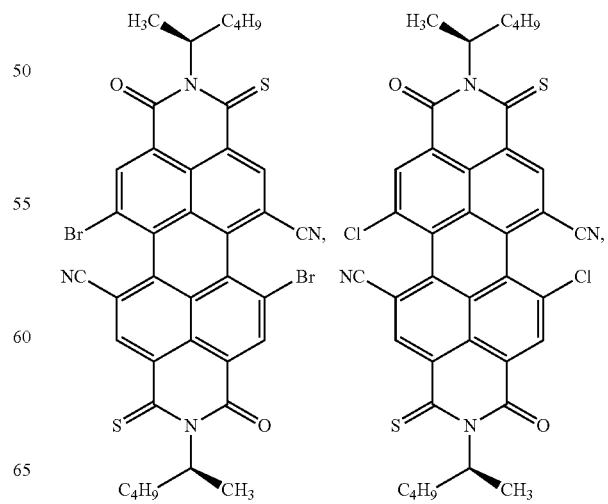

-continued

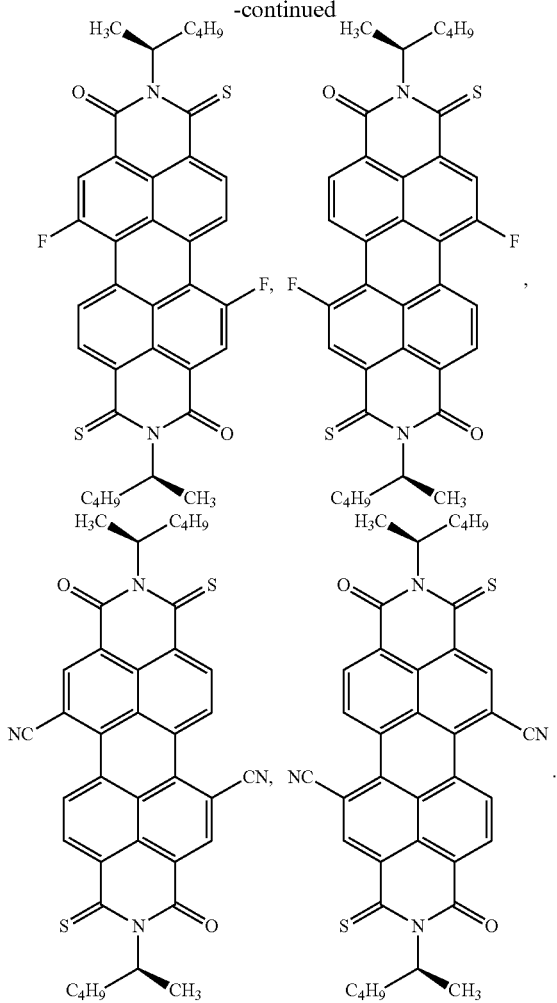

14. A composition comprising one or more compounds of claim 1 dissolved or dispersed in a liquid medium.

15. A semiconductor material comprising one or more compounds of claim 1.

16. A composite comprising a substrate and the semiconductor material of claim 15 deposited on the substrate.

17. An electronic, opto-electronic, or optical device comprising the semiconductor material of claim 15.

18. The device of claim 17, wherein the device is selected from an organic field-effect transistor, an organic light-emitting transistor, and an organic photovoltaic device.

19. An organic field-effect transistor or an organic light-emitting transistor comprising the semiconductor material of claim 15 and a dielectric material, wherein the dielectric material comprises an organic dielectric material, an inorganic dielectric material, or a hybrid organic/inorganic dielectric material.

20. An organic photovoltaic device comprising a p-type semiconductor material adjacent to the semiconductor material of claim 15.

* * * * *